US008642352B2

(12) United States Patent
Moss et al.

(10) Patent No.: US 8,642,352 B2
(45) Date of Patent: Feb. 4, 2014

(54) METHODS AND SYSTEMS FOR DETECTION OF STOICHIOMETRY BY FÖRSTER RESONANCE ENERGY TRANSFER

(75) Inventors: Fraser J. Moss, Bay Village, OH (US); Cagdas D. Son, Ankara (TR); Rahul Srinivasan, Pasadena, CA (US); Henry A. Lester, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 359 days.

(21) Appl. No.: 12/701,482

(22) Filed: Feb. 5, 2010

(65) Prior Publication Data

US 2010/0209938 A1 Aug. 19, 2010

Related U.S. Application Data

(60) Provisional application No. 61/206,958, filed on Feb. 6, 2009.

(51) Int. Cl.
*G01N 21/64* (2006.01)
(52) U.S. Cl.
USPC .............................. 436/172; 435/7.1; 436/805
(58) Field of Classification Search
None
See application file for complete search history.

(56) References Cited

U.S. PATENT DOCUMENTS

| 8,080,371 B2 | 12/2011 | Ballinger et al. | |
| 2003/0228703 A1* | 12/2003 | Hoppe et al. | 436/172 |
| 2004/0014135 A1* | 1/2004 | Cockett et al. | 435/7.1 |
| 2007/0258898 A1 | 11/2007 | Ballinger et al. | |
| 2007/0297991 A1* | 12/2007 | Peyman | 424/46 |
| 2009/0100532 A1* | 4/2009 | Drenan et al. | 800/3 |

OTHER PUBLICATIONS

Corry (2005) Biophy J 89: 3822-3836.*
Janetopoulos (2001) Science 291: 2408-2411.*
Lloyd (2000) J Pharm Exp Ther 292: 461-467.*
Gentry C.L. and R.J. Lukas. 2002. Regulation of nicotinic acetylcholine receptor numbers and function by chronic nicotine exposure. *Curr Drug Targets CNS Neurol Disord.* 1:359-385.
Roos A. and W.F. Boron. 1981. Intracellular pH. *Physiol. Rev.* 61:296-434.
Skok M.V., R. Grailhe, F. Agenes, and J.P. Changeux. 2007. The role of nicotinic receptors in B-lymphocyte development and activation. *Life Sci.* 80:2334-2336.
AbdAlla, S., H. Lother, A. el Massiery, and U. Quitterer. 2001. Increased $AT_1$ receptor heterodimers in preeclampsia mediate enhanced angiotensin II responsiveness. *Nat Med.* 7:1003-1009.
Abramoff MD, Magelhaes PJ and Ram SJ. 2004. Image Processing with ImageJ. *Biophotonics International* 11(7):36-42.
Amiri, H., G. Schultz, and M. Schaefer. 2003. FRET-based analysis of TRPC subunit stoichiometry. *Cell Calcium.* 33:463-470.

(Continued)

*Primary Examiner* — Chris L Chin
*Assistant Examiner* — Richard Moerschell
(74) *Attorney, Agent, or Firm* — Steinfl & Bruno LLP

(57) ABSTRACT

Methods to detect stoichiometries of protein complexes and/or interactions between proteins based on detection and quantification of FRET and related systems and compositions.

11 Claims, 25 Drawing Sheets

(56) References Cited

OTHER PUBLICATIONS

Amos C.I., X. Wu, P. Broderick, I.P. Gorlov, J. Gu, T. Eisen, Q. Dong, Q. Zhang, X. Gu, J. Vijayakrishnan, K. Sullivan, A. Matakidou, Y. Wang, G. Mills, K. Doheny, Y.Y. Tsai, W.V. Chen, S. Shete, M.R. Spitz, and R.S. Houlston. 2008. Genome-wide association scan of tag SNPs identifies a susceptibility locus for lung cancer at 15q25.1. *Nat Genet.* 40:616-622.

Armstrong C.M. 1971. Interaction of tetraethylamonium ion derivitives with the potassium channels of giant axons. *J. Gen. Physiol.* 58:413-437.

Arredondo J., A.I. Chernyaysky, R.J. Webber, and S. A. Grando. 2005. Biological effects of SLURP-1 on human keratinocytes. *J Invest Dermatol.* 125:1236-1241.

Arredondo J., A.I. Chernyaysky, and S.A. Grando. 2006. The nicotinic receptor antagonists abolish pathobiologic effects of tobacco-derived nitrosamines on BEP2D cells. *J Cancer Res Clin Oncol.* 132:653-663.

Arredondo J., A.I. Chernyaysky, and S.A. Grando. 2007. SLURP-1 and -2 in normal, immortalized and malignant oral keratinocytes. *Life Sci.* 80:2243-2247.

Azam L., Y. Chen, and F.M. Leslie. 2007. Developmental regulation of nicotinic acetylcholine receptors within midbrain dopamine neurons. *Neuroscience.* 144:1347-1360.

Bal, M. et al. 2008. Calmodulin binding to M-type $K^+$ channels assayed by TIRF/FRET in living cells. *J. Physiol* 586(9):2307-2320.

Bal, M. et al. 2008. Homomeric and Heteromeric Assembly of KCNQ (Kv7) $K^+$ Channels Assayed by Total Internal Reflection Fluorescence/Fluorescence Resonance Energy Transfer and Patch Clamp Analysis. *J. Biological Chemistry* 283(45): 30668-30676.

Balch WE, Morimoto RI, Dillin A. and Kelly JW. 2008. Adapting Proteostasis for Disease Intervention. *Science* 319(5865):916-919.

Bartholomaus, I. et al. 2008. Glycine Transporter Dimers. *J. BioChem.* 283(16):10978-10991.

Bartol T.M., B.R. Land, E.E. Salpeter, and M.M. Salpeter. 1991. Monte-Carlo simulation of miniature end-plate current generation in the vertebrate neuromuscular junction. *Biophys.* J. 59:1290-1307.

Bauman, P.A. et al. 2002. Determinants within the C-terminus of the human norepinephrine transporter dictate transporter trafficking, stability, and activity. *Arch. Biochem Biophys.* 404:80-91.

Beene D.L., G.S. Brandt, W. Zhong, N.M. Zacharias, H.A. Lester, and D.A. Dougherty. 2002. Cation-πinteractions in ligand recognition by serotonergic (5-HT3$_A$) and nicotinic acetylcholine receptors: the anomalous binding properties of nicotine. *Biochemistry.* 41:10262-10269.

Benowitz, N.L., F. Kuyt, and P. Jacob, 3rd. 1982. Circadian blood nicotine concentrations during cigarette smoking. *Clin Pharmacol Ther.* 32:758-764. doi:0009-9236(82)90198-9 [pii].

Berrettini W., X. Yuan, F. Tozzi, K. Song, C. Francks, H. Chilcoat, D. Waterworth, P. Muglia, and V. Mooser. 2008. α5/α3 nicotinic receptor subunit alleles increase risk for heavy smoking. *Mol Psychiatry.* 13:368-373.

Bertoni, J.M., J.L. Prendes, and P. Sprenkle. 2001. Long-term Medical Treatment for Parkinson's Disease. *Curr Treat Options Neurol.* 3:495-506.

Bertrand, D., F. Picard, S. Le Hellard, S. Weiland, I. Favre, H. Phillips, S. Bertrand, S.F. Berkovic, A. Malafosse, and J. Mulley. 2002. How mutations in the nAChRs can cause ADNFLE epilepsy. *Epilepsia.* 43 Suppl 5:112-122.

Bethony, J., S. Brooker, M. Albonico, S.M. Geiger, A. Loukas, D. Diemert, and P.J. Hotez. 2006. Soil-transmitted helminth infections: ascariasis, trichuriasis, and hookworm. *Lancet.* 367:1521-1532.

Bierut L.J., J.A. Stitzel, J.C. Wang, A.L. Hinrichs, R.A. Grucza, X. Xuei, N.L. Saccone, S.F. Saccone, S. Bertelsen, L. Fox, W.J. Horton, N. Breslau, J. Budde, C.R. Cloninger, D.M. Dick, T. Foroud, D. Hatsukami, V. Hesselbrock, E.O. Johnson, J. Kramer, S. Kuperman, P.A. Madden, K. Mayo, J. Nurnberger, Jr., O. Pomerleau, B. Porjesz, O. Reyes, M. Schuckit, G. Swan, J.A. Tischfield, H.J. Edenberg, J.P. Rice, and A.M. Goate. 2008. Variants in nicotinic receptors and risk for nicotine dependence. *Am J Psychiatry.* 165:1163-1171.

Bierut L.J., P.A. Madden, N. Breslau, E.O. Johnson, D. Hatsukami, O.F. Pomerleau, G.E. Swan, J. Rutter, S. Bertelsen, L. Fox, D. Fugman, A.M. Goate, A.L. Hinrichs, K. Konvicka, N.G. Martin, G.W. Montgomery, N.L. Saccone, S.F. Saccone, J.C. Wang, G.A. Chase, J.P. Rice, and D.G. Ballinger. 2007. Novel genes identified in a high-density genome wide association study for nicotine dependence. *Hum Mol Genet.* 16:24-35.

Bjerggaard, C. et al. 2004. Surface Targeting of the Dopamine Transporter Involves Discrete Epitopes in the Distal C Terminus But Does Not Require Canonical PDZ Domain Interactions. *J. Neurosci.* 24(31):7024-7036.

Blackman, S.M. et al. 1998. Oligomeric State of Human Erythrocyte Band 3 Measured by Fluorescence Resonance Energy Homotransfer. *Biophys J.* 75:1117-1130.

Boudanova, E., D.M. Navaroli, Z. Stevens, and H.E. Melikian. 2008. Dopamine transporter endocytic determinants: carboxy terminal residues critical for basal and PKC-stimulated internalization. *Mol Cell Neurosci.* 39:211-217.

Boulin, T., M. Gielen, J.E. Richmond, D.C. Williams, P. Paoletti, and J.L. Bessereau. 2008. Eight genes are required for functional reconstitution of the *Caenorhabditis elegans* levamisole-sensitive acetylcholine receptor. *Proc Natl Acad Sci U.S.A.* 105:18590-18595.

Boyd, C. et al. 2004. Vesicles carry most exocyst subunits to exocytic sites marked by the remaining two subunits, Sec3p and Exo70p. *J.Cell Bio* 167(5):889-901.

Breese C.R., M.J. Marks, J. Logel, C.E. Adams, B. Sullivan, A.C. Collins, and S. Leonard. 1997. Effect of smoking history on [$^3$H] nicotine binding in human postmortem brain. *Journal of Pharmacology and Experimental Therapeutics.* 282:7-13.

Briggs, C.A., E.J. Gubbins, M.J. Marks, C.B. Putman, R. Thimmapaya, M.D. Meyer, and C.S. Surowy. 2006. Untranslated region-dependent exclusive expression of high-sensitivity subforms of α4β2 and α3β2 nicotinic acetylcholine receptors. *Mol Pharmacol.* 70:227-240.

Brodtkorb, E., and F. Picard. 2006. Tobacco habits modulate autosomal dominant nocturnal frontal lobe epilepsy. *Epilepsy Behav.* 9:515-520.

Brown R.W., A.C. Collins, J.M. Lindstrom, and P. Whiteaker. 2007. Nicotinic α5 subunit deletion locally reduces high-affinity agonist activation without altering nicotinic receptor numbers. *J Neurochem.* 103:204-215.

Bruckner, K., J. Pablo Labrador, P. Scheiffele, A. Herb, P.H. Seeburg, and R. Klein. 1999. EphrinB ligands recruit GRIP family PDZ adaptor proteins into raft membrane microdomains. *Neuron.* 22:511-524.

Buisson, B., and D. Bertrand. 2001. Chronic exposure to nicotine upregulates the human☐ α4βB nicotinic acetylcholine receptor function. *J Neurosci.* 21:1819-1829.

Buttini M., et al. 2002. Modulation of Alzheimer-like synaptic and cholinergic deficits in transgenic mice by human apolipoprotein E depends on isoform, aging, and overexpression of amyloid beta peptides but not on plaque formation. *J Neurosci* 22(24):10539-10548.

Carriba, P., O. Ortiz, K. Patkar, Z. Justinova, J. Stroik, A. Themann, C. Muller, A.S. Woods, B.T. Hope, F. Ciruela, V. Casado, E.I. Canela, C. Lluis, S.R. Goldberg, R. Moratalla, R. Franco, and S. Ferre. 2007. Striatal adenosine $A_{2A}$ and cannabinoid $CB_1$ receptors form functional heteromeric complexes that mediate the motor effects of cannabinoids. *Neuropsychopharmacology.* 32:2249-2259.

Cashin A.L., E.J. Petersson, H.A. Lester, and D.A. Dougherty. 2005. Using physical chemistry to differentiate nicotinic from cholinergic agonists at the nicotinic acetylcholine receptor. *J Am Chem Soc.* 127:350-356.

Champtiaux, N., C. Gotti, M. Cordero-Erausquin, D.J. David, C. Przybylski, C. Lena, F. Clementi, M. Moretti, F.M. Rossi, N. Le Novere, J.M. McIntosh, A.M. Gardier, and J.P. Changeux. 2003. Subunit composition of functional nicotinic receptors in dopaminergic neurons investigated with knock-out mice. *J Neurosci.* 23:7820-7829.

Charnet P., C. Labarca, B.N. Cohen, N. Davidson, H.A. Lester, and G. Pilar.1992. Pharmacological and kinetic properties of α4β2 neuronal nicotinic acetylcholine receptors expressed in Xenopus oocytes. *J Physiol.* 450:375-394.

(56) References Cited

OTHER PUBLICATIONS

Chen, L., G.B. Martin, and G.A. Rechnitz. 1992. Microtiter plate binding assay for cholinergic compounds utilizing the nicotinic acetylcholine receptor. *Anal Chem.* 64:3018-3023.

Chen, N., et al. 2008. Substrates dissociate dopamine transport oligomers. *J. Neurochem.* 105:910-920.

Chimienti F., R.C. Hogg, L. Plantard, C. Lehmann, N. Brakch, J. Fischer, M. Huber, D. Bertrand, and D. Hohl. 2003. Identification of SLURP-1 as an epidermal neuromodulator explains the clinical phenotype of Mal de Meleda. *Hum Mol Genet.* 12:3017-3024.

Chiu, C.S. et al. 2001. Single-molecule measurements calibrate green fluorescent protein surface densities on transparent beads for use with 'knock-in' animals and other expression systems. *J Neu Meth.* 105:55-63.

Chiu, C.S., K. Jensen, I. Sokolova, D. Wang, M. Li, P. Deshpande, N. Davidson, I. Mody, M.W. Quick, S.R. Quake, and H.A. Lester. 2002. Number, density, and surface/cytoplasmic distribution of GABA transporters at presynaptic structures of knock-in mice carrying GABA transporter subtype 1-green fluorescent protein fusions. *J Neurosci.* 22:10251-10266.

Cole, N.B. et al. 1996. Diffusional Mobility of Golgi Proteins in Membranes of Living Cells. *Science.* 273(5276):797-801.

Combi, R., L. Dalpra, M.L. Tenchini, and L. Ferini-Strambi. 2004. Autosomal dominant nocturnal frontal lobe epilepsy—a critical overview. *J Neurol.* 251:923-934.

Corry, B. et al. 2005 Conformational Changes Involved in MscL Channel Gating Measured using FRET Spectroscopy. *Biophys J: Biophys Letters.* L49-L51.

Corry, B. et al. 2005. A flexible approach to the calculation of resonance energy transfer efficiency between multiple donors and acceptors in complex geometries. *Biophys J.* 89:3822-3836.

Corry, B. et al. 2006. Determination of the orientational distribution and orientation factor for transfer between membrane-bound fluorophores using a confocal microscope. *Biophys J.* 91:1032-1045.

Corry, B. et al. 2008 Simulation of structure, orientation, and energy transfer between AlexaFluor molecules attached to MscL. *Biophys J.* 95(6):2711-2721.

Costa, G., J.A. Abin-Carriquiry, and F. Dajas. 2001. Nicotine prevents striatal dopamine loss produced by 6-hydroxydopamine lesion in the substantia nigra. *Brain Res.* 888:336-342.

Crespel, A, Baldy-Moulinier M and Coubes P (1998) The relationship between sleep and epilepsy in frontal and temporal lobe epilepsies: practical and physiopathologic considerations. *Epilepsia* 39(2):150-157.

Crompton, D.W. 2001. Ascaris and ascariasis. *Adv Parasitol.* 48:285-375.

Cui, C. et al. 2003. The β3 Nicotinic Receptor Subunit: A Component of β-Conotoxin MII-Binding Nicotinic Acetylcholine Receptors that Modulate Dopamine Release and Related Behaviors. *J. Neurosci.* 23(35): 11045-11053.

Darsow, T., T.K. Booker, J.C. Pina-Crespo, and S.F. Heinemann. 2005. Exocytic trafficking is required for nicotine-induced up-regulation of α4β2 nicotinic acetylcholine receptors. *J Biol Chem* 280:18311-18320.

Deken, S.L. et al. 2003. Plasma Membrane GABA Transporters Reside on Distinct Vesicles and Undergo Rapid Regulated Recycling. *J. Neurosci.* 23(5):1563-1568.

Derry, CP, Duncan JS and Berkovic SF (2006) Paroxysmal motor disorders of sleep: the clinical spectrum and differentiation from epilepsy. *Epilepsia* 47(11):1775-1791.

Derry et al. 2006 "Distinguishing Sleep Disorders From Seizures" *Arch Neurol.*, 63, 705-709.

Doherty, G.J. et al. 2009. Mechanisms of Endocytosis. *AnnRev Biochem.* 78:857-902.

Drenan, R.M., R. Nashmi, P.I. Imoukhuede, H. Just, S. McKinney, and H.A. Lester. 2008. Subcellular Trafficking, Pentameric Assembly and Subunit Stoichiometry of Neuronal Nicotinic ACh Receptors Containing Fluorescently-Labeled α6 and β3 Subunits. *Mol Pharmacol.* 73:27-41.

El-Bizri H. and P.B. Clarke. 1994. Regulation of nicotinic receptors in rat brain following quasi-irreversible nicotinic blockade by chlorisondamine and chronic treatment with nicotine. *Br. J. Pharmacol.* 113:917-925.

Elangovan, M., H. Wallrabe, Y. Chen, R.N. Day, M. Barroso, and A. Periasamy. 2003. Characterization of one- and two-photon excitation fluorescence resonance energy transfer microscopy. *Methods.* 29:58-73.

Farhan, H. et al. 2004. Two discontinuous segments in the carboxyl terminus are required for membrane targeting of the rat gamma-aminobutyric acid transporter-1 (GAT1). *J. Biol Chem.* 279(27):28553-28563.

Farhan, H. et al. 2006. Oligomerization of Neurotransmitter Transporters: A Ticket from the Endoplasmic Reticulum to the Plasma Membrane. *HEP.* 175:233-249.

Farhan, H., V. Reiterer, A. Kriz, H.P. Hauri, M. Pavelka, H.H. Sitte, and M. Freissmuth. 2008. Signal-dependent export of GABA transporter 1 from the ER-Golgi intermediate compartment is specified by a C-terminal motif. *J Cell Sci.* 121:753-761.

Farhan, H., V. Reiterer, V.M. Korkhov, J.A. Schmid, M. Freissmuth, and H.H. Sitte. 2007. Concentrative Export from the Endoplasmic Reticulum of the α-Aminobutyric Acid Transporter 1 Requires Binding to SEC24D. *J Biol Chem.* 282:7679-7689.

Farrar, S.J., P.J. Whiting, T.P. Bonnert, and R.M. McKernan. 1999. Stoichiometry of a ligand-gated ion channel determined by fluorescence energy transfer. *J Biol Chem.* 274:10100-10104.

Feige, J.N., D. Sage, W. Wahli, B. Desvergne, and L. Gelman. 2005. PixFRET, an ImageJ plug-in for FRET calculation that can accommodate variations in spectral bleed-throughs. *Microsc Res Tech.* 68:51-58.

Feigin, A. 2003. Nondopaminergic symptomatic therapies for Parkinson's disease: turn on or turn off? *Neurology.* 61:286-287.

Fenster, C.P. et al. 1999. Upregulation of surface α4β2 nicotinic receptors is initiated by receptor desensitization after chronic exposure to nicotine. *J. Neuroscience* 19(12):4804-4814.

Ferini-Strambi L, Baietto C, Di Gioia MR, Castaldi P, Castronovo C, Zucconi M and Cappa SF (2003) Cognitive dysfunction in patients with obstructive sleep apnea (OSA): partial reversibility after continuous positive airway pressure (CPAP). *Brain Res Bull* 61(1):87-92.

Figl, A., N. Viseshakul, N. Shafaee, J. Forsayeth, and B.N. Cohen. 1998. Two mutations linked to nocturnal frontal lobe epilepsy cause use-dependent potentiation of the nicotinic ACh response. *J Physiol (Lond).* 513:655-670.

Fischer H., A. Orr-Urtreger, L.W. Role, and S. Huck. 2005. Selective deletion of the α5 subunit differentially affects somatic-dendritic versus axonally targeted nicotinic ACh receptors in mouse. *J Physiol.* 563:119-137.

Fonck C., R. Nashmi, R. Salas, C. Zhou, Q. Huang, M. De Biasi, R.A. Lester, and H.A. Lester. 2009. Demonstration of functional α4-containing nicotinic receptors in the medial habenula. *Neuropharmacology* 56: 247-253.

Fonck, C., B.N. Cohen, R. Nashmi, P. Whiteaker, D. Wagenaar, N. Rodrigues-Pinguet, P. Deshpande, S. Kwoh, J. Munoz, C. Labarca, A.C. Collins, M. Marks, and H.A. Lester. 2005. Novel seizure phenotype and sleep disruptions in knock-in mice with hypersensitive α4 nicotinic receptors. *J Neurosci.* 25:11396-113411.

Fonck, C., R. Nashmi, P. Deshpande, M. Damaj, M. Marks, A. Riedel, J. Schwarz, A.C. Collins, C. Labarca, and H.A. Lester. 2003. Increased sensitivity to agonist-induced seizures, Straub tail, and hippocampal theta rhythm in knock-in mice carrying hypersensitive α4 nicotinic receptors. *J Neurosci.* 23:2582-2590.

Gahring, L.C., K. Persiyanov, and S.W. Rogers. 2005. Mouse strain-specific changes in nicotinic receptor expression with age. *Neurobiol Aging.* 26:973-980.

Gauthier, N. C. et al. 2007. Early endosomes associated with dynamic F-actin structures are required for late trafficking of *H. pylori* VacA toxin. *J. Cell Bio.* 177(2)343-354.

Geiser, M., R. Cebe, D. Drewello, and R. Schmitz. 2001. Integration of PCR fragments at any specific site within cloning vectors without the use of restriction enzymes and DNA ligase. *Biotechniques.* 31:88-90, 92.

(56) References Cited

OTHER PUBLICATIONS

Gentry et al. "Effects of Prolonged Nicotinic Ligand Exposure on Function of Heterologously Expressed, Human α4β2- and α4β4-Nicotinic Acetylcholine Receptors" *J. Phrmacol. Exp. Ther.* 2003, 304, 206-216.
Gonzalez-Maeso, J., R.L. Ang, T. Yuen, P. Chan, N.V. Weisstaub, J.F. Lopez-Gimenez, M. Zhou, Y. Okawa, L.F. Callado, G. Milligan, J.A. Gingrich, M. Filizola, J.J. Meana, and S.C. Sealfon. 2008. Identification of a novel serotonin/glutamate receptor complex implicated in psychosis. *Nature*. 452:93-97.
Gopalakrishnan M., L.M. Monteggia, D.J. Anderson, E.J. Molinari, M. Piattoni-Kaplan, D. Donnelly-Roberts, S.P. Arneric, and J.P. 1996. Sullivan. Stable expression, pharmacologic properties and regulation of the human neuronal nicotinic acetylcholine α4β2 receptor. *J Pharmacol Exp Ther*. 276:289-297.
Gopalakrishnan, M. et al. 1997. Regulation of Human α4β2 Neuronal Nicotinic Acetylcholine Receptors by Cholinergic Channel Ligands and Second Messenger Pathways. *Mol. Pharm.* 52:524-534.
Gordon, G.W., G. Berry, X.H. Liang, B. Levine, and B. Herman. 1998. Quantitative fluorescence resonance energy transfer measurements using fluorescence microscopy. *Biophys J*. 74:2702-2713.
Gotti C., M. Zoli, and F. Clementi. 2006. Brain nicotinic acetylcholine receptors: native subtypes and their relevance. *Trends Pharmacol Sci*. 27:482-491.
Grucza R.A., et al. 2008. A risk allele for nicotine dependence in CHRNA5 is a protective allele for cocaine dependence. *Biol Psychiatry*. 64(11):922-929.
Guastella, J. et al. 1990. Cloning and Expression of a Rat Brain GABA Transporter. *Science*. 249(4974): 1303-1306.
Gurney A.M. and H.P. Rang. 1984. The channel-blocking action of methonium compounds on rat submandibular ganglion cells. *Br. J. Pharmac*. 82:623-642.
Gyermek. L. 1996. New local anesthetic agents. *Anesthesiology*. 85(1):226-227.
Hachet-Haas, M., N. Converset, O. Marchal, H. Matthes, S. Gioria, J.L. Galzi, and S. Lecat. 2006. FRET and colocalization analyzer—a method to validate measurements of sensitized emission FRET acquired by confocal microscopy and available as an ImageJ Plug-in. *Microsc Res Tech*. 69:941-956.
Hanna, S.T. 2006. Nicotine effect on cardiovascular system and ion channels. *J Cardiovasc Pharmacol*. 47:348-358.
Harris, B.Z. et al. 2001. Mechanism and role of PDZ domains in signaling complex assembly. *J. Cell Science*. 114:3219-3231.
Hastrup, H. et al. 2003. The Human Dopamine Transporter Forms a Tetramer in the Plasma Membrane. *J. Bio Chem*. 278(46):45045-45048.
Herman S.T., Walczak T.S. and Basil C.W. 2001. Distribution of partial seizures during the sleep-wake cycle: differences by seizure onset site. *Neurology* 56(11):1453-1459.
Hess, S.T. et al. 2007. Dynamic clustered distribution of hemagglutinin resolved at 40 nm in living cell membranes discriminates between raft theories. *PNAS*. 104(44):17370-17375.
Holton K.L., M.K. Loder, and H.E. Melikian. 2005. Nonclassical, distinct endocytic signals dictate constitutive and PKC-regulated neurotransmitter transporter internalization. *Nat Neurosci*. 8:881-888.
Hu, J. et al. 2008. Substrate-Mediated Regulation Of γ-Aminobutyric Acid Transporter 1 in Rat Brain. *Neuropharmacology*. 54(2):309-318.
Huang L.Z. and U.H. Winzer-Serhan. 2006. Chronic neonatal nicotine upregulates heteromeric nicotinic acetylcholine receptor binding without change in subunit mRNA expression. *Brain Res*. 1113(1):94-109.
Hung, A.Y., and M. Sheng. 2002. PDZ domains: structural modules for protein complex assembly. *J Biol Chem*. 277:5699-5702.
Hung, R.J., et al. 2008. A susceptibility locus for lung cancer maps to nicotinic acetylcholine receptor subunit genes on 15q25. *Nature*. 452:633-637.
Ibañez-Tallon I., J.M. Miwa, H.L. Wang, N.C. Adams, G.W. Crabtree, S.M. Sine, and N. Heintz. 2002. Novel modulation of neuronal nicotinic acetylcholine receptors by association with the endogenous prototoxin lynx1. *Neuron*. 33:893-903.
Imoukhuede P.I., F.J. Moss, D.J. Michael, R.H. Chow, and H.A. Lester. 2009. Ezrin mediates tethering of the α-aminobutyric acid transporter GAT1 to actin filaments via a C-terminal PDZ-interacting domain. *Biophys J*. 96:2949-2960.
Innocent N., P.D. Livingstone, A. Hone, A. Kimura, T. Young, P. Whiteaker, J.M. McIntosh, and S. Wonnacott. 2008. αConotoxin Arenatus IB[V11I,V16D] is a potent and selective antagonist at rat and human native α7 nicotinic acetylcholine receptors. *J Pharmacol Exp Ther*. 327:529-537.
Jackson K.J., B.R. Martin, J.P. Changeux, and M.I. Damaj. 2008. Differential role of nicotinic acetylcholine receptor subunits in physical and affective nicotine withdrawal signs. *J Pharmacol Exp Ther*. 325:302-312.
Janson A.M., K. Fuxe, E. Sundstrom, I.F. Agnati, and M. Goldstein. 1988. Chronic nicotine treatment partly protects against the 1-methyl-4-phenyl-2,3,6-tetrahydropyridine-induced degeneration of nigrostriatal dopamine neurons in the black mouse. *Acta Physiol Scand*. 132:589-591.
Jares-Erijman E.A., and T.M. Jovin. 2006. Imaging molecular interactions in living cells by FRET microscopy. *Curr Opin Chem Biol*. 10:409-416.
Just, H. et al. 2003. Identification of an Additional Interaction Domain in Transmembrane Domains 11 and 12 That Supports Oligomer Formation in the Human Serotonin Transporter. *J. Bio Chem*. 279(8):6650-6657.
Kanner, B.I. 2002. Transmembrane Domain I of the γ-Aminobutyric Acid Transporter GAT-1 Plays a Crucial Role in the Transition between Cation Leak and Transport Modes. *J. Bio Chem*. 278(6)3705-3712.
Kanner, B.I. 2006. Structure and Function of Sodium-coupled GABA and Glutamate Transporters. *J. Membrane Biol*. 213:89-100.
Kassam S.M., P.M. Herman, N.M. Goodfellow, N.C. Alves, and E.K. Lambe. 2008. Developmental excitation of corticothalamic neurons by nicotinic acetylcholine receptors. *J Neurosci*. 28:8756-8764.
Keller S.H., J. Lindstrom, M. Ellisman, and P. Taylor. 2001. Adjacent basic amino acid residues recognized by the COP I complex and ubiquitination govern endoplasmic reticulum to cell surface trafficking of the nicotinic acetylcholine receptor α-subunit. *J Biol Chem*. 276:18384-18391.
Kerschensteiner, D., F. Soto, and M. Stocker. 2005. Fluorescence measurements reveal stoichiometry of $K^+$ channels formed by modulatory and delayed rectifier α-subunits. *Proc Natl Acad Sci USA*. 102:6160-6165.
Khakh, B.S., J.A. Fisher, R. Nashmi, D.N. Bowser, and H.A. Lester. 2005. An angstrom scale interaction between plasma membrane ATP-gated P2X2 and α4β2 □nicotinic channels measured with FRET and TIRF microscopy. *J Neurosci*. 25:6911-6920.
Khwaja M., A. Mccormack, J.M. Mcintosh, D.A. Di Monte, and M. Quik. 2007. Nicotine partially protects against paraquat-induced nigrostriatal damage in mice; link to α6β2* nAChRs. *J Neurochem*. 100:180-190.
Kilic, F. et al. 2000. Oligomerization of serotonin transporter and its functional consequences. *Proc Natl Acad Sci USA*. 97(7)3106-3111.
Kishi M. and J.H. Steinbach. 2006. Role of the agonist binding site in up-regulation of neuronal nicotinic α4β2 receptors. *Mol Pharmacol*. 70(6):2037-2044.
Klaassen A, Glykys J, Maguire J, Labarca C, Mody I and Boulter J (2006) Seizures and enhanced cortical GABAergic inhibition in two mouse models of human autosomal dominant nocturnal frontal lobe epilepsy. *Proc Natl Acad Sci U S A* 103(50):19152-19157.
Korkhov, V.M. et al. 2004. Oligomerization of the γ-Aminobutyric Acid Transporter-1 Is Driven by an Interplay of Polar and Hydrophobic Interactions in Transmembrane Helix II. *J. Bio Chem*. 279(53):55728-55736.
Kuryatov A., F. Olale, J. Cooper, C. Choi, and J. Lindstrom. 2000. Human α6 AChR subtypes: subunit composition, assembly, and pharmacological responses. *Neuropharmacology*. 39:2570-2590.
Kuryatov A., J. Onksen, and J. Lindstrom. 2008. Roles of accessory subunits in α4β2α5 nicotinic receptors. *Mol Pharmacol*. 74:132-143.

(56) References Cited

OTHER PUBLICATIONS

Kuryatov, A., J. Luo, J. Cooper, and J. Lindstrom. 2005. Nicotine acts as a pharmacological chaperone to up-regulate human α4β2 acetylcholine receptors. *Mol Pharmacol*. 68:1839-1851.

Labarca C., J. Schwarz, P. Deshpande, S. Schwarz, M.W. Nowak, C. Fonck, R. Nashmi, P.Kofuji, H. Dang, W. Shi, M. Fidan, B.S. Khakh, Z. Chen, B.J. Bowers, J. Boulter, J.M. Wehner, and H.A. Lester. 2001. Point mutant mice with hypersensitive α4 nicotinic receptors show dopaminergic deficits and increased anxiety. *Proc Natl Acad Sci U S A*. 98:2786-2791.

Lakowicz, J.R. 2006. Energy Transfer. In Principles of fluorescence spectroscopy. J.R. Lakowicz, editor. Springer Science, New York. 443-506.

Lester, H.A. 1988. Heterologous Expression of Excitability Proteins: Route to More Specific Drugs? *Science*. 241(4869):1057-1063.

Lester, H.A. 1992. The permeation pathway of neurotransmitter-gated ion channels. *Ann. Rev. Biophys. Biomol. Struc*. 21:267-292.

Lester, H.A. 1996. Listening to Neurotransmitter Transporters. *Neuron*. 17:979-990.

Lester, H.A., C. Fonck, A. Tapper, S. McKinney, M. Damaj, S. Balogh, J. Owens, J. Wehner, A. Collins, and C. Labarca. 2003. Hypersensitive knock-in mouse strains identify receptors and pathways for nicotine action. *Current Opinion in Drug Development*. 6:633-639.

Lester, H.A., C. Xiao, R. Srinivasan, C.D. Son, J. Miwa, R. Pantoja, M.R. Banghart, D.A. Dougherty, A.M. Goate, and J.C. Wang. 2009. Nicotine is a selective pharmacological chaperone of acetylcholine receptor number and stoichiometry. Implications for drug discovery. *Aaps J*. 11:167-177.

Levin E.D. 2002. Nicotinic receptor subtypes and cognitive function. *J Neurobiol*. 53:633-640.

Li, M. et al. 2000. An Intermediate State of the γ-Aminobutyric Acid Transporter GAT1 Revealed by Simultaneous Voltage Clamp and Fluorescence. *J. Gen Physiol*. 115:491-508.

Lim T.K., B.A. Macleod, C.R. Ries, and S.K. Schwarz. 2007. The quaternary lidocaine derivative, QX-314, produces long-lasting local anesthesia in animal models in vivo. *Anesthesiology*. 107:305-311.

Lin, D., G.D. Gish, Z. Songyang, and T. Pawson. 1999. The carboxyl terminus of B class ephrins constitutes a PDZ domain binding motif. *J Biol Chem*. 274:3726-3733.

Liu P., H.G. Vikis, D. Wang, Y. Lu, Y. Wang, A.G. Schwartz, S.M. Pinney, P. Yang, M. De Andrade, G.M. Petersen, J.S. Wiest, P.R. Fain, A. Gazdar, C. Gaba, H. Rothschild, D. Mandai, T. Coons, J. Lee, E. Kupert, D. Seminara, J. Minna, J.E. Bailey-Wilson, X. Wu, M.R. Spitz, T. Eisen, R.S. Houlston, C.I. Amos, M.W. Anderson, and M. You. 2008. Familial aggregation of common sequence variants on 15q24-25.1 in lung cancer. *J Nati Cancer Inst*. 100:1326-1330.

Liu Z., A.W. Tearle, Q. Nai, and O.K. Berg. 2005. Rapid activity-driven SNARE-dependent trafficking of nicotinic receptors on somatic spines. *J Neurosci*. 25:1159-1168.

Liu, J-J. et al. 2005. Chronic nicotine exposure during adolescence differentially influences calcium-binding proteins in rat anterior cingulate cortex. *Eur J. Neuroscience*. 22:2462-2474.

Loder, M.K. et al. 2003. The Dopamine Transporter Constitutively Internalizes and Recycles in a Protein Kinase C-regulated Manner in Stably Transfected PC12 Cell Lines. 278(24):22168-22174.

Loo, D. D. F. et al. 2000. Role of Cl$^-$ in Electrogenic Na$^+$-coupled Cotransporters GAT1 and SGLT1. *J. Bio Chem*. 275(48):37414-37422.

Madsen, K.L., T. Beuming, M.Y. Niv, C.W. Chang, K.K. Dev, H. Weinstein, and U. Gether. 2005. Molecular determinants for the complex binding specificity of the PDZ domain in PICK1. *J Biol Chem*. 280:20539-20548.

Mager, S. et al. 1994. Conducting States of a Mammalian Serotonin Transporter. *Neuron*. 12:845-859.

Mamede M., K. Ishizu, M. Ueda, T. Mukai, Y. Iida, H. Kawashima, H. Fukuyama, K. Togashi, and H. Saji. 2007. Temporal change in human nicotinic acetylcholine receptor after smoking cessation: 5IA SPECT study. *J Nucl Med*. 48:1829-1835.

Manley, S. et al. 2008. High-density mapping of single-molecule trajectories with photoactivated localization microscopy. *Nature Methods*. 1176:1-3.

Mansvelder, H.D., and D.S. McGehee. 2000. Long-term potentiation of excitatory inputs to brain reward areas by nicotine. *Neuron*. 27:349-357.

Mao D., D.C. Perry, R.P. Yasuda, B.B. Wolfe, and K.J. Kellar. 2007. The α4β2α5 nicotinic cholinergic receptor in rat brain is resistant to up-regulation by nicotine in vivo. *J Neurochem*. 104:446-456.

Mao D., R.P. Yasuda, H. Fan, B.B. Wolfe, and K.J. Kellar. 2006. Heterogeneity of nicotinic cholinergic receptors in rat superior cervical and nodose Ganglia. *Mol Pharmacol*. 70:1693-1699.

Marchand S., A. Devillers-Thiery, S. Pons, J.P. Changeux, and J. Cartaud. 2002. Rapsyn escorts the nicotinic acetylcholine receptor along the exocytic pathway via association with lipid rafts. *J Neurosci*. 22:8891-8901.

Marks M.J., J.B. Burch, and A.C. Collins. 1983. Effects of chronic nicotine infusion on tolerance development and nicotinic receptors. *J Pharmacol Exp Ther*. 226:817-825.

Marks M.J., J.R. Pauly, S.D. Gross, E.S. Deneris, I. Hermans-Borgmeyer, S.F. Heinemann, and A.C. Collins. 1992. Nicotine binding and nicotinic receptor subunit RNA after chronic nicotine treatment. *J Neurosci*. 12:2765-2784.

Marks M.J., P. Whiteaker, J. Calcaterra, J.A. Stitzel, A.E. Bullock, S.R. Grady, M.R. Picciotto, J.P. Changeux, and A.C. Collins. 1999. Two pharmacologically distinct components of nicotinic receptor-mediated rubidium efflux in mouse brain require the β2 subunit. *J Pharmacol Exp Ther*. 289:1090-1103.

Marshall D.I., P.H. Redfern, and S. Wonnacott. 1997. Presynaptic nicotinic modulation of dopamine release in the three ascending pathways studied by in vivo microdialysis: comparison of naive and chronic nicotine-treated rats. *J Neurochem*. 68:1511-1519.

Martini L. and J.L. Whistler. 2007. The role of mu opioid receptor desensitization and endocytosis in morphine tolerance and dependence. *Curr Opin Neurobiol*. 17:556-564.

Matta S.G.et al. 2007. Guidelines on nicotine dose selection for in vivo research. *Psychopharmacology* (Berl). 190:269-319.

Maus A.D., E.F. Pereira, P.I. Karachunski, R.M. Horton, D. Navaneetham, K. Macklin, W.S. Cortes, E.X. Albuquerque, and B.M. Conti-Fine. 1998. Human and rodent bronchial epithelial cells express functional nicotinic acetylcholine receptors. *Mol Pharmacal*. 54:779-788.

Mazei-Robison, M.S. et al. 2005. Expression studies of naturally occurring human dopamine transporter variants identifies a novel state of transporter inactivation associated with Val382Ala. *Neuropharmacology*. 49:737-749.

McHugh, E.M. et al. 2004. The GABA transporter GAT1 and the MAGUK protein Pals1: interaction, uptake modulation, and coexpression in the brain. *Mol. Cell. Neurosci*. 26:406-417.

Melikian, H.E. et al. 1999. Membrane Trafficking Regulates the Activity of the Human Dopamine Transporter. *J. Neuroscience*. 19(18):7699-7710.

Miranda, M. et al. 2004. Multiple Molecular Determinants in the Carboxyl Terminus Regulate Dopamine Transporter Export from Endoplasmic Reticulum. *J. Bio. Chem*. 279(29):30760-30770.

Miranda, P., D.G. Manso, F. Barros, L. Carretero, T.E. Hughes, C. Alonso-Ron, P. Dominguez, and P. de la Pena. 2008. FRET with multiply labeled HERG K$^+$ channels as a reporter of the in vivo coarse architecture of the cytoplasmic domains. *Biochim Biophys Acta*. 1783:1681-1699.

Miwa J.M., T.R. Stevens, S.L. King, B.J. Caldarone, I. Ibanez-Tallon, C. Xiao, R.M. Fitzsimonds, C. Pavlides, H.A. Lester, M.R. Picciotto, and N. Heintz. 2006. The Prototoxin lynx1 Acts on Nicotinic Acetylcholine Receptors to Balance Neuronal Activity and Survival in Vivo. *Neuron*. 51:587-600.

Morel, E. et al. 2009. Annexin A2-Dependent Polymerization of Actin Mediates Endosome Biogenesis. *Dev. Cell*. 16:445-457.

Moroni, M., R. Zwart, E. Sher, B.K. Cassels, and I. Bermudez. 2006. α4β2 nicotinic receptors with high and low acetylcholine sensitivity: pharmacology, stoichiometry, and sensitivity to long-term exposure to nicotine. *Mol Pharmacol*. 70:755-768.

Moss, F.J., P.I. Imoukhuede, K. Scott, J. Hu, J.L. Jankowsky, M.W. Quick, and H.A. Lester. 2009. GABA transporter function,

(56) References Cited

OTHER PUBLICATIONS oligomerization state, and anchoring: correlates with subcellularly resolved FRET. *J Gen Physiol*. 134:489-521.

Munro, S. 2004. Organelle identity and the organization of membrane traffic. *Nature Cell Biology*. 6(6):469-472.

Nashmi, R., and H. Lester. 2007. Cell autonomy, receptor autonomy, and thermodynamics in nicotine receptor up-regulation. *Biochem Pharmacol*. 74:1145-1154.

Nashmi, R., C. Xiao, P. Deshpande, S. McKinney, S.R. Grady, P. Whiteaker, Q. Huang, T. McClure-Begley, J.M. Lindstrom, C. Labarca, A.C. Collins, M.J. Marks, and H.A. Lester. 2007. Chronic nicotine cell specifically upregulates functional α4* nicotinic receptors: basis for both tolerance in midbrain and enhanced long-term potentiation in perforant path. *J Neurosci*. 27:8202-8218.

Nashmi, R., M.E. Dickinson, S. McKinney, M. Jareb, C. Labarca, S.E. Fraser, and H.A. Lester. 2003. Assembly of α4β2 nicotinic acetylcholine receptors assessed with functional fluorescently labeled subunits: effects of localization, trafficking, and nicotine-induced upregulation in clonal mammalian cells and in cultured midbrain neurons. *J Neurosci*. 23:11554-11567.

Nelson, M.E., A. Kuryatov, C.H. Choi, Y. Zhou, and J. Lindstrom. 2003. Alternate stoichiometries of α4β2 □nicotinic acetylcholine receptors. *Mol Pharmacol*. 63:332-341.

Nguyen, H.N. B.A. Rasmussen, and D.C. Perry. 2004. Binding and functional activity of nicotinic cholinergic receptors in selected rat brain regions are increased following long-term but not short-term nicotine treatment. *J Neurochem*. 90:40-49.

Nguyen, H.N., B.A. Rasmussen, and D.C. Perry. 2003. Subtype-selective up-regulation by chronic nicotine of high-affinity nicotinic receptors in rat brain demonstrated by receptor autoradiography. *J Pharmacol Exp Ther*. 307:1090-1097.

Oldani, A., M. Zucconi, R. Asselta, M. Modugno, M.T. Bonati, L. Dalpra, M. Malcovati, M.L. Tenchini, S. Smirne, and L. Ferini-Strambi. 1998. Autosomal dominant nocturnal frontal lobe epilepsy. A video-polysomnographic and genetic appraisal of 40 patients and delineation of the epileptic syndrome. *Brain*. 121:205-223.

Ormo, M., A.B. Cubitt, K. Kallio, L.A. Gross, R.Y. Tsien, and S.J. Remington. 1996. Crystal structure of the *Aequorea victoria* green fluorescent protein. *Science*. 273:1392-1395.

Orr-Urtreger A., R.S. Broide, M.R. Kasten, H. Dang, J.A. Dani, A.L. Beaudet, and J.W. Patrick. 2000. Mice homozygous for the L250T mutation in the α7 nicotinic acetylcholine receptor show increased neuronal apoptosis and die within 1 day of birth. *J Neurochem*. 74:2154-2166.

Pantoja R., E. Rodriguez, M. Dibas, D. Dougherty, and H. Lester. 2009. Single-molecule imaging of a fluorescent unnatural amino acid incorporated into nicotinic receptors. *Biophys J*. 96: 226-237.

Paroutis P., N. Touret, and S. Grinstein. 2004. The pH of the secretory pathway: measurement, determinants, and regulation. *Physiology (Bethesda)*. 19:207-215.

Partridge, J.G., S. Apparsundaram, G.A. Gerhardt, J. Ronesi, and D.M. Lovinger. 2002. Nicotinic acetylcholine receptors interact with dopamine in induction of striatal long-term depression. *J Neurosci*. 22:2541-2549.

Pauly J.R., M.J. Marks, S.F. Robinson, J.L. Van De Kamp, and A.C. Collins. 1996. Chronic nicotine and mecamylamine treatment increase brain nicotinic receptor binding without changing α4 or β2 mRNA levels. *J Pharmacol Exp Ther*. 278:361-369.

Peng X., V. Gerzanich, R. Anand, P.J. Whiting, and J. Lindstrom. 1994. Nicotine-induced increase in neuronal nicotinic receptors results from a decrease in the rate of receptor turnover. *Mol Pharmacol*. 46:523-530.

Perry D.C., M.I. Davila-Garcia, C.A. Stockmeier, and K.J. Kellar. 1999. Increased nicotinic receptors in brains from smokers: membrane binding and autoradiography studies. *J Pharmacol Exp Ther*. 289:1545-1552.

Phartiyal, P., H. Sale, E.M. Jones, and G.A. Robertson. 2008. Endoplasmic reticulum retention and rescue by heteromeric assembly regulate human ERG 1a/1b surface channel composition. *J Biol Chem*. 283:3702-3707.

Picciotto M.R., N.A. Addy, Y.S. Mineur, and D.H. Brunzell. 2008. It is not "either/or": Activation and desensitization of nicotinic acetylcholine receptors both contribute to behaviors related to nicotine addiction and mood. *Prog Neurobiol*. 84:329-342.

Pollock V.V., T. Pastoor, C. Katnik, J. Cuevas, and L. Wecker. 2008. Cyclic AMP-dependent protein kinase A and protein kinase C phosphorylate α4β2 nicotinic receptor subunits at distinct stages of receptor formation and maturation. *Neuroscience* 158: 1311-1325.

Provini F, Plazzi G, Tinuper P, Vandi S, Lugaresi E and Montagna P (1999) Nocturnal frontal lobe epilepsy. A clinical and polygraphic overview of 100 consecutive cases. *Brain* 122:1017-1031.

Putney J.W., Jr. and J.F. Borzelleca. 1971. On the mechanisms of [$^{14}$C] nicotine distribution in rat submaxillary gland in vitro. *J Pharmacol Exp Ther*. 178:180-191.

Quick M.W. and R.A. Lester. 2002. Desensitization of neuronal nicotinic receptors. *J Neurobiol*. 53:457-478.

Quick M.W. "The Role of SNARE Proteins in Trafficking and Function of Neurotransmitter Transporters" HEP 2006,175, 181-196.

Quik M. 2004. Smoking, nicotine and Parkinson's disease. *Trends Neurosci*. 27:561-568.

Quik M., M. O'neill, and X.A. Perez. 2007. Nicotine neuroprotection against nigrostriatal damage: importance of the animal model. *Trends Pharmacol Sci*. 28:229-235.

Raicu, V. 2007. Efficiency of Resonance Energy Transfer in Homo-Oligomeric Complexes of Proteins. *J Biol Phys*. 33:109-127.

Raicu, V. et al. 2009. Determination of supramolecular structure and spatial distribution of protein complexes in living cells. *Nature Photonics*. 3:107-113.

Ramamoorthy, S. et al. 1998. Phosphorylation and Regulation of Antidepressant-sensitive Serotonin Transporters. *J Bio Chem*. 273(4):2458-2466.

Reiterer, V. et al. 2008. Sec24- and ARFGAP1-Dependent Trafficking of GABA Transporter-1 Is a Prerequisite for Correct Axonal Targeting. *J. Neurosci*. 28(47):12453-12464.

Reith, M.E.A. et al. 2006. The Importance of Company: Na$^+$ and Cl$^-$ Influence Substrate Interaction with SLC6 Transporters and Other Proteins. *HEP*. 175:75-93.

Ritz B., A. Ascherio, H. Checkoway, K.S. Marder, L.M. Nelson, W.A. Rocca, G.W. Ross, D. Strickland, S.K. Van Den Eeden, and J. Gorell. 2007. Pooled analysis of tobacco use and risk of Parkinson disease. *Arch Neurol*. 64:990-997.

Rizzo, M.A., G. Springer, K. Segawa, W.R. Zipfel, and D.W. Piston. 2006. Optimization of pairings and detection conditions for measurement of FRET between cyan and yellow fluorescent proteins. *Microsc Microanal*. 12:238-254.

Rodrigues-Pinguet, N., L. Jia, M. Li, A. Figl, A. Klaassen, A. Truong, H.A. Lester, and B.N. Cohen. 2003. Five ADNFLE mutations reduce the Ca$^{2+}$ dependence of the α4β2 acetylcholine response. *J Physiol*. 550:11-26.

Rodrigues-Pinguet, N.O., T.J. Pinguet, A. Figl, H.A. Lester, and B.N. Cohen. 2005. Mutations linked to autosomal dominant nocturnal frontal lobe epilepsy affect allosteric Ca$^{2+}$ activation of the□ α4β2 nicotinic acetylcholine receptor. *Mol Pharmacol*. 68:487-501.

Roux, A. et al. 2006. GTP-dependent twisting of dynamin implicates constriction and tension in membrane fission. *Nature*. 441:528-531.

Rudnick, G. 2006. Structure/Function Relationships in Serotonin Transporter: New Insights from the Structure of a Bacterial Transporter. *HEP*. 175:59-73.

Ryan R.E., S.A. Ross, J. Drago, and R.E. Loiacono. 2001. Dose-related neuroprotective effects of chronic nicotine in 6-hydroxydopamine treated rats, and loss of neuroprotection in α4 nicotinic receptor subunit knockout mice. *Br J Pharmacal*. 132:1650-1656.

Ryvlin, P. et al. 2006. Nocturnal Frontal Lobe Epilepsy. *Epilepsia*. 47(suppl 2):83-86.

Saccone S.F., A.L. Hinrichs, N.L. Saccone, G.A. Chase, K. Konvicka, P.A. Madden, N. Breslau, E.O. Johnson, D. Hatsukami, O.F. Pomerleau, G.E. Swan, A.M. Goate, J. Rutter, S. Bertelsen, L. Fox, D. Fugman, N.G. Martin, G.W. Montgomery, J.C. Wang, D.G. Ballinger, J.P. Rice, and L.J. Bierut. 2006. Cholinergic nicotinic receptor genes implicated in a nicotine dependence association study targeting 348 candidate genes with 3713 SNPs. *Human Molecular Genetics*. 16:36-49.

(56) References Cited

OTHER PUBLICATIONS

Salas R., F. Pieri, and M. De Biasi. 2004. Decreased signs of nicotine withdrawal in mice null for the β4 nicotinic acetylcholine receptor subunit. J Neurosci. 24:10035-10039.

Salas et al. "Altered Anxiety-Related Responses in Mutant Mice Lacking the β4 Subunit of the Nicotinic Receptor" *J. Neurosci.* 2003, 23, 6255-6263.

Sallette J., S. Bohler, P. Benoit, M. Soudant, S. Pons, N. Le Novere, J.P. Changeux, and P.J. Carringer. 2004. An extracellular protein microdomain controls up-regulation of neuronal nicotinic acetylcholine receptors by nicotine. *J Biol Chem.* 279:18767-18775.

Sallette, J., S. Pons, A. Devillers-Thiery, M. Soudant, L. Prado de Carvalho, J.P. Changeux, and P.J. Corringer. 2005. Nicotine upregulates its own receptors through enhanced intracellular maturation. *Neuron.* 46:595-607.

Schapira, A.H., E. Bezard, J. Brotchie, F. Calon, G.L. Collingridge, B. Ferger, B. Hengerer, E. Hirsch, P. Jenner, N. Le Novere, J.A. Obeso, M.A. Schwarzschild, U. Spampinato, and G. Davidai. 2006. Novel pharmacological targets for the treatment of Parkinson's disease. *Nat Rev Drug Discov.* 5:845-854.

Scheffer IE, Bhatia KP, Lopes-Cendes I, Fish DR, Marsden CD, Andermann F, Andermann E, Desbiens R, Cendes F, Manson JI and et al. (1994) Autosomal dominant frontal epilepsy misdiagnosed as sleep disorder. *Lancet* 343(8896):515-517.

Scheffer, I.E., K.P. Bhatia, I. Lopes-Cendes, D.R. Fish, C.D. Marsden, E. Andermann, F. Andermann, R. Desbiens, D. Keene, F. Cendes, and et al. 1995. Autosomal dominant nocturnal frontal lobe epilepsy. A distinctive clinical disorder. *Brain.* 118:61-73.

Schmid, J.A. 2001. Oligomerization of the Human Serotonin Transporter and of the Rat GABA Transporter 1 Visualized by Fluorescence Resonance Energy Transfer Microscopy in Living Cells. *J. Bio Chem.* 276(6):3805-3810.

Scholze, P., M. Freissmuth, and H.H. Sitte. 2002. Mutations within an intramembrane leucine heptad repeat disrupt oligomer formation of the rat GABA transporter 1. *J Biol Chem.* 277:43682-43690.

Schwartz, R.D., and K.J. Kellar. 1983. Nicotinic cholinergic receptor binding sites in the brain: regulation in vivo. *Science.* 220:214-216.

Scott, D.B., T.A. Blanpied, and M.D. Ehlers. 2003. Coordinated PKA and PKC phosphorylation suppresses RXR-mediated ER retention and regulates the surface delivery of NMDA receptors. *Neuropharmacology.* 45:755-767.

Scott, D.B., T.A. Blanpied, G.T. Swanson, C. Zhang, and M.D. Ehlers. 2001. An NMDA receptor ER retention signal regulated by phosphorylation and alternative splicing. *J Neurosci.* 21:3063-3072.

Scott, W.K., F. Zhang, J.M. Stajich, B.L. Scott, M.A. Stacy, and J.M. Vance. 2005. Family-based case-control study of cigarette smoking and Parkinson disease. *Neurology.* 64:442-447.

Sekar, R.B., and A. Periasamy. 2003. Fluorescence resonance energy transfer (FRET) microscopy imaging of live cell protein localizations. *J Cell Biol.* 160:629-633.

Sekhon H.S., P. Song, Y. Jia, J. Lindstrom, and E.R. Spindel. 2005. Expression of lynx1 in developing lung and its modulation by prenatal nicotine exposure. *Cell Tissue Res.* 320:287-297.

Shaner, N.C., P.A. Steinbach, and R.Y. Tsien. 2005. A guide to choosing fluorescent proteins. *Nat Methods.* 2:905-909.

Shaner, N.C., R.E. Campbell, P.A. Steinbach, B.N. Giepmans, A.E. Palmer, and R.Y. Tsien. 2004. Improved monomeric red, orange and yellow fluorescent proteins derived from *Discosoma* sp. red fluorescent protein. *Nat Biotechnol.* 22:1567-1572.

Shao XM, Tan W, Xiu J, Puskar N, Fonck C, Lester HA and Feldman JL (2008) α4* nicotinic receptors in preBötzinger complex mediate cholinergic/nicotinic modulation of respiratory rhythm. *J Neurosci* 28(2):519-528.

Sheng, M., and C. Sala. 2001. PDZ domains and the organization of supramolecular complexes. *Annu Rev Neurosci.* 24:1-29.

Sherva R., K. Wilhelmsen, C.S. Pomerleau, S.A. Chasse, J.P. Rice, S.M. Snedecor, L.J. Bierut, R.J. Neuman, and O.F. Pomerleau. 2008. Association of a single nucleotide polymorphism in neuronal acetylcholine receptor subunit as (CHRNA5) with smoking status and with 'pleasurable buzz' during early experimentation with smoking. *Addiction.* 103:1544-1552.

Skok M., R. Grailhe, and J.P. Changeux. 2005. Nicotinic receptors regulate B lymphocyte activation and immune response. *Eur J Pharmacol.* 517:246-251.

Skok et al. "The role of nicotinic acetylcholine receptors in lymphocyte development" *J. Neuroimmunol.* 2006, 171, 86-98.

Son, C.D., F.J. Moss, B.N. Cohen, and H.A. Lester. 2009. Nicotine normalizes intracellular subunit stoichiometry of nicotinic receptors carrying mutations linked to autosomal dominant nocturnal frontal lobe epilepsy. *Mol Pharmacol.* 75:1137-1148.

Song P., H.S. Sekhon, X.W. Fu, M. Maier, Y. Jia, J. Duan, B.J. Proskosil, C. Gravett, J. Lindstrom, G.P. Mark, S. Saha, and E.R. Spindel. 2008. Activated cholinergic signaling provides a target in squamous cell lung carcinoma. *Cancer Res.* 68:4693-4700.

Soragana, A. et al. 2005. Functionally independent subunits in the oligomeric structure of the GABA cotransporter rGAT1. *Cell Mol life Sci.* 62:2877-2885.

Sorkina, T. et al. 2003. Oligomerization of Dopamine Transporters Visualized in Living Cells by Fluorescence Resonance Energy Transfer Microscopy. *J Bio Chem.* 278(30):28274-28283.

Spudich, G., X.M. Fernandez-Suarez, and E. Birney. 2007. Genome browsing with Ensembl: a practical overview. *Brief Funct Genomic Proteomic.* 6:202-219.

Staley J.K., S. Krishnan-Sarin, K.P. Cosgrove, E. Krantzler, E. Frohlich, E. Perry, J.A. Dubin, K. Estok, E. Brenner, R.M. Baldwin, G.D. Tamagnan, J.P. Seibyl, P. Jatlow, M.R. Picciotto, E.D. London, S. O'malley, and C.H. Van Dyck. 2006. Human tobacco smokers in early abstinence have higher levels of β2* nicotinic acetylcholine receptors than nonsmokers. *J Neurosci.* 26:8707-8714.

Staruschenko, A., E. Adams, R.E. Booth, and J.D. Stockand. 2005. Epithelial $Na^+$ channel subunit stoichiometry. *Biophys J.* 88:3966-3975.

Staruschenko, A., J.L. Medina, P. Patel, M.S. Shapiro, R.E. Booth, and J.D. Stockand. 2004. Fluorescence resonance energy transfer analysis of subunit stoichiometry of the epithelial $Na^+$ channel. *J Biol Chem.* 279:27729-27734.

Steinlein O.K., J.C. Mulley, P. Propping, R.H. Wallace, H.A. Phillips, G.R. Sutherland, I.E. Scheffer, and S.F. Berkovic. 1995. A missense mutation in the neuronal nicotinic acetylcholine receptor α4 subunit is associated with autosomal dominant nocturnal frontal lobe epilepsy. *Nat Genet.* 11:201-203.

Steinlein, O.K., A. Magnusson, J. Stoodt, S. Bertrand, S. Weiland, S.F. Berkovic, K.O. Nakken, P. Propping, and D. Bertrand. 1997. An insertion mutation of the CHRNA4 gene in a family with autosomal dominant nocturnal frontal lobe epilepsy. *Hum Mol Genet.* 6:943-947.

Steppuhn A. and I.T. Baldwin. 2007. Resistance management in a native plant: nicotine prevents herbivores from compensating for plant protease inhibitors. *Ecol Lett.* 10:499-511.

Steppuhn A., K. Gase, B. Krock, R. Halitschke, and I.T. Baldwin. 2004. Nicotine's defensive function in nature. *PLoS Biol.* 2(8):E217.

Stevens V., L. Bierut, J. Talbot, W. Jc, J. Sun, A. Hinrichs, M. Thun, A. Goate, and E. Calle. 2008. Nicotinic Receptor Gene Variants Influence Susceptibility to Heavy Smoking. *Cancer Epidemiol Biomarkers Prev.* 17(12):3517-3525.

Stewart, T.B., and O.M. Hale. 1988. Losses to internal parasites in swine production. *J Anim Sci.* 66:1548-1554.

Tadross, M.R. et al. 2008. Robust approaches to quantitative ratiometric FRET imaging of CFP/YFP fluorophores under confocal microscopy. *J. Microscopy.* 223:192-204.

Taglialatela M., A.M. Vandongen, J.A. Drewe, R.H. Joho, A.M. Brown, and G.E. Kirsch. 1991. Patterns of internal and external tetraethylammonium block in four homologous $K^+$ channels. *Mol Pharmacol.* 40:299-307.

Tanner, C.M., S.M. Goldman, D.A. Aston, R. Ottman, J. Ellenberg, R. Mayeux, and J.W. Langston. 2002. Smoking and Parkinson's disease in twins. *Neurology.* 58:581-588.

Tapia, L., A. Kuryatov, and J. Lindstrom. 2007. Ca2+ permeability of the (α4)3(β2)2 stoichiometry greatly exceeds that of (α4)2(β2)3 human acetylcholine receptors. *Mol Pharmacol.* 71:769-776.

(56) References Cited

OTHER PUBLICATIONS

Tapper A., S. Mckinney, M. Marks, and H. Lester. 2007. Nicotine responses in hypersensitive and knockout α4 mice account for tolerance to both hypothermia and locomotor suppression in wild-type mice. *Physiol Genomics.* 3:422-428 (2007).
Tapper, A., S. McKinney, R. Nashmi, J. Schwarz, P. Deshpande, C. Labarca, P. Whiteaker, A. Collins, and H. Lester. 2004. Nicotine activation of α4* receptors: sufficient for reward, tolerance and sensitization. *Science.* 306:1029-1032.
Taunton, J. et al. 2000. Actin-dependent Propulsion of Endosomes and Lysosomes by Recruitment of N-WASP. *J. Cell Bio.* 148(3)519-530.
Teper, Y., D. Whyte, E. Cahir, H.A. Lester, S.R. Grady, M.J. Marks, B.N. Cohen, C. Fonck, T. McClure-Begley, J.M. McIntosh, C. Labarca, A. Lawrence, F. Chen, I. Gantois, P.J. Davies, S. Petrou, M. Murphy, J. Waddington, M.K. Horne, S.F. Berkovic, and J. Drago. 2007. Nicotine-induced dystonic arousal complex in a mouse line harboring a human autosomal dominant nocturnal frontal lobe epilepsy mutation. *J. Neurosci.* 27:10128-10142.
Thorgeirsson T.E. et al. 2008. A variant associated with nicotine dependence, lung cancer and peripheral arterial disease. *Nature.* 452:638-642.
Tisdale, E.J. et al. 1992. GTP-Binding Mutants of Rab1 and Rab2 are Potent Inhibitors of Vesicular Transport from the Endoplasmic Reticulum to the Golgi Complex. *J. Cell Bio.* 119(4):749-761.
Tokunaga, M. et al. 2008. Highly inclined thin illumination enables clear single-molecule imaging in cells. *Nature Methods.* 5(2):159-161.
Torres, G.E. 2003 Oligomerization and Trafficking of the Human Dopamine Transporter. *J. Bio Chem.* 278(4):2731-2739.
Torres, R., B.L. Firestein, H. Dong, J. Staudinger, E.N. Olson, R.L. Huganir, D.S. Bredt, N.W. Gale, and G.D. Yancopoulos. 1998. PDZ proteins bind, cluster, and synaptically colocalize with Eph receptors and their ephrin ligands. *Neuron.* 21:1453-1463.
Touroutine, D., R.M. Fox, S.E. Von Stetina, A. Burdina, D.M. Miller, 3rd, and J.E. Richmond. 2005. acr-16 encodes an essential subunit of the levamisole-resistant nicotinic receptor at the *Caenorhabditis elegans* neuromuscular junction. *J Biol Chem.* 280:27013-27021.
Tumkosit P., A. Kuryatov, J. Luo, and J. Lindstrom. 2006. β3 subunits promote expression and nicotine- induced up-regulation of human nicotinic α6* nicotinic acetylcholine receptors expressed in transfected cell lines. Mol Pharmacol. 70:1358-1368.
Unwin, N. 2005. Refined structure of the nicotinic acetylcholine receptor at 4Å resolution. *J Mol Biol.* 346:967-989.
Vallejo, Y.F., B. Buisson, D. Bertrand, and W.N. Green. 2005. Chronic nicotine exposure upregulates nicotinic receptors by a novel mechanism. *J Neurosci.* 25:5563-5572.
Vincler, M.A., and J.C. Eisenach. 2005. Knock down of the α5 nicotinic acetylcholine receptor in spinal nerve-ligated rats alleviates mechanical allodynia. *Pharmacol Biochem Behav.* 80:135-143.
Visanji N.P., S.N. Mitchell, M.J. O'neill, and S. Duty. 2006. Chronic pre-treatment with nicotine enhances nicotine-evoked striatal dopamine release and α6 and β3 nicotinic acetylcholine receptor subunit mRNA in the substantia nigra pars compacta of the rat. *Neuropharmacology.* 50:36-46.
Wallrabe, H., and A. Periasamy. 2005. Imaging protein molecules using FRET and FLIM microscopy. *Curr Opin Biotechnol.* 16:19-27.
Wang, D. et al. 2005. Trafficking of the Plasma Membrane γ-Aminobutyric Acid Transporter GAT1. *J. Bio Chem.* 280(19):18703-18709.
Wang, F., M.E. Nelson, A. Kuryatov, F. Olale, J. Cooper, K. Keyser, and J. Lindstrom. 1998. Chronic nicotine treatment up-regulates human a3P2 but not α3β4 acetylcholine receptors stably transfected in human embryonic kidney cells. *J Biol Chem.* 273:28721-28732.
Wang, G.K., C. Quan, M. Vladimirov, W.M. Mok, and J.G. Thalhammer. 1995. Quaternary ammonium derivative of lidocaine as a long-acting local anesthetic. *Anesthesiology.* 83:1293-1301.
Wang, J., R. Grucza, C. Cruchaga, A. Hinrichs, S. Bertelsen, J. Budde, L. Fox, E. Goldstein, O. Reyes, N. Saccone, S. Saccone, X. Xuei, K. Bucholz, S. Kuperman, J. Nurnberger Jr, J. Rice, M. Schuckit, J. Tischfield, V. Hesselbrock, B. Porjesz, H. Edenberg, L. Bierut, and A. Goate. 2008. Genetic variation in the CHRNA5 gene affects mRNA levels and is associated with risk for alcohol dependence. *Mol Psychiatry.* 14: 501-510.
Wang, N., A. Orr-Urtreger, J. Chapman, R. Rabinowitz, R. Nachman, and A.D. Korczyn. 2002. Autonomic function in mice lacking α5 neuronal nicotinic acetylcholine receptor subunit. *J Physiol.* 542:347-354.
Wathey J.C., M.N. Nass, and H.A. Lester. 1979. Numerical reconstruction of the quanta event at nicotinic synapses. *Biophys. J.* 27:145-164.
Weiss R.B., T.B. Baker, D.S. Cannon, A. Von Niederhausern, D.M. Dunn, N. Matsunami, N.A. Singh, L. Baird, H. Coon, W.M. Mcmahon, M.E. Piper, M.C. Fiore, M.B. Scholand, J.E. Connett, R.E. Kanner, L.C. Gahring, S.W. Rogers, J.R. Hoidal, and M.F. Leppert. 2008. A candidate gene approach identifies the CHRNA5-A3-B4 region as a risk factor for age-dependent nicotine addiction. *PLoS Genet.* 4:e1000125.
Whiteaker, P., C.G. Sharples, and S. Wonnacott. 1998. Agonist-induced up-regulation of α4β2 nicotinic acetylcholine receptors in M10 cells: pharmacological and spatial definition. *Mol Pharmacol.* 53:950-962.
Whitworth, T.L. et al. 2001. Substrate-induced Regulation of γ-Aminobutyric Acid Transporter Trafficking Requires Tyrosine Phosphorylation. *J. Bio Chem.* 276:46:42932-42937.
Williamson, S.M. et al. 2007. The cys-loop ligand-gated ion channel gene family of *Brugia malayi* and *Trichinella spiralis*: a comparison with *Caenorhabditis elegans*. *Invert Neurosci.* 7:219-226.
Williamson, S.M. et al. 2009. The nicotinic acetylcholine receptors of the parasitic nematode *Ascaris suum*: formation of two distinct drug targets by varying the relative expression levels of two subunits. *PLoS Pathog.* 5:e1000517.
Willoughby, J.O., K.J. Pope, and V. Eaton. 2003. Nicotine as an antiepileptic agent in ADNFLE: an N-of-one study. *Epilepsia.* 44:1238-1240.
Wimmer, V.C., H.A. Lester, and S. Petrou. 2009. Ion channel mutations in familial epilepsy. In Encyclopedia of Basic Epilepsy Research. P.A. Schwartzkroin, editor. Elsevier, Oxford. pp. 651-658.
Wirdefeldt, K. M. Gatz, Y. Pawitan, and N.L. Pedersen. 2005. Risk and protective factors for Parkinson's disease: a study in Swedish twins. *Ann Neurol.* 57:27-33.
Wiseman RL, Powers ET, Buxbaum JN, Kelly JW and Balch WE (2007) An adaptable standard for protein export from the endoplasmic reticulum. *Cell* 131(4):809-821.
Wong, J.Y., S.A. Ross, C. McColl, J.S. Massalas, E. Powney, D.I. Finkelstein, M. Clark, M.K. Horne, S.F. Berkovic, and J. Drago. 2002. Proconvulsant-induced seizures in α4 nicotinic acetylcholine receptor subunit knockout mice. *Neuropharmacology.* 43:55-64.
Wu, W.K., and C.H. Cho. 2004. The pharmacological actions of nicotine on the gastrointestinal tract. *J Pharmacol Sci.* 94:348-358.
www.Clinicaltrials.gov. A service of the U.S. National Institutes of Health. Accessed: Jun. 21, 2012.
Xia, Z., and Y. Liu. 2001. Reliable and global measurement of fluorescence resonance energy transfer using fluorescence microscopes. *Biophys J.* 81:2395-2402.
Xiao, Y., and K.J. Kellar. 2004. The comparative pharmacology and up-regulation of rat neuronal nicotinic receptor subtype binding sites stably expressed in transfected mammalian cells. *J Pharmacol Exp Ther.* 310:98-107.
Xu J., Y. Zhu, and S.F. Heinemann. 2006. Identification of sequence motifs that target neuronal nicotinic receptors to dendrites and axons. *J Neurosci.* 26:9780-9793.
Yamashita, A., S.K. Singh, T. Kawate, Y. Jin, and E. Gouaux. 2005. Crystal structure of a bacterial homologue of $Na^+/Cl^-$-dependent neurotransmitter transporters. *Nature.* 437:215-223.
Zacharias, D.A., J.D. Violin, A.C. Newton, and R.Y. Tsien. 2002. Partitioning of lipid-modified monomeric GFPs into membrane microdomains of live cells. *Science.* 296:913-916.
Zahniser, N.R. et al. 2001. Chronic and acute regulation of $Na^+/Cl^-$-dependent neurotransmitter transporters: drugs, substrates, presynaptic receptors, and signaling systems, *Pharma & Therap.* 92:21-55.

(56) References Cited

OTHER PUBLICATIONS

Zhang, Y.W., and G. Rudnick. 2006. The cytoplasmic substrate permeation pathway of serotonin transporter. *J Biol Chem*. 281:36213-36220.

Zheng, J. et al. 2002. Rod cyclic nucleotide-gated channels have a stoichiometry of three CNGA1 subunits and one CNGB1 subunit. *Neuron*. 36:891-896.

Zheng, J. et al. 2004. Stoichiometry and assembly of olfactory cyclic nucleotide-gated channels. *Neuron*. 42:411-421.

Zhou Y., M.E. Nelson, A. Kuryatov, C. Choi, J. Cooper, and J. Lindstrom. 2003. Human α4β2 acetylcholine receptors formed from linked subunits. *J Neurosci*. 23:9004-9015.

Zoli, M., M. Moretti, A. Zanardi, J.M. McIntosh, F. Clementi, and C. Gotti. 2002. Identification of the nicotinic receptor subtypes expressed on dopaninergic terminals in the rat striatum. *J. Neurosci*. 22:8785-8789.

Zucconi M and Ferini-Strambi L (2000) NREM parasornnias: arousal disorders and differentiation from nocturnal frontal lobe epilepsy. *Clin Neurophysiol* 111 Suppl 2:S129-135.

Zwart R. and H.P. Vijverberg. 1998. Four pharmacologically distinct subtypes of α4β2 nicotinic acetylcholine receptor expressed in *Xenopus laevis* oocytes. *Mol Pharmacol*. 54:1124-1131.

Zwart, R., L.M. Broad, Q. Xi, M. Lee, M. Moroni, I. Bermudez, and E. Sher. 2006. 5-I A-85380 and TC-2559 differentially activate heterologously expressed α4αβ2 nocotinic receptors. *Eur J Pharmacol*. 539:10-17.

Oldani, A. et al. (1996) Autosomal dominant nocturnal frontal lobe epilepsy: electroclinical picture. Epilepsia, 37(1), pp. 964-976.

Archived image of Clinical Trials.gov, "http://www.clinicaltrials.gov/," from Jun. 4, 2013.

Archived image of BioMart, "http://www.ebi.ac.uk/uniprot/biomart/martview/68623b2202c03382db02473f8077fead", from Jun. 4, 2013.

\* cited by examiner

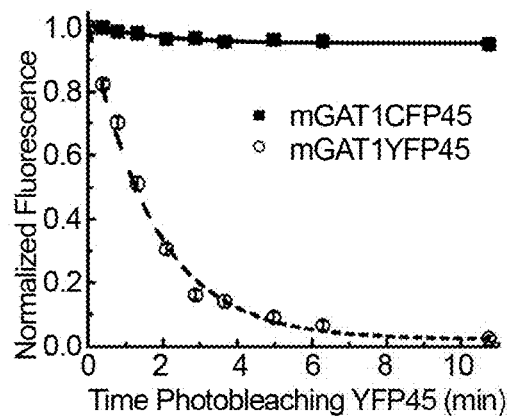
FIG. 13A
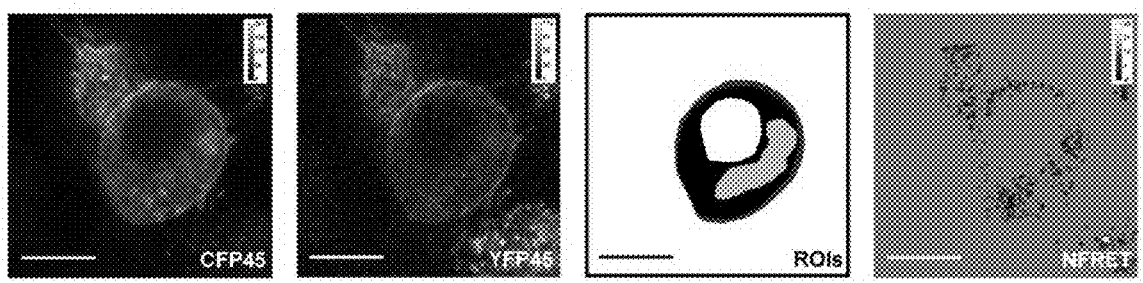
FIG. 13B
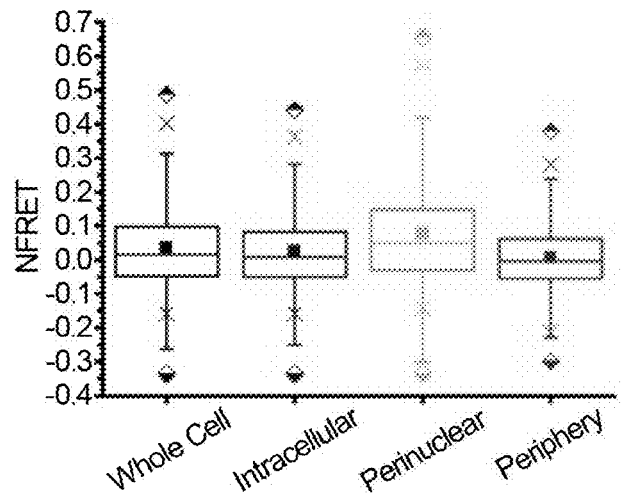
FIG. 13C
| mGAT1XFP45 | Mean 1 | % | Mean 2 | % |
|---|---|---|---|---|
| Whole Cell | -0.03 ± 0.01 | 49% | 0.09 ± 0.02 | 51% |
| Intracellular | -0.04 ± 0.01 | 46% | 0.07 ± 0.02 | 54% |
| Perinuclear | -0.04 ± 0.01 | 26% | 0.08 ± 0.07 | 74% |
| Periphery | -0.05 ± 0.01 | 14% | 0.01 ± 0.02 | 86% |
FIG. 13D

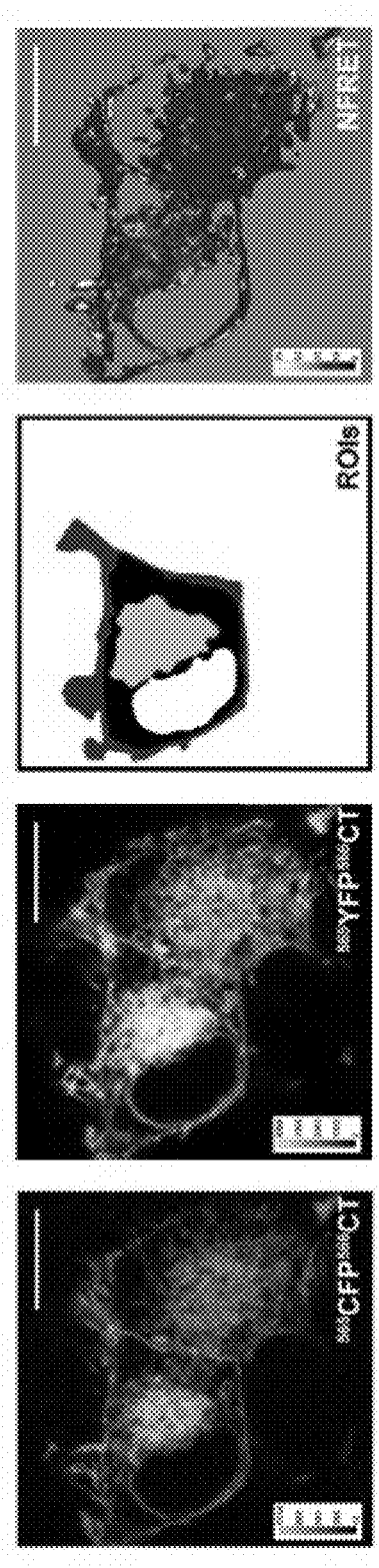
FIG. 14A
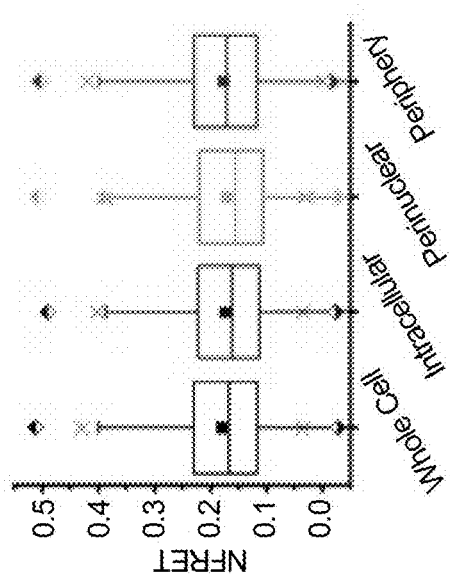
FIG. 14B
| mGAT1[565]XFP[566]CT | Mean 1 | % | Mean 2 | % |
|---|---|---|---|---|
| Whole Cell | 0.14 ± 0.01 | 60 | 0.24 ± 0.04 | 40 |
| Intracellular | 0.13 ± 0.01 | 63 | 0.24 ± 0.03 | 37 |
| Perinuclear | 0.12 ± 0.01 | 52 | 0.22 ± 0.02 | 48 |
| Periphery | 0.17 ± 0.01 | 40 | 0.21 ± 0.03 | 60 |
FIG. 14C

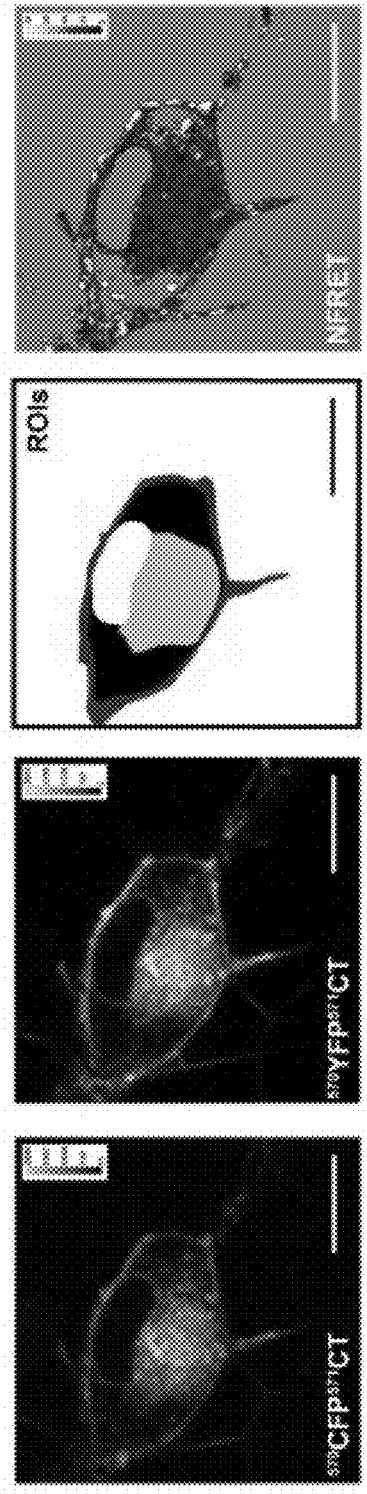
FIG. 14E
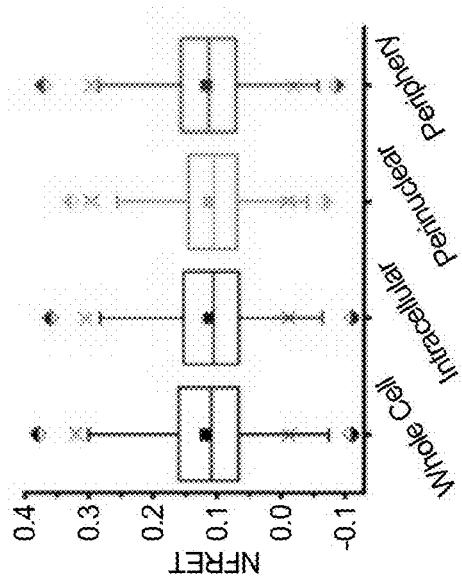
| mGAT1⁵⁷⁰XFP⁵⁷¹CT | Mean 1 | % | Mean 2 | % |
|---|---|---|---|---|
| Whole Cell | 0.09 + 0.01 | 66 | 0.15 + 0.04 | 34 |
| Intracellular | 0.08 + 0.01 | 66 | 0.17 + 0.03 | 34 |
| Perinuclear | 0.09 + 0.01 | 59 | 0.14 + 0.09 | 41 |
| Periphery | 0.11 + 0.01 | 98 | 0.29 + 0.09 | 2 |
FIG. 14G
FIG. 14F

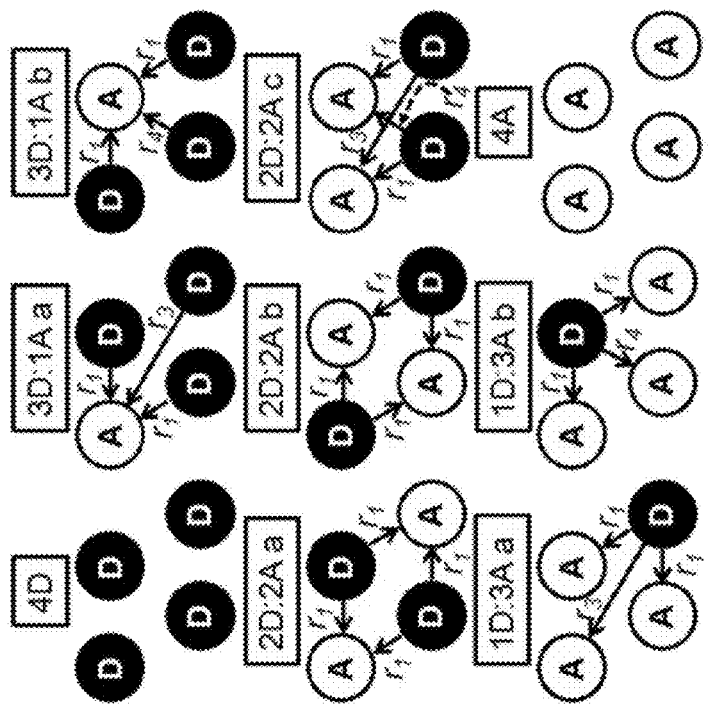

Rhomboid Tetramer $$E_{(3D:1A)a} = \frac{1}{3}\left[\frac{(R_0/r_1)^6}{1+(R_0/r_1)^6} + \frac{(R_0/r_1)^6}{1+(R_0/r_1)^6} + \frac{(R_0/r_3)^6}{1+(R_0/r_3)^6}\right]$$

$$E_{(3D:1A)b} = \frac{1}{3}\left[\frac{(R_0/r_1)^6}{1+(R_0/r_1)^6} + \frac{(R_0/r_3)^6}{1+(R_0/r_3)^6} + \frac{(R_0/r_4)^6}{1+(R_0/r_4)^6}\right]$$

$$E_{(2D:2A)a} = \frac{R_0^6(1/r_1^6 + 1/r_1^6)}{1+R_0^6(1/r_1^6 + 1/r_1^6)}$$

$$E_{(2D:2A)b} = \frac{R_0^6(1/r_1^6 + 1/r_3^6)}{1+R_0^6(1/r_1^6 + 1/r_3^6)}$$

$$E_{(2D:2A)c} = \frac{1}{2}\left[\frac{R_0^6(1/r_1^6 + 1/r_3^6)}{1+R_0^6(1/r_1^6 + 1/r_3^6)} + \frac{R_0^6(1/r_1^6 + 1/r_4^6)}{1+R_0^6(1/r_1^6 + 1/r_4^6)}\right]$$

$$E_{(1D:3A)a} = \frac{R_0^6(2/r_1^6 + 1/r_3^6)}{1+R_0^6(2/r_1^6 + 1/r_3^6)}$$

$$E_{(1D:3A)b} = \frac{R_0^6(2/r_1^6 + 1/r_4^6)}{1+R_0^6(2/r_1^6 + 1/r_4^6)}$$

FIG. 15C

SEQUENCE LISTING

<160> NUMBER OF SEQ ID NOS: 26

<210> SEQ ID NO 1
<211> LENGTH: 15
<212> TYPE: PRT
<213> ORGANISM: Artificial Sequence
<220> FEATURE:
<223> OTHER INFORMATION: Portion of mGAT10GFP

<400> SEQUENCE: 1

-continued

```
Thr Ala Ala Gly Ile Thr His Gly Met Asp Glu Leu Tyr Lys Ile
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Portion of mGAT10XFP

<400> SEQUENCE: 2

Thr Ala Ala Gly Ile Thr His Gly Met Asp Glu Leu Tyr Lys Ile
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Portion of mGAT1XFP*

<400> SEQUENCE: 3

Thr Ala Ala Gly Ile Thr Leu Gly Met Asp Glu Leu Tyr Lys Val
1               5                   10                  15

<210> SEQ ID NO 4
<211> LENGTH: 17
<212> TYPE: PRT
<213> ORGANISM: Artificial Sequence
<220> FEATURE:
<223> OTHER INFORMATION: Portion of mGAT1XFP3

<400> SEQUENCE: 4

Thr Ala Ala Gly Ile Thr Leu Gly Met Asp Glu Leu Tyr Lys Ala Tyr
1               5                   10                  15

Ile

<210> SEQ ID NO 5
<211> LENGTH: 22
<212> TYPE: PRT
<213> ORGANISM: Artificial Sequence
<220> FEATURE:
<223> OTHER INFORMATION: Portion of mGAT1XFP8

<400> SEQUENCE: 5

Thr Ala Ala Gly Ile Thr Leu Gly Met Asp Glu Leu Tyr Lys Ser Thr
1               5                   10                  15

Ser Lys Glu Ala Tyr Ile
            20

<210> SEQ ID NO 6
<211> LENGTH: 34
<212> TYPE: PRT
<213> ORGANISM: Artificial Sequence
<220> FEATURE:
<223> OTHER INFORMATION: Portion of mGAT1XFP20

<400> SEQUENCE: 6

Thr Ala Ala Gly Ile Thr Leu Gly Met Asp Glu Leu Tyr Lys Pro Glu
1               5                   10                  15

Asn Gly Pro Glu Gln Pro Gln Ala Gly Ser Ser Thr Ser Lys Glu Ala
            20                  25                  30

Tyr Ile
```

```
<210> SEQ ID NO 7
<211> LENGTH: 42
<212> TYPE: PRT
<213> ORGANISM: Artificial Sequence
<220> FEATURE:
<223> OTHER INFORMATION: Portion of mGAT1XFP28

<400> SEQUENCE: 7

Thr Ala Ala Gly Ile Thr Leu Gly Met Asp Glu Leu Tyr Lys Gln Pro
1               5                   10                  15

Ser Glu Asp Ile Val Arg Pro Glu Asn Gly Pro Glu Gln Pro Gln Ala
            20                  25                  30

Gly Ser Ser Thr Ser Lys Glu Ala Tyr Ile
        35                  40

<210> SEQ ID NO 8
<211> LENGTH: 59
<212> TYPE: PRT
<213> ORGANISM: Artificial Sequence
<220> FEATURE:
<223> OTHER INFORMATION: Portion of mGAT1XFP45

<400> SEQUENCE: 8

Thr Ala Ala Gly Ile Thr Leu Gly Met Asp Glu Leu Tyr Lys Met Phe
1               5                   10                  15

Leu Ala Leu Lys Gly Ser Leu Lys Gln Arg Ile Gln Val Met Val Gln
            20                  25                  30

Pro Ser Glu Asp Ile Val Arg Pro Glu Asn Gly Pro Glu Gln Pro Gln
        35                  40                  45

Ala Gly Ser Ser Thr Ser Lys Glu Ala Tyr Ile
    50                  55

<210> SEQ ID NO 9
<211> LENGTH: 47
<212> TYPE: PRT
<213> ORGANISM: Artificial Sequence
<220> FEATURE:
<223> OTHER INFORMATION: Portion of mGAT1

<400> SEQUENCE: 9

Ala Tyr Met Phe Leu Thr Leu Lys Gly Ser Leu Lys Gln Arg Leu Gln
1               5                   10                  15

Val Met Ile Gln Pro Ser Glu Asp Ile Val Arg Pro Glu Asn Gly Pro
            20                  25                  30

Glu Gln Pro Gln Ala Gly Ser Ser Ala Ser Lys Glu Ala Tyr Ile
        35                  40                  45

<210> SEQ ID NO 10
<211> LENGTH: 18
<212> TYPE: PRT
<213> ORGANISM: Artificial Sequence
<220> FEATURE:
<223> OTHER INFORMATION: Portion of mGAT1565XFP566CT

<400> SEQUENCE: 10

Ala Tyr Met Phe Leu Thr Leu Lys Gly Ser Leu Lys Gln Arg Met Val
1               5                   10                  15

Ser Lys

<210> SEQ ID NO 11
<211> LENGTH: 37
<212> TYPE: PRT
<213> ORGANISM: Artificial Sequence
<220> FEATURE:
```

<223> OTHER INFORMATION: Portion of mGAT1565XFP566CT

<400> SEQUENCE: 11

Glu Leu Tyr Lys Leu Gln Val Met Ile Gln Pro Ser Glu Asp Ile Val
1               5                   10                  15

Arg Pro Glu Asn Gly Pro Glu Gln Pro Gln Ala Gly Ser Ser Ala Ser
            20                  25                  30

Lys Glu Ala Tyr Ile
        35

<210> SEQ ID NO 12
<211> LENGTH: 23
<212> TYPE: PRT
<213> ORGANISM: Artificial Sequence
<220> FEATURE:
<223> OTHER INFORMATION: Portion of mGAT1570XFP571CT

<400> SEQUENCE: 12

Ala Tyr Met Phe Leu Thr Leu Lys Gly Ser Leu Lys Gln Arg Leu Gln
1               5                   10                  15

Val Met Ile Met Val Ser Lys
            20

<210> SEQ ID NO 13
<211> LENGTH: 32
<212> TYPE: PRT
<213> ORGANISM: Artificial Sequence
<220> FEATURE:
<223> OTHER INFORMATION: Portion of mGAT1570XFP571CT

<400> SEQUENCE: 13

Glu Leu Tyr Lys Gln Pro Ser Glu Asp Ile Val Arg Pro Glu Asn Gly
1               5                   10                  15

Pro Glu Gln Pro Gln Ala Gly Ser Ser Ala Ser Lys Glu Ala Tyr Ile
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Portion of mGAT1577XFP578CT

<400> SEQUENCE: 14

Ala Tyr Met Phe Leu Thr Leu Lys Gly Ser Leu Lys Gln Arg Leu Gln
1               5                   10                  15

Val Met Ile Gln Pro Ser Glu Asp Ile Val Met Val Ser Lys
            20                  25                  30

<210> SEQ ID NO 15
<211> LENGTH: 25
<212> TYPE: PRT
<213> ORGANISM: Artificial Sequence
<220> FEATURE:
<223> OTHER INFORMATION: Portion of mGAT1577XFP578CT

<400> SEQUENCE: 15

Glu Leu Tyr Lys Arg Pro Glu Asn Gly Pro Glu Gln Pro Gln Ala Gly
1               5                   10                  15

Ser Ser Ala Ser Lys Glu Ala Tyr Ile
            20                  25

<210> SEQ ID NO 16
<211> LENGTH: 10

```
<212> TYPE: PRT
<213> ORGANISM: Artificial Sequence
<220> FEATURE:
<223> OTHER INFORMATION: Synthetic polypeptide

<400> SEQUENCE: 16

Phe Arg Glu Lys Leu Ala Tyr Ala Ile Thr
1               5                   10

<210> SEQ ID NO 17
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 17
gcatcttcgt gctgctttct ctcaccgtct tcctgctgc                              39

<210> SEQ ID NO 18
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 18
gcaccgagat gcacagcgtg accttctcgc cgcactcc                               38

<210> SEQ ID NO 19
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 19
gcttttgctc accgtcttcc tgctgctcat caccgag                                37

<210> SEQ ID NO 20
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 20
cggtgagcaa aagcagcacc gagatgcaca gcgtgacc                               38

<210> SEQ ID NO 21
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 21
gctcctgatc accgagatca tcccgtccac ctcgctgg                               38

<210> SEQ ID NO 22
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 22
```

-continued

```
cggtgatcag gagcagcagg aagacggtga gagaaagc                    38

<210> SEQ ID NO 23
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 23
ccaagattct gcctcccacc tccctcgacg taccgctgg                   39

<210> SEQ ID NO 24
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 24
gggaggcaga atcttggaga tgagcagcag gaacaccg                    38

<210> SEQ ID NO 25
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 25
ccaagattat gcctcccacc tccctcgacg taccgctgg                   39

<210> SEQ ID NO 26
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 26
gggaggcata atcttggaga tgagcagcag gaacaccg                    38
```

METHODS AND SYSTEMS FOR DETECTION OF STOICHIOMETRY BY FÖRSTER RESONANCE ENERGY TRANSFER

CROSS REFERENCE TO RELATED APPLICATIONS

This application claims priority to U.S. provisional application Ser. No. 61/206,958, filed on Feb. 6, 2009 entitled "Nicotine normalizes intracellular subunit stoichiometry of nicotinic receptors carrying mutations linked to autosomal dominant nocturnal frontal lobe epilepsy", incorporated herein by reference in its entirety.

STATEMENT OF GOVERNMENT GRANT

The U.S. Government has certain rights in this invention pursuant to Grant Nos. DA009121 and NS011756 awarded by the National Institutes of Health.

FIELD

The present disclosure relates methods and systems for detection of the stoichiometry of protein oligomers by Förster Resonance Energy Transfer.

BACKGROUND

Förster resonance energy transfer (FRET) is a mechanism describing an energy transfer between two chromophores. A donor chromophore, initially in its electronic excited state, may transfer energy to an acceptor chromophore in proximity through nonradiative dipole-dipole coupling. In fluorescence microscopy, fluorescence confocal laser scanning microscopy, as well as in molecular biology, FRET is a useful tool to quantify molecular dynamics in biophysics and biochemistry, such as protein-protein interactions, protein-DNA interactions, and protein conformational changes.

Some studies using FRET have been conducted to determine stoichiometry of some plasma membrane proteins. However, detection of changes in oligomer stoichiometry caused by pharmacological reagents or endogenous molecular chaperones, or the simultaneous detection of multiple stoichiometries expressed in the same region of interest still remains a challenge.

SUMMARY

Provided herein are FRET imaging and analysis methods that in several embodiments are suitable for detecting different stoichiometries of oligomeric complexes, and/or identifying compounds that of upregulate the function of a plasma membrane protein target associated thereto, for example, by causing changes in the expressed subunit/protomer stoichiometry of the oligomer.

In particular, in several embodiments of methods herein described, detection of one or more alternative stoichiometries in a FRET image is based on predetermined theoretical FRET amplitudes associated with each of the one or more stoichiometries.

In several embodiments of methods herein described, a plurality of components is identified in a distribution of the FRET amplitudes of all the pixels in a FRET image. The mean amplitudes of each distribution component are associated to a plurality of expressed oligomer stoichiometries.

According to a first aspect, a method to detect one or more stoichiometries of a protein complex is described. The method comprises: providing theoretically calculated FRET efficiencies for the one or more stoichiometries of the protein complex; performing FRET imaging and analysis on a region of interest expressing fluorescently labeled oligomer subunits of the protein complex to provide an acquired FRET image having a plurality of pixels each pixel having a FRET signal amplitude; calculating mean FRET efficiencies from the FRET signals amplitudes; and correlating the calculated mean FRET efficiencies with the theoretically calculated FRET efficiencies to detect the one or more stoichiometries of the protein complex.

According to a second aspect, a method to detect one or more stoichiometries of a protein complex is described. The method comprises: performing a FRET imaging acquisition of a region of interest including said protein complex, thus providing an acquired FRET image comprising a plurality of pixels. The method further comprises identifying for each pixel a FRET amplitude, thus providing a plurality of identified FRET amplitudes; and compiling a distribution of identified FRET amplitudes as a function of a number of pixels associated with each FRET amplitude to provide what is termed a "FRET distribution". The method also comprises identifying in the FRET distribution one or more predetermined FRET components, each component associated with a predetermined stoichiometry; and detecting one or more FRET amplitudes associated with the one or more stoichiometries based on the identified one or more components.

According to a third aspect a method to analyze an acquired FRET image having a plurality of pixels is described. The method comprises: analyzing the signal amplitude of each pixel in the acquired FRET image to provide, a FRET distribution comprising a plurality of FRET distribution components; and calculating for each FRET distribution component a mean FRET amplitude, thus simultaneously providing a plurality of measured mean FRET amplitudes in the acquired FRET image.

According to a fourth aspect, a method to analyze a Förster resonance energy transfer (FRET) imaging acquisition is described. The method comprises: providing an acquired FRET image, the acquired FRET image comprising a plurality of pixels; and identifying for each pixel its FRET amplitude, thus providing a plurality of identified FRET amplitudes. The method also comprises compiling a distribution of identified FRET amplitudes as a function of a number of pixels associated with each FRET amplitude; identifying in the FRET distribution one or more components, each component associated with a predetermined entity; and detecting one or more mean FRET amplitudes associated with the one or more components based on the identified one or more entities.

According to a fifth aspect, a method to identify a compound capable of regulating a plasma membrane protein complex is described. The method comprises: detecting alternative stoichiometries of the protein complex in a region of interest with a method for detecting one or more stoichiometries of a protein complex herein described. The method further comprises: quantifying a ratio of the detected alternative stoichiometries of the protein complex in the region of interest. The method also comprises incubating the cells expressing the protein complex a candidate compound; and quantitatively detecting changes in the quantified ratio of detected alternative stoichiometries of the protein complex in the region of interest following incubation with of the candidate compound. In several embodiments the region of interest is formed by a plurality of regions (e.g. various regions of a cell such as plasma membrane and intracellular organelles)

and corresponding changes in various regions of interest are associated with a regulated status of the protein complex.

According to a sixth aspect, a method to identify a compound capable of functionally regulating a plasma membrane protein complex is described. The method comprises: providing one or more stoichiometries of the plasma membrane protein complex; and incubating cells expressing the plasma membrane protein complex with a candidate compound. The method further comprises: quantitatively detecting the one or more stoichiometries of the plasma membrane protein complex following the incubation. The method also comprises comparing the one or more quantitatively detected plasma membrane protein complex stoichiometries with predetermined quantified stoichiometries associated with a regulation state of the plasma membrane protein complex; and identifying the candidate compound capable of regulating a plasma membrane protein complex based on the association of the one or more quantitatively detected plasma membrane protein complex stoichiometries with the predetermined quantified stoichiometries associated with the regulation state of the plasma membrane protein complex.

According to a seventh aspect a method to detect a functionally regulated plasma membrane protein complex is described. The method comprises: identifying one or more stoichiometries of the plasma membrane protein complex; quantitatively detecting a FRET efficiency of the one or more stoichiometries of the plasma membrane protein complex.

The method also comprises providing a theoretically calculated FRET efficiency of one or more stoichiometries of the protein complex, the one or more stoichiometry associated with functional regulation of the plasma membrane protein complex; and associating the quantitatively detected FRET efficiency of the one or more plasma membrane protein stoichiometries with the theoretically calculated FRET efficiency of the one or more stoichiometries associated with functional upregulation of the plasma membrane protein.

The method further comprises detecting regulation of the plasma membrane protein function based on the association between the quantitatively detected FRET efficiency and the theoretically calculated FRET efficiency.

According to an eighth aspect, a method to detect interactions of protein complexes with another protein is described. The method comprises: detecting one or more stoichiometries of the protein complex with a method herein described wherein identification of mean FRET efficiencies uncorrelated with the theoretically calculated FRET efficiencies indicates interaction with of the protein complex with another protein.

According to a ninth aspect a computer-readable medium is described, that contains a set of instructions that causes a computer to perform the analysis for at least one of the methods herein described.

According to a tenth aspect a computer is described, the computer comprising the computer-readable medium herein described.

According to an eleventh aspect, a system for detection of one or more stoichiometries in a protein complex is described. The system provides at least two items between a cell line capable of expressing a protein complex of interest; an expression plasmid capable of expressing fluorescently labeled subunits of the protein complex of interest; a computer readable medium herein described and confocal imaging elements.

The methods herein described and related compositions, materials, methods, and systems can be used in several embodiments, to allow the direct visualization of both steady state receptor stoichiometry and modulations of receptor stoichiometry resulting from exposure to compounds that regulate the function of the protein complex.

The methods, herein described and related compositions, materials, methods, and systems can also be used in several embodiments, to resolve multiple receptor stoichiometries present in a mixed population, to quantify the percentage of each stoichiometry present in a mixed receptor population.

The methods, herein described and related compositions, materials, methods, and systems can further be used in several embodiments, to allow specific analysis of the different receptor stoichiometries present in different subcellular regions or organelles in a single cell or region of interest.

The methods herein described and related compositions, materials, methods, and systems can additionally be used in several embodiments, to allow time-resolved FRET measurements of single cells exposed to compounds that regulate the function of the protein complex, to obtain high-resolution measurements of receptor assembly.

The methods, herein described and related compositions, materials, methods, and systems can additionally be used in several embodiments, to determine the role of auxiliary subunits or other accessory proteins in the control of oligomer/complex stoichiometry in both the absence and presence of a compound and in particular a drug that modulates channel function.

The methods herein described and related compositions, materials, methods, and systems can additionally be used in several embodiments, to allow time-resolved FRET measurements of single cells exposed to neurotransmitter transporter substrates, to obtain high-resolution measurements of substrate mediated neurotransmitter transporter oligomer disassembly.

The methods herein described and related compositions, materials, methods, and systems can additionally be used in several embodiments, to allow steady state and time-resolved FRET measurements of single cells co-expressing different G-protein coupled receptor subunits to determine the role of oligomerization in targeting of the receptor, altered coupling, altered pharmacology, altered internalization and ligand-independent functions.

The methods herein described and related compositions, materials, methods, and systems can additionally be used in several embodiments, to allow specific analysis of the influence of receptor agonists and antagonists on G-protein coupled receptor oligomerization and the downstream effects on targeting of the receptor, altered coupling, altered pharmacology, altered internalization and ligand-independent functions.

The methods, herein described and related compositions, materials, methods, and systems can be used in several embodiments in connection with applications wherein a FRET analysis is useful, including but not limited to the fields of biological research, human and veterinary medicine, such as diagnostic methods based on detection of stoichiometries of an oligomer or protein complex associated with a condition in an individual; therapies such as effective smoking cessation drugs that target specific stoichiometries of a an oligomer or protein complex; such as treatment for Parkinson's Disease or Autosomal dominant nocturnal frontal lobe epilepsy (ADNFLE) or as antihelmintics that target nAChRs expressed in the nerves and muscle of parasitic nematodes that infect humans or livestock.

In particular, methods herein described and related compositions material methods and systems can be used in several embodiments for the identification of compounds that prevent increased hetero-oligomerization of the $AT_1$-receptor for the vasopressor angiotensin II and the $B_2$-receptor for the vasodepressor bradykinin that results in angiotensin II hypersensitivity in preeclampsia (AbdAlla et al., 2001); to identify and develop compounds that specifically target the adenosine $A_{2A}/CB_1$ receptor hetero-oligomers that mediate the motor depressant effects of the centrally administered cannbinoid compounds (Carriba et al., 2007); to identify compounds that specifically promote the assembly of serotonin 5-$HT_{2A}$ receptor/metabotropic glutamate receptor 2 complexes for the treatment of psychosis. (Gonzalez-Maeso et al., 2008). The details of one or more embodiments of the disclosure are set forth in the accompanying drawings and the detailed description and examples below. Other features, objects, and advantages will be apparent from the detailed description, examples and drawings, and from the appended claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

DETAILED DESCRIPTION

Figure 1:
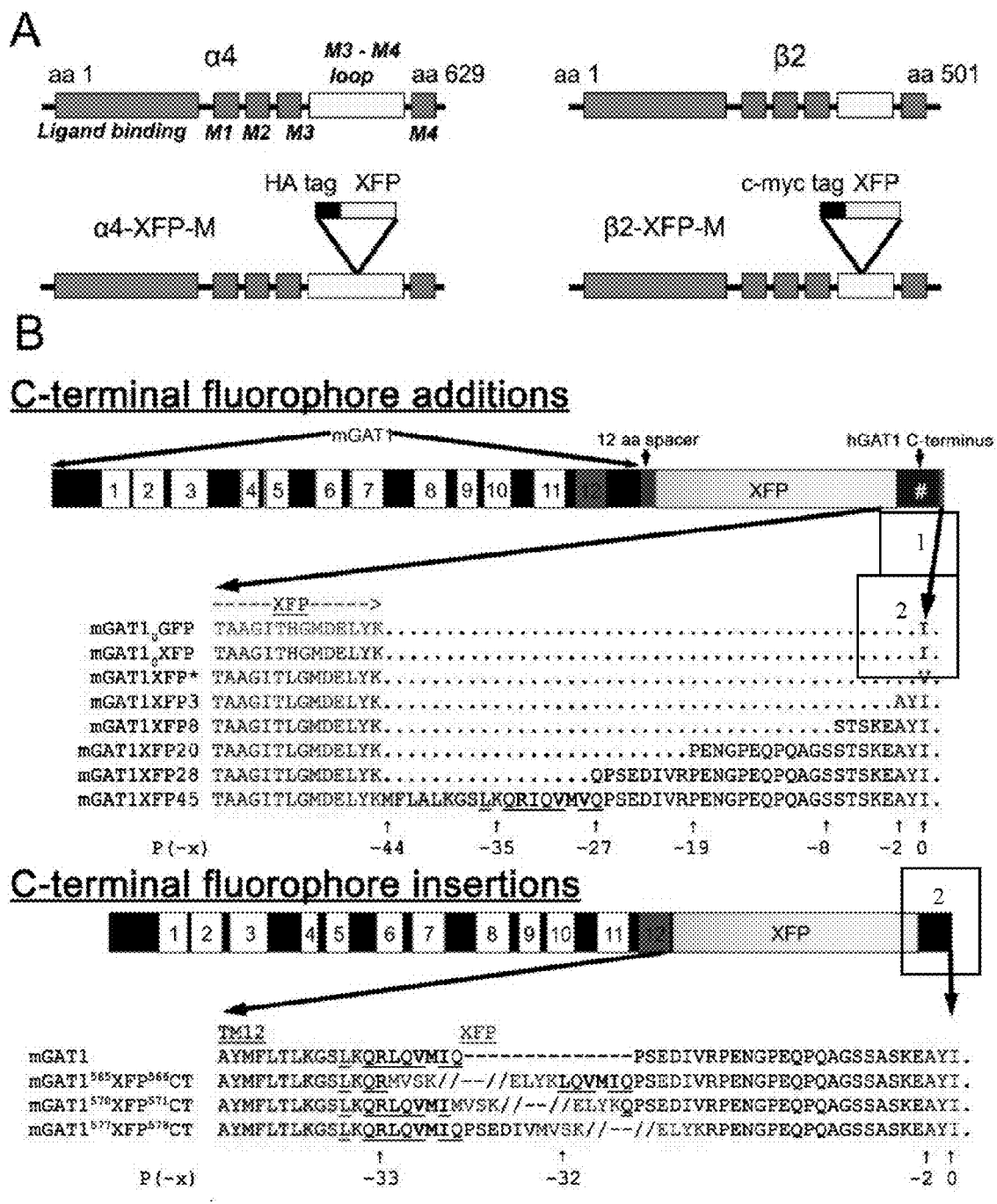
FIG. 1 shows: (A) Designs of fluorescently tagged α4 and β2 nAChR subunits. The α4-XFP and β2-XFP chimeric constructs illustrating the location of insertion of the fluorescent protein within the nAChR subunit is shown. (B) Schematics of fluorescent mGAT1 construct designs and primary sequence alignments of the regions that are fused with XFP. In each schematic, the mGAT1 peptide is illustrated as a black bar; transmembrane domains are marked as superimposed numbered boxes. TM12 is shaded; linkers deriving from cloning vector are shown in gray and the XFP as a light gray shaded box. Additional human GAT1 (hGAT1) sequence is shown as a dark shaded box after the XFP (# denotes a variable number of residues depending in the construct design). All schematics and their internal features are scaled according to sequence length. Two classes of florescent mGAT1 fusions, C-terminal additions and C-terminal fusions are displayed with their names to the left (SEQ ID NO:1 to SEQ ID NO: 15). For the fusions of XFP to the mGAT1 C-terminal, only the last 14 residues of the fluorophore and any appended hGAT1 or other sequence is displayed. For the mGAT1 C-terminal XFP insertions, the regions immediately adjacent to the insertion site and first four and last four residues of the XFP are displayed. Displayed GAT1 C-terminal sequences are numbered with the terminal residue being P(0); upstream sequence positions are negative. Other important highlighted regions include: fluorophore sequence below the -XFP→ arrow, the terminal hydrophobic residues of mGAT1$_0$GFP and mGAT1XFP* (box 1), the endogenous GAT1 Class II PDZ-interacting motif -AYI (box 2), mouse or human GAT1 TM12 sequence are gray, non-classical endocytic motifs homologous to FREKLAYAIT (SEQ ID NO: 16) in mDAT (conserved residues underlined) (Holton et al., 2005; Boudanova et al., 2008), and RL or RI endoplasmic reticulum export motif (bold) (Farhan et al., 2007) and VMI or VMV (bold) ERGIC export motif (Farhan et al., 2008).

Provided herein are methods for acquiring and analyzing FRET images to detect stoichiometries of a protein oligomer or complex, identifying compounds capable of modulating the ratio of expressed stoichiometries in the sample which can result in regulation (and in particular upregulation) of a plasma membrane protein (or another measurable change in function of the same) and related materials, compositions, methods and systems.

The term "detect" or "detection" as used herein indicates the determination of the existence, presence or fact of a species or signal in a limited portion of space, including but not limited to a sample, a reaction mixture, a molecular complex and a substrate. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

The term "stoichiometry" as used herein describes the ratio of each different type of protein subunit that assembles in a particular geometric arrangement in space to form a protein complex/oligomer. Oligomeric protein complexes for which multiple stoichiometries exist include cys-loop receptors (glycine receptors, 5HT-3 receptors, neuronal and muscle nicotinic acetylcholine receptors), transient receptor potential channel superfamily, and solute carrier (SLC) transporters.

The terms "oligomer" or "protein complex" as used herein indicates a protein complex with multiple components. Any protein complex formed by two or more subunits that assemble in a functional unit, is an exemplary oligomer. Exemplary protein complexes include most known ion channels, receptors and transporters, which are assemblies of multiple proteins known as subunits or protomers. Various components of protein complexes herein described are herein also collectively identified as "complex subunits" or "subunits" which term in the sense of the present disclosure identifies any single protein molecule that assembles (or "coassembles") with other protein molecules encoded by a related gene family member to form a protein complex. Possible exemplary subunits comprise proteins that are naturally comprised in a certain protein complex as well as proteins that are engineered to interact with one or more natural or engineered protein components. For example neurotransmitter receptors can be formed by multiple assembled receptor subunits encoded by several related genes, and can also associate with molecular or pharmacological chaperones, cytoskeletal proteins, enzymes or other signaling molecules that form part of larger protein complexes than just the core protein subunit components of receptor.

The term "auxiliary subunit" describes a protein that can assemble as a part of a protein complex to modulate the trafficking, pharmacological and the biophysical properties of the complex but which is not absolutely required to exist in the complex for the protein complex to function. Auxiliary subunits can substitute for an absolutely required subunit if other absolutely required subunits are present in the complex, or it can assemble as a peripheral part of the complex to modulate the function of the core complex assembled from absolutely required subunits.

The term "accessory protein" describes a protein that can associate with a protein complex but which is not encoded by a gene homologous to the absolutely required or auxiliary subunits of the protein complex. Accessory proteins are not absolutely required for the function of the protein complex and cannot substitute for subunits in the complex but they can modulate the trafficking, pharmacological and the biophysical properties of the complex or be involved in biological signaling pathways in which the protein complex under investigation is involved.

In some embodiments a protein complex has a defined geometry. In some of those embodiments a particular geometry of the protein complex can be altered under defined treatment conditions.

In several embodiments here described, the protein complexes can localize in regions inside the cell such the nucleus, the endoplasmic reticulum, the Golgi apparatus, vesicles that move from any of these compartments to and from the plasma membrane and the plasma membrane.

The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules. The term "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called an oligopeptide. As used herein the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

In several embodiments, methods and systems herein described use FRET detection to identify the number of subunits that are comprised in an oligomer. In particular, in embodiments, wherein a specific geometry of the oligomer of interest is already known (e.g. from a protein crystal structure) or identifiable by suitable techniques, the methods herein described can also be used to detect a differential utilization of alternative subunits to assemble functional oligomers.

In some embodiments, in methods and systems herein described FRET detection can also be applied to detect interactions between a multiplicity of other protein-protein interactions.

The term "Förster resonance energy transfer" or "FRET" as used herein indicates a mechanism describing an energy transfer between a donor chromophore, initially in its electronic excited state, to an acceptor chromophore in proximity through nonradiative dipole-dipole coupling. Detection of FRET enables quantification of molecular dynamics such as protein-protein interactions, protein-DNA interactions, and protein conformational changes.

The term "chromophore" describes is the part of a molecule responsible for its color. In biological molecules that serve to capture or detect light energy, the chromophore is the moiety that causes a conformational change of the molecule when hit by light. In methods and systems herein described the chromophores resides within the "fluorophore" molecule. The term "fluorophore" refers to a substance or molecule or a portion thereof which is capable of exhibiting fluorescence in a detectable image. The fluorophore will absorb energy of a specific wavelength and re-emit energy at a different (but equally specific) wavelength. Fluorescent labels that can be used include biological and chemical fluorophores include, but are not limited to biological fluorophores and chemical fluorophores.

Exemplary biological fluorophores comprise T-sapphire, Cerulean, mCFPm, CyPet, EGFP, PA-EGFP, Emerald, EYFP, Venus, mCitrine, mKO, mOrange, DSRed, JRed, mStrawberry, mCherry, PA-mCherry, mRuby, Tomato, mPlum, mKate, mKatushka, Kaede, Halotag, and superecliptic fluorine. Exemplary chemical fluorophores comprise Alexafluor, Rhodamine, BODIPY, Tetramethylrhodamine, Cyanin dyes, Fluorescein, Quantum dots, IR dyes, FM dyes, ATTO dye. Additional fluorophores are identifiable by a skilled person upon reading of the present disclosure.

The term "donor" and "acceptor" as used herein indicates fluorescent labels that are suitable for FRET detection, wherein the terms "label" and "labeled molecule" as used herein as a component of a complex or molecule refer to a molecule capable of FRET detection, including but not limited to, fluorophores chromophores, and the like.

For an example of a typical FRET approach for monitoring a complex formation between two molecules, one of the molecules is labeled with a donor- and the other with an acceptor-fluorophore, and these fluorophore-labeled molecules are mixed. When the donor and acceptor are dissociated, the donor emission is detected upon the donor excitation. On the other hand, when the donor and acceptor are in proximity (typically 1-10 nm) due to the interaction of the two molecules, the acceptor emission is predominantly observed because of the intermolecular FRET from the donor to the acceptor. In another exemplary approach directed to monitor protein conformational changes, the target protein is labeled with a donor and an acceptor at two loci. In a further exemplary approach directed to detect conformational changes in a protein, when a twist or bend of the protein brings the change in the distance or relative orientation of the donor and acceptor, FRET change is observed. If a molecular interaction or a protein conformational change is dependent on ligand binding, this FRET technique is applicable to fluorescent indicators for the ligand detection.

In several embodiments, selection of the appropriate pair of FRET labels for FRET measurements in the methods herein described can be performed in view of the specific detection to be performed and the related experimental design. For example, in some embodiments, wherein direct interaction between proteins in a live cells is desired a pair of labels of choice can be provided by green fluorescent protein (GFP) variant which are capable of reporting a separation of <100 Å (Sekar and Periasamy, 2003). GFP variants can also be used in embodiments where ability to attach a label to a host protein by genetic engineering without need for processes of purification, chemical modification, and intracellular injection of a host protein is desired. For example, a FRET pair can be chosen based on particular requirements for the protein being studied such as distance between protein components being tested, subcellular location of the protein (example, is the protein in the ER or Golgi, peripheral vesicles or nucleus) and the type of microscopy being used to measure FRET (example, confocal versus TIRF). Criteria for an optimal pair are a large Förster radius, higher quantum yield of the acceptor fluorophore and increased photostability of donor and acceptor fluorophores.

In some embodiments, the FRET pair for biological use can be an enhanced, cyan fluorescent protein (ECFP)-yellow fluorescent protein (EYFP) pair. Both are color variants of GFP. Each FRET pair selected from the above list of fluorophores possesses unique advantages that may make it more suitable than others for particular proteins of interest. For example, the ECFP-EYFP pair displays a large spectral overlap between donor emission and acceptor excitation, allowing for robust FRET. In addition, EYFP has a high quantum yield and is therefore very suitable as a FRET acceptor. The EGFP-mCherry pair demonstrates a large Förster radius, allowing for FRET measurements in proteins with a large distance separating the fluorophores. The spectral overlap between EGFP emission and mCherry is minimal, thus negating false FRET measurements because of donor crosstalk and bleedthrough. EGFP is highly photostable.

In several embodiments, interaction between donor and acceptor is detected through quantifying FRET efficiency. In several embodiments, the FRET efficiency E is defined by the Förster equation described in (Lakowicz, 2006) incorporated herein by reference in its entirety. In several embodiments, methods of the present disclosure uses two classes of techniques that provide approximate E values based on microscopic images acceptor photobleach FRET and sensitized FRET (Wallrabe and Periasamy, 2005; Jares-Erijman and Jovin, 2006).

In several embodiments, interaction between donor and acceptor is reported by quantification of FRET amplitude. The FRET amplitude measured from sensitized emission of the acceptor during excitation by the donor and is not a direct measurement of the FRET efficiency E. In several embodiments presented herein, the FRET amplitude is defined by equation 2 or equation 3 as the magnitude of the net FRET (nF) or normalized FRET (NFRET) signal. The term FRET amplitude can also be applied to describe the magnitude of any FRET signal calculated by any known method to quantify FRET from sensitized emission images that is not a direct measure of the FRET efficiency E. The acquired FRET amplitude is an indirect measure of E (Elangovan et al., 2003) and responds nonlinearly to variations in the extent of interaction between fluorophore-tagged molecules (Gordon et al., 1998).

In some embodiments, the FRET imaging acquisition can be performed by acceptor photobleaching. In a specimen expressing both donor- and acceptor-tagged molecules, the existence of FRET causes a decrease in the donor intensity, proportional to the number of donor-tagged molecules that interact with acceptor-tagged molecules. Thus, "acceptor photobleach" FRET directly measures the FRET efficiency E by quantifying the increase in the donor intensity following photobleach of the acceptor (although artifacts including acceptor photoconversion and donor photobleach can distort this measurement (Rizzo et al., 2006)).

In some embodiments, the FRET imaging acquisition can be performed by sensitized emission FRET. The acceptor displays sensitized emission during excitation of the donor. Measurements of such "sensitized FRET" or "sensitized emission FRET" preserves the fluorophores in the sample. Rather than a acquiring a time series of images, it requires the acquisition of either a single image by a device capable of detecting the entire emission spectrum of both the donor and acceptor fluorescence which is then spectrally resolved through linear unmixing of the full-spectrum image into donor, acceptor and FRET images or alternatively using a standard wide-field or confocal fluorescence imaging microscope, the use of three different fluorescence filter cubes appropriate for acquiring images of: 1), the donor channel ($I_{DD}$, donor excitation and emission), 2), the FRET channel ($I_{DA}$, donor excitation, acceptor emission), and 3), the acceptor channel ($I_{AA}$, acceptor excitation and emission).

The term "linear unmixing" as used herein is used to describe the process of using the spectral signature of each fluorophore present in an image to deconvolve from lamda stacks (images of the lateral (x,y) plane as a function of wavelength) to separate the contributions of each individual fluorophore signal in each pixel of the acquired image.

In particular, in several embodiments, methods herein described are based on detection of one or more stoichiometries in a FRET image that correspond to theoretically calculated FRET efficiencies associated with each of the one or more stoichiometries. In some embodiments, the FRET efficiency for each individual stoichiometry can be theoretically calculated by including in the calculations the number of subunits in the oligomer/complex, the number of donor and acceptor labeled subunits included in the oligomer/complex, the relative position of the donor and acceptor fluorophores to one another, all the possible distances between the fluorophores incorporated in the oligomer/complex, the geometry of the subunits in the oligomer (e.g. triangle, square, pentagon, rhomboid) and the Förster distance for the FRET pair used in the experiments according to procedures exemplified in the Examples section. In some embodiments, wherein the geometry of the complex is considered, it can be taken into account that the dipole orientation factor $\kappa^2$ differs between adjacent and non-adjacent subunit pairs in geometries where non-adjacent subunits exist and that in general, the ratio $\kappa^2$ (non-adjacent subunits)/$\kappa^2$ (adjacent subunits) lies between 1 and 2 (Corry et al., 2006). In particular, in embodiments wherein dipole orientation is not known an analysis can be performed considering that the $\kappa^2$ (non-adjacent subunits)/$\kappa^2$ (adjacent subunits) equals to 1, and the efficiencies of energy transfer within an isolated oligomer can then be calculated analytically (e.g. Example 20, FIG. 15).

In some embodiments, the measured FRET efficiencies from acceptor photobleach experiments or the mean FRET amplitudes of the components of the FRET distributions are then associated with predetermined theoretically calculated FRET efficiencies for each potential stoichiometry. In some embodiments, when applying the acceptor photobleach method, the FRET efficiency from each possible stoichiometry in the sample is multiplied by the probability that that stoichiometry exists and the sum of FRET efficiencies from each stoichiometry will indicate how homo- or heterogeneous is the mixture of stoichiometries in the sample (see e.g. Example 9, FIG. 3). In some embodiments, for sensitized emission FRET the mean FRET amplitude of each component of the FRET distribution can be associated with the specific predetermined theoretically calculated FRET amplitude for a particular stoichiometry. In some of these embodiments, the area of the total distribution represented by each component reports the percentage of the total oligomer/complex population in the region of interest comprised by that stoichiometry. In some embodiments, this determination can be performed for empirical FRET measurements for specific regions of interest comprising the oligomers/complexes expressed in a specific region of the cell or for the whole cell.

The term "region of interest" or "ROI" as used herein indicates the area of the image from which the data is measured. This is a user defined area that can comprise a whole cell (typically encompassing all the fluorescent pixels in the image of the cell minus the nonfluorescent cell nucleus) or a specific organelle or region within the cell. One image can have a single ROI or a plurality of ROIs. In some embodiments, specific fluorescent organelle markers, in particular markers that do not significantly interfere with the FRET signal, can be coexpressed in the cells to highlight the desired specific region of interest. In embodiments, where, for example, the focus on FRET in a particular organelle is not necessary or a suitable marker is unavailable, subcellular regions of interest can be defined using the fluorescence patterns of the fluorescent species being studied for FRET. For example, the peripheral ROI could describe for any cell the plasma membrane and a narrow annulus (~700 nm) that includes the immediately adjacent cytoplasm as exampled by the region of bright fluorescence at the outer edge of cells expressing fluorescent GAT1 transporters imaged by confocal microscopy (Example 18 and Example 19 and related FIGS. 10A, 12A 14A). The term "intracellular ROI" typically indicates the space in the cell within the region defined by a peripheral ROI but subtracting the dark space occupied by the cell nucleus, and is usually densely filled by endoplasmic reticulum (ER) (see e.g. Example 19 and related FIG. 11A). The term "perinuclear ROI" typically encompasses a region adjacent to the cell nucleus; according to organelle markers, this ROI comprises mainly ER and Golgi.

In some embodiments, determination of the FRET amplitudes used to determine stoichiometry is performed on one or more pixels of a ROI.

As used herein the term "pixel" indicates the smallest addressable element that can be controlled in a digital image. In several embodiments, the FRET amplitude of a plurality of pixels are considered in ROIs of a FRET image. In those embodiments, subsequent processing of the FRET amplitudes is performed with the FRET amplitudes determined for the pixels rather than using the mean FRET amplitudes associated to the whole ROI. In some embodiments, the optics of the microscope and any additional magnification applied by the imaging software is important in determining the area of the sample represented in each pixel of the digital image. According to this embodiment, the amplitude of the FRET signal in each pixel is influenced by the number of donor-acceptor pair radii in the oligomers (e.g. two possible FRET radii exist in a square tetramer; r and r$\sqrt{2}$, the stoichiometry of the donor and acceptor fluorophores within each oligomer, the relative concentration of each oligomer stoichiometry type, and in cases where multiple types of oligomer exist in the same pixel (e.g. mixture of dimers and tetramers) the proportions of oligomer type that exists in the pixel (see e.g. Example 20).

In some embodiments for each pixel a NFRET amplitude is identified, thus providing a plurality of identified NFRET amplitudes.

The term "NFRET amplitude" as used herein indicates the bleed-through corrected FRET signal amplitude from each pixel normalized to the square root of the product of the donor and acceptor fluorescence intensities in the same pixel (Equation 3). Expressing FRET as NFRET controls for large variations in the expression levels of each fluorophore between different cells and provides a measure of FRET that is readily comparable between different samples.

In several embodiments, the identified FRET signal of each pixel in the ROI is binned according to its NFRET amplitude into a "distribution" of NFRET amplitudes throughout the ROI, to provide an NFRET or FRET "distribution".

In several embodiments, one or more predetermined NFRET "components" are identified in the NFRET distribution. The FRET amplitude of each pixel is the average FRET amplitude of all the FRET yielding oligomers/complexes present in each pixel. Thus in some embodiments the NFRET distribution is fit with Gaussian "components" that distribute normally about the true mean NFRET amplitudes for each stoichiometry/oligomer type present in the ROI examined and correspond to the FRET amplitude/efficiency predetermined in theoretical calculations for each stoichiometry.

In several embodiments, one or more stoichiometries associated with the one or more components are detected based on the identified one or more components.

In some embodiments, association of oligomeric proteins with other cellular complexes can be detected by additional components in the NFRET distribution that are not explained by the predetermined theoretical calculations of all possible types of oligomer or stoichiometries.

In some embodiments, the association between NFRET distributions and stoichiometries can be determined by analytically calculating the FRET efficiency of each stoichiometry based on the position of the donor and the acceptor E can indirectly determined from sensitized FRET images. These yield net FRET (nF) values (Equation 2), from which can be determined the NFRET (Equation 3) or an indirect measure of E (Equation 4).

In some embodiments, the one or more identified stoichiometries can be quantitatively detected as a percentage of a total population of expressed oligomers/complexes by dividing the area of the one or more NFRET components associated with the one or more stoichiometries by the area of the summed fit of all the NFRET components in the complete NFRET distribution for the ROI.

In some embodiments, the one or more identified stoichiometries can be qualitatively detected for example by detecting a relative shift in equilibrium between each type of stoichiometry in the total population as conditions change. In some embodiments, a forced over-expression of one of the subunits can be performed to force the stoichiometry in the system to one predetermined stoichiometry, qualitative detection of the predetermined stoichiometry in the resulting mixed population of stoichiometries can be qualitatively performed using FRET amplitudes detected with one of the methods here described.

In some embodiments, the ratio of plasmids for each subunit included in the transfection can be biased to force the expressed stoichiometry in a sample to be purely one stoichiometry; the FRET efficiency for which can be empirically determined by the acceptor photobleach method.

In some embodiments, changes in stoichiometry can be monitored by performing acceptor photobleach to quantify FRET efficiencies and comparing the measured FRET efficiencies with FRET efficiencies associated with various transfections with forced stoichiometries.

In some embodiments, the association between NFRET distribution components or FRET efficiency and stoichiometries can be followed or confirmed by Fluorescence intensity ratio (FIR) analysis.

In particular, in some embodiments, the FRET imaging acquisition can be performed by a pixel-by-pixel FRET detection from sensitized acceptor emission. For example in some embodiments, full emission spectra images are acquired, linearly unmixed using reference spectra from samples expressing solely the donor- or acceptor-tagged fusion constructs to unambiguously separate the donor and acceptor signal from each pixel of the spectral images. In some embodiments, where fixed samples are used and detection of immobilized protein complexes is desired, a pixel-by-pixel FRET detection from photobleach is feasible.

As used in the present disclosure the wording "pixel by pixel" indicates that the FRET in each pixel in the ROI is individually recorded instead of being the averaged FRET signal over the whole ROI.

In some embodiments, the pixel-by-pixel FRET method analysis can be refined by including the NFRET amplitude of each pixel as a datum in the analysis rather than averaging the signal amplitudes of all the pixels in a region of interest.

In some embodiments, the refined pixel-by-pixel FRET method analysis described above can be used to visualize several components to the total FRET signal amplitude distribution. This technique can be used to reveal that FRET varies among subcellular compartments as defined by each ROI and that within every ROI, the total NFRET distribution can consists of multiple subcomponents, each with its own distinct mean NFRET amplitude.

In some embodiments, pixels are binned according to their NFRET amplitude into a FRET distribution compiled from pixel-by-pixel analysis of FRET images from sensitized acceptor emission experiments.

In some embodiments, the refined pixel-by-pixel FRET method analysis can be used to qualitatively detect one or more stoichiometries of an oligomer/complex in the same ROI in a sample.

In some embodiments, the refined pixel-by-pixel FRET method analysis can be used to quantitatively detect one or more stoichiometries of an oligomer/complex in the same ROI in a sample.

In some embodiments, the refined pixel-by-pixel FRET method analysis can be used to reveal that a two-component NFRET distribution can arise from two alternate stoichiometries of one type of oligomer/complex geometry (Example 21), or from two alternate oligomer geometries (Example 20).

In some embodiments, the mCherry and meGFP FRET pair can be used for recording pixel-by-pixel FRET measurements by sensitized emission.

In some embodiments, the detected stoichiometry is associated with a biological activity of the oligomer/complex and the FRET detected is indicative of the biological activity in the ROI. In particular, in some embodiments the detected stoichiometry can be associated with functional upregulation or downregulation of the target oligomer/complex.

The term "functional downregulation" as used herein indicates a process by which a larger stimulus (e.g. a larger concentration of drug) is required to elicit the same response as before the experimental conditions that caused the change in function were applied. An increased response to the same stimulus instead termed "functional upregulation".

In particular in some embodiments, detecting functional regulation of the plasma membrane protein can be performed based on quantifying the ratios of expressed plasma membrane protein stoichiometries expressed in the sample after incubation with candidate pharmacological compounds, molecular and/or endogenous chaperones, the introduction of disease relevant mutations or coexpression of additional subunit types and/or auxiliary subunits or accessory proteins.

The term "incubation" as used herein indicates a spatial relationship between two items provided for a time and under condition such that at least one of the reciprocal or non reciprocal action or influence between the two items can be exerted. In particular, incubation can be performed between a compound and a cell expressing a protein complex of interest and can result in a direct contact and/or interaction between the compound and the protein complex or can result in a modification of the protein complex of interest following an indirect action of the compound. For example in some embodiments, many compounds can act indirectly and cause changes in a protein complex stoichiometry by acting on another receptor/protein in the cell which then elicits a signal that changes the stoichiometry of the protein being studied by FRET. In those embodiments, modulation of a protein complex stoichiometry by the compound is performed indirectly and does not require direct contact between the compound and the complex being studied by FRET. Exemplary incubations can be performed by bathing the whole sample (cell/cells) in a solution containing the compound under suitable conditions which depend on the specific cells and the specific compound and are identifiable by a skilled person upon reading of the present disclosure.

In some embodiments, a compound effect on the regulation of a protein complex is performed by detecting FRET amplitudes following incubation of the compound with the cell expressing the protein complexes and then comparing the detected FRET amplitudes with predetermined FRET amplitudes associated with a regulation status of interest. For example, if for a certain protein complex it is known that the high-sensitivity receptors is associated to larger FRET amplitudes, that low sensitivity receptors are associated to small FRET amplitudes, the ratio of the low to high-sensitivity receptors can be detected before and after drug incubation and quantify the increase in high-sensitivity stoichiometry represented by increased FRET to quantify the upregulation associated with high sensitivity receptors.

In some exemplary embodiments, FRET data acquisition can be used to detect one or more stoichiometries of pentameric Cys-loop receptors.

The term "pentameric Cys-loop receptors" as used herein indicates receptors from the Cys-loop ligand-gated ion channel superfamily which is composed of nicotinic acetylcholine, $GABA_A$, $GABA_A$-ρ, glycine and $5-HT_3$ receptors. These receptors are composed of five protein subunits which form a pentameric arrangement around a central pore. There are usually 2 alpha subunits and 3 other beta, gamma or delta subunits (some consist of 5 alpha subunits). Cys-loop receptors typically possess a characteristic loop formed by a disulfide bond between two cysteine (Cys) residues 13 highly conserved amino acids apart near the N-terminal extracellular domain of the alpha subunit. All subunits consist of a conserved extracellular large N-terminal domain; three highly conserved transmembrane domains; a cytoplasmic loop of variable size and amino acid sequence; and a fourth transmembrane domain with a relatively short and variable extracellular C terminal.

In other exemplary embodiments, the oligomer/complex to be detected by FRET can form homo and/or hetero oligomeric complexes of GABA receptor, GluCl channel, Cyclic nucleotide gated channel, TRP channel, purinergic receptor, potassium channel, solute (SLC) transporter and GPCR subunits. Representative molecules of the oligomer detectable by method herein described are neuronal nicotinic acetylcholine receptors (nAChRs) that are bound activated by nicotine, the main addictive component of tobacco.

The nAChRs receptors are composed of ~16 types of nAChR subunits that are expressed differentially in various neuronal and non-neuronal cell types. Unlike most other receptors that are downregulated in response to chronic activation, the nAChRs undergo upregulation in the chronic presence of nicotine. This phenomenon, termed the "upregulation paradox" is important in the context of nicotine addiction. It is now known that α4β2 is a strongly upregulated subtype and that other subtypes are also upregulated by nicotine (Nguyen et al., 2003), that the upregulated receptors are probably active rather than desensitized, and that the extent of upregulation is region- and cell-specific (Nashmi et al., 2007). Rodents exposed to chronic nicotine display increased levels of [$^3$H]-nicotine binding (Marks et al., 1983; Schwartz and Kellar, 1983), and smoking also upregulates α4β2 receptors in the human brain. A study from the inventors' laboratory suggested that the nicotine-induced upregulation of neuronal nAChRs can delay the progression of Parkinson's disease (Nashmi et al., 2007).

In some embodiments, FRET detection can be used to identify a compound capable of functionally up- or down-regulating nAChRs or another plasma membrane protein (e.g. by detecting an increase in the total receptor population represented by the corresponding plasma membrane protein complex).

The term "compound" as used herein indicates a molecule, drug, peptide or other pharmacological reagent that can influence the properties of another molecular target species.

In some embodiments one or more stoichiometries of the plasma membrane protein can be detected and the shift in the ratio of each type of expressed stoichiometry quantified when incubated with candidate compounds. In particular for nAChRs, incubations can be performed with nicotine or other compounds which act as full or partial agonists or antagonists for nAChRs. Additional compounds suitable as candidate molecules for regulation of the function a homo- or heterooligomeric protein complex and in particular nAChRs are identifiable by a skilled person.

In some embodiments, exposure of cells expressing the oligomer to a candidate compound can be performed by incubation. Detection by FRET of the one or more stoichiometries of the plasma membrane protein expressed before and following incubation of the cells with the candidate compound that regulates plasma membrane protein function is performed, thus quantifying the percent of the total oligomer population represented by each stoichiometry before and after incubation with the candidate compound. The one or more detected plasma membrane protein stoichiometries can be therefore compared with predetermined quantified stoichiometries associated with upregulation of the plasma membrane protein.

In some embodiments, identifying the candidate compound capable of upregulating a plasma membrane protein can be based on detecting a change in measured FRET for the plasma membrane protein that is associated by predetermined theoretical calculation with an increase in the one or more plasma membrane protein stoichiometries associated with functional upregulation by compounds known to functionally upregulate the plasma membrane protein.

In some embodiments, since most upregulation studies including the fluorescence-based assays described in the present disclosure rely on heterologous receptor expression in cell lines, the concept of cell autonomy allows translation of findings from in vitro studies to in vivo systems.

In some embodiments, practical fluorescence-based assays that distinguish between alternative stoichiometries in pentameric Cys-loop receptors and thus allow the direct visualization of receptor upregulation are described. The assays are developed to visualize the upregulation of nicotinic acetylcholine receptors by detecting changes in receptor stoichiometry, but can be applied to study the modulation of channel stoichiometry in many different classes of membrane ion channels, receptors and transporters.

In some embodiments, imaging acquisition and analysis methods are described that quantify the sensitized Förster resonance energy transfer (FRET) signal from cells expressing fluorescent fusions of the neuronal nicotinic acetylcholine receptor (nAChR) in order to measure subcellular receptor assembly in live cells. Through the judicious co-expression of fluorescently tagged ion channel subunits at appropriate expression levels and in appropriate cell lines, the methods described here also allow the investigator to determine the precise combination of subunits expressed in an oligomeric ion channel.

In some embodiments, assays that directly visualize modulation of channel subunit stoichiometry and/or upregulation of ion channel function in response to changes in the extracellular environment are described. These assays can be used in the basic research laboratory to facilitate the identification of novel compounds that can specifically mediate these processes. The techniques can be applied when fluorescent channels are expressed in immortalized cell lines, or in primary cell cultures and will be beneficial to the fields of human and veterinary medicine; hastening the development of novel and more effective smoking cessation therapies, treatments for Parkinson's Disease and Autosomal dominant nocturnal frontal lobe epilepsy (ADNFLE), and even antihelmintics that target specific stoichiometries of nAChRs expressed in the nerves and muscle of parasitic nematodes that infect humans or livestock.

In some embodiments, pixel-by-pixel analysis of sensitized FRET amplitude allows the accurate measurement of FRET in various subcellular regions, and the individual components of FRET distributions in each region of interest (ROI) correlate with functional phenotype. Analyzing each construct's number of Gaussian components in a FRET distribution overcomes complications from the fact that each construct has a unique separation and/or orientation between fluorophores. It was simply assumed that the rank order of FRET distribution components arises from mechanisms that are common across the entire set of constructs.

In some embodiments, multiple oligomerization states or channel stoichiometries in a single region of interest can be observed in the basal state (i.e. in the absence of agonist or substrate). The direct visualization of the process of channel upregulation which occurs through modulation of the expressed channel stoichiometries in the total receptor population can also be directly visualized.

In some embodiments, the method allows modulation of channel stoichiometries present in different cell organelles to be observed simultaneously in the same cell. In either the basal state or during incubations with pharmacological reagents, in a region of interest expressing mixed population of channel stoichiometries, one is able to quantify the proportions of the total receptor population represented by each specific channel stoichiometry. The technique forms the basis for novel methods to screen for compounds which upregulate ion channels, receptors or transporter proteins by modulating their subunit stoichiometry. Alternatively, one will be able to use the method to screen for compounds that target a specific channel stoichiometry.

In particular in some embodiments, it is possible to detect specific channel stoichiometry. In some of those embodiments, the method comprises: calculating predetermined theoretical FRET amplitudes for one or more possible stoichiometries of the plasma membrane protein complex when the auxiliary subunit or accessory protein is not present in the expression system; calculating predetermined theoretical FRET amplitudes for one or more possible stoichiometries of the plasma membrane protein complex when the auxiliary subunit or accessory protein is present in the expression system; performing both theoretical calculations and acquiring FRET images for plasma membrane protein complexes in which only subunits absolutely required for complex assembly and function are labeled with donor and acceptor fluorophores; when the auxiliary subunit can potentially substitute for an absolutely required subunit in the complex, performing both theoretical calculations and acquiring FRET images for plasma membrane protein complexes in which the auxiliary subunits are labeled with the donor and acceptor fluorophores; when the auxiliary subunit can potentially substitute for an absolutely required subunit in the complex, performing both theoretical calculations and acquiring FRET images for plasma membrane protein complexes in which the auxiliary subunit is labeled with one of the donor fluorophore and an absolutely required subunit in the complex is labeled with the acceptor (or vice versa); if the combined influence of a compound and auxiliary or accessory protein are to be studied, all previous steps should be performed in the presence or absence of the compound of interest; the signal amplitude of each pixel in the acquired FRET images provide, a FRET distribution comprising a plurality of FRET distribution components; and calculating for each FRET distribution component a mean FRET amplitude, thus simultaneously providing a plurality of measured mean FRET amplitudes in the acquired FRET image that are compiled into a distribution of identified FRET amplitudes as a function of a number of pixels associated with each FRET amplitude; identifying in the FRET distribution one or more components, each component associated with a predetermined entity/stoichiometry; and detecting one or more mean FRET amplitudes associated with the one or more components based on the identified one or more entities/stoichiometries.

In some embodiments, time-resolved FRET measurements of single cells exposed to neurotransmitter transporter substrates, to obtain high-resolution measurements of substrate mediated neurotransmitter transporter oligomer disassembly can be performed. In some of those embodiments the method comprises: calculating predetermined theoretical FRET amplitudes for different types of transporter oligomers (FIG. 15); co-expressing transporter proteins labeled with donor or acceptor fluorophores; acquiring FRET images for assembled transporter complexes in live cells in the absence of transporter substrate; through perfusion, exchanging the substrate free imaging solution for substrate containing imaging solution in the imaging chamber and acquiring FRET images at predetermined time intervals after commencing perfusion of substrate containing imaging solution; compiling FRET distributions from the FRET images acquired at each time interval; identifying FRET distribution components and correlating the mean amplitude of each distribution component with that theoretically predetermined for each oligomer type; quantifying the fraction of the total FRET distribution represented by each of the distribution components to quantify the proportion of the total expressed oligomer population that is represented by each type of oligomer; quantifying the change in the composition of the expressed oligomer population in the presence of substrate for each time interval for which FRET images were acquired by assessing the mean FRET amplitude and the proportion of the FRET distribution comprised by each FRET distribution component; in addition to quantifying changes in the types of oligomers comprising the assembled transporter detected by FRET, a general reduction in oligomer assembly may be detected as a decrease in the number of pixels compiled in the FRET distribution. The procedures outlined above can be replicated by a skilled person to record time-resolved FRET measurements detecting either the assembly or disassembly of any other oligomer complex (e.g. G-protein coupled receptors, Cys-loop receptors, cyclic nucleotide gated channels, TRP channel super family, potassium channels, solute carrier (SLC) transporters and other multi-subunit plasma membrane proteins) in response to a physiological or pharmacological stimulus.

In some embodiments, upregulation or downregulation of an oligomer can also be associated with a biological event, including a shift towards the expression of nAChRs predominantly expressing the low agonist sensitivity $(\alpha 4)_3(\beta 2)_2$ stoichiometry in patients carrying ADNFLE mutations resulting the presentation of the nocturnal seizures for which the disease is named. Upregulation of the ADNFLE mutant channels upon exposure to nicotine results in reduced seizure frequency and normalization of the ratio of the expressed low sensitivity $(\alpha 4)_3(\beta 2)_2$ stoichiometry to the high-agonist sensitivity $(\alpha 4)_2(\beta 2)_3$ stoichiometry.

The term "associated to" as used herein with reference to two items indicates a relation between the two items such that the occurrence of a first item is accompanied by the occurrence of the second item, which includes but is not limited to a cause-effect relation and sign/symptoms-disease relation. Exemplary biomarkers include clinically informative biomarkers, and diagnostic biomarkers.

In some embodiments, a certain stoichiometry and/or related upregulation or downregulation is associated to a condition in an individual.

The term "condition" as used herein indicates a physical status of the body of an individual (as a whole or as one or more of its parts), that does not conform to a standard physical status associated with a state of complete physical, mental and social well-being for the individual. Conditions herein described include but are not limited to disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The term "individual" as used herein in the context of treatment includes a single biological organism, including but not limited to, animals and in particular higher animals and in particular vertebrates such as mammals and in particular human beings.

In those embodiments, the methods herein described can be used to select a candidate drug in treating or preventing the condition and/or identifying the one or more mutations associated to the condition.

The term "treatment" as used herein indicates any activity that is part of a medical care for, or deals with, a condition, medically or surgically.

The term "prevention" as used herein indicates any activity which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

In some embodiments, methods herein described can be used to select candidate compound for upregulation of nAChR and for use as a candidate drug in treating or preventing nicotine addiction and/or Parkinson's disease.

In some embodiments, methods herein described can be used to select candidate compound for upregulation of nAChR and for use as a candidate drug in treating or preventing Autosomal dominant nocturnal frontal lobe epilepsy (ADNFLE) (Scheffer et al., 1995; Willoughby et al., 2003; Brodtkorb and Picard, 2006). ADNFLE is linked, with high penetrance, to at least six distinct nAChR mutations in α4β2 nAChRs (Steinlein et al., 1997; Oldani et al., 1998; Combi et al., 2004; Wimmer et al., 2008). Three mutations (S247F=S6'F in the commonly used M2 domain renumbering for Cys-loop receptors), (S252L=S10'L) and (776ins3, after the 17' position) are in the channel-lining domain (M2) of the α4 subunit, while two mutations (V287L) and (V287M) are at the M2 22' position of the β2 subunit. How the ADNFLE-linked mutations cause seizures, the epileptic focus of ADNFLE seizures, and other basic pathophysiological aspect remain unresolved (Wong et al., 2002; Teper et al., 2007); (Figl et al., 1998; Rodrigues-Pinguet et al., 2003; Rodrigues-Pinguet et al., 2005); (Steinlein et al., 1997).

In some embodiments, methods herein described can be used to select candidate compound for downregulation of nAChR and for use as a candidate drug in treating or preventing smoking and nicotine addiction. In the present disclosure it is shown that nicotine is associated with nAChR upregulation and to the corresponding α4β2 stoichiometry. Screening of candidate compounds that are able to downregulate the nAChR would provide candidate drugs for treatment and/or prevention of smoking and/or nicotine addiction.

In some embodiments, methods herein described can be used to select nicotinic subtype-specific nAChR upregulators that could have the desired effects of nicotine without, the adverse gastrointestinal and cardiovascular side effects that occur due to off-target activation of nAChRs, and preclude nicotine as a therapeutic drug (Wu and Cho, 2004; Hanna, 2006). Those subtype specific nAChR upregulators able to cause a controlled and targeted upregulation of the appropriate neuronal nAChR subtypes are expected to circumvent nicotine-induced side effects and to be suitable as therapeutic drugs. In particular, nicotinic subtype specific nAChR capable of affecting the processes that selectively modulate the chaperoning, stoichiometry and channel number expressed, are expected to operate in the ER (Lester et al., 2009). Nicotinic drugs are expected to be effective pharmacological chaperones by acting in the ER. Fluorescence-based analyses of nAChR assembly, trafficking, and stoichiometry are in principle suitable for drug discovery for compounds that influence channel properties by acting in intracellular regions.

In some embodiments, methods herein described can be used to select candidate compounds for use as a candidate drugs in treating or preventing parasitic nematode infections, such as infection of pigs by the gastrointestinal parasite *Ascaris suum* (Stewart and Hale, 1988) and human parasite *Ascaris lumbricoides* (Crompton, 2001; Bethony et al., 2006). Previous studies show that nicotine and levamisole preferentially activate N- and L-type nAChRs respectively in both nematode species, whereas the N-type is a homo-pentamer of a sixth subunit (Touroutine et al., 2005); (Williamson et al., 2007) (Williamson et al., 2009). Fluorescent assays that directly report the stoichiometry of nematode nAChRs are expected to enhance the understanding of antihelmintic drug targets and hasten the potential development of parasite-specific antihelmintic compounds.

In some embodiments, FRET detection can be used to detect interactions of protein complexes or their relevant subunits with another protein. In particular, in some embodiments one or more stoichiometries of the protein complex can be detected with a method herein described and identification of a mean FRET efficiency or a pixel-by-pixel FRET efficiency uncorrelated with the theoretically calculated FRET efficiencies indicates interaction with of the protein complex with the another protein. In particular, in some embodiments, extra components, can be detected in the experimental FRET distributions that are additional to the components of the FRET distributions that can be matched to theoretically calculated FRET amplitudes for each possible stoichiometry which for example are caused by interaction of oligomers with cytosolic or cytoskeletal complexes.

The methods herein described can be performed with the aids of a computer-readable medium that contains a set of instructions that causes a computer to perform at least one of the methods herein described. An exemplary software is described in Feige et al (2005) herein incorporated by reference in its entirety. An additional exemplary software is provided by written ImageJ macros that can be used to enable assembly of the image stacks ready for analysis and Matlab macros that compile all the pixels from each dataset into a single FRET distribution.

The computer-readable medium can also be included in a computer. In some embodiments, the computer can be the same machine included in the confocal imaging system that acquired the data to allow immediate processing of the newly acquired data.

In some embodiments, the methods herein described can be performed using a system for detection of one or more stoichiometries in a protein complex. In particular, the system provides at least two between a cell line capable of expressing a protein complex of interest; an expression plasmid capable of expressing fluorescently labeled subunits of the protein complex of interest; a computer readable medium herein described and confocal imaging elements.

Further details concerning the implementation of the methods herein described including systems for performance of the methods which can be in the form of kit of parts as well as related compositions including donors, acceptors, compounds and other reagents together with suitable carrier agent or auxiliary agent of the compositions, and generally manufacturing and packaging of the kit, can be identified by the person skilled in the art upon reading of the present disclosure.

EXAMPLES

The methods and system herein disclosed are further illustrated in the following examples, which are provided by way of illustration and are not intended to be limiting.

In particular, the following examples illustrate exemplary stoichiometry detection of nicotinic receptor nAChRs and related analysis according to exemplary methods and systems of the present disclosure. A person skilled in the art will appreciate the applicability of the features described in detail for nAChRs for additional compounds having geometries constraint according to the present disclosure.

The following materials and methods were used in various experimental procedures illustrated in the following Examples.

pEYFP-C1 or pECFP-C1 vectors were purchased from Clontech (Mountain View, Calif.). PfuTurbo $C_x$ Hotstart polymerase and the QuikChange II XL site-directed mutagenesis kit was purchased from Stratagene (La Jolla, Calif.). The mouse neuroblastoma 2a (N2a; CCL-131) and the human embryonic kidney T/17 cell line (HEK 293T; CRL-11268) were obtained from ATCC (Manassas, Va.).

The pcDNA3.1(+) expression vector, fetal bovine serum (FBS), Lipofectamine and Plus reagents were purchased from Invitrogen (Carlsbad, Calif.). Penicillin/Streptomycin 100× and Sodium Pyruvate 100× solutions were purchased from Mediatech (Herndon, Va.). Culture dishes (35 mm, with 14 mm No. 0 glass coverslip microwells) were purchased from Mattek (Ashland, Mass.). Other tissue-culture plasticware was purchased from Greiner Bio-One (Monroe, Calif.). Acetylcholine chloride (ACh), nicotine and all other reagents were purchased from SigmaAldrich (St. Louis, Mo.).

Example 1

Selection of Cell Type and Cell Culture Methods for nAChRs Expression and Analysis Mouse neuroblastoma 2a cells (N2a) cells were used to heterologously express nAChRs for several reasons: (i) N2a cells are neuron-like and can be differentiated into neuronal populations. In addition, human SH-SY5Y neuroblastoma cells express native nAChRs (Innocent et al., 2008). These factors increase the likelihood that N2a cells possess chaperoning proteins and neuron-specific factors required for efficient nAChR assembly and trafficking. (ii) The inventors' laboratory has compared human embryonic kidney (HEK293) and N2a cells for expression and function of the GABA transporter, GAT1. Results from these studies show that when compared to HEK293 cells, N2a cells heterologously express transporters in a non-saturated manner and that the expression levels correlate well with transporter function (Moss et al., 2009). (iii) N2a cells were successfully used before for whole cell electrophysiology as well as FRET and TIRFM studies of transiently expressed nicotinic receptors (Drenan et al., 2008; Son et al., 2009). The well established imaging methods in N2a cells are applicable to primary neurons expressing fluorescent nAChRs to confirm relevance of the findings from the N2a cell line to a native cellular environment.

In the experimental procedures illustrated in the present disclosure N2a cells were cultured at 37° C. in 95% air, 5% $CO_2$ in medium composed of 44.5% DMEM, 44.5% Opti-MEM1, 5% FBS, 100 I.U./ml penicillin and 100 µg/ml streptomycin. For all experiments, cells were plated onto poly-d-lysine coated 35 mm culture dishes with 14 mm glass bottoms. Transfections were performed using a modification of the manufacturer's Lipofectamine and Plus reagent protocol, resulting in non-saturated expression levels of nAChRs (Imoukhuede et al., 2009; Moss et al., 2009; Son et al., 2009). Nicotine at 1 µM final concentration was added to the appropriate dishes (nicotine was replenished with each media change).

Example 2

Selection of Fluorescent Moieties and Identification of an Optimal FRET Pairs According to Experimental Design eCFP and eYFP moieties (the term XFP will henceforth be used to collectively describe fluorophores derived from the green fluorescent protein, GFP, and the fluorophore, mCherry) were selected for performing experimental procedures directed to detect upregulation of α4 and β2 nicotinic receptor illustrated in the following examples.

Mouse α4 and β2 nAChR subunits fused in frame to eCFP and eYFP moieties are used by Applicants' lab to study receptor upregulation, functional assembly and trafficking in transfected HEK293 cells, N2a cells as well as primary neuronal cultures (Nashmi et al., 2003; Drenan et al., 2008). The general schematic depicted in FIG. 1 describes the site of insertion of the fluorophores into either the α4 or β4 nAChR subunit coding sequences. Additional details on the experimental procedures used to provide the construct of FIG. 1 are illustrated in Examples 3 and 4.

With eCFP and eYFP, one can optically monitor (usually in real time and in living cells) (i) subcellular distribution and co-localization in neurons using confocal microscopy and spectral imaging (Nashmi et al., 2003; Nashmi et al., 2007); (ii) receptor assembly and subunit stoichiometry using FRET (Drenan et al., 2008), and (iii) plasma membrane localization and distribution patterns using total internal reflection fluorescence (TIRF) microscopy (Drenan et al., 2008). Applicants continue to develop a collection of fluorescent α4 and β2 constructs to include versions of each nAChR subunit fused with the mCherry and meGFP fluorophores (Shaner et al., 2004; Shaner et al., 2005). These optimized variants possess greater photostability, fluorescence intensity, are monomeric in structure and give rise to highly efficient FRET pairs. All the XFPs used in the investigations exemplified herein possess a monomerizing (m=monomeric) A206K mutation that prevents potential FRET artifacts occurring due to XFP dimerization (Zacharias et al., 2002). The mCherry and meGFP FRET pair displayed significantly reduced variability (~12% coefficient of variation) compared to other XFP pairs (FIG. 2) making them ideally suited for recording pixel-by-pixel FRET measurements by sensitized emission.

Example 3

α4β2 nAChRs Constructs Comprising eCFP and eYFP Fluorescent Labels

Plasmids for wild-type mouse α4 and β2 nAChR cDNAs were provided by Jerry Stitzel (University of Michigan, Ann Arbor, Mich.) and the construction of fluorescent α4YFP, α4CFP and β2YFP, β2CFP nAChR subunits has been described (Nashmi et al., 2003) (FIG. 1A). Fluorescent ADNFLE mutants were generated in QuikChange II XL mutagenesis PCR reactions from the WT α4XFP and β2XFP plasmids using the primer pairs described in the manual available at the web page stratagene.com/manuals/200516.pdf For each construct, the entire open reading frame and its flanking regions were sequenced. The primers used are reported in Table 1 below.

TABLE 1

| Primer Name | Primer Sequence | SEQ ID NO |
|---|---|---|
| S248F Forw. | 5' GCATCTTCGTGCTGCTTTCTCTCACCGTCTTCCTGCTGC 3' | 17 |
| S248F Rev. | 5' GCACCGAGATGCACAGCGTGACCTTCTCGCCGCACTCC 3' | 18 |
| S252L Forw. | 5' GCTTTTGCTCACCGTCTTCCTGCTGCTCATCACCGAG 3' | 19 |
| S252L Rev. | 5' CGGTGAGCAAAAGCAGCACCGAGATGCACAGCGTGACC 3' | 20 |
| 776ins3 Forw. | 5' GCTCCTGATCACCGAGATCATCCCGTCCACCTCGCTGG 3' | 21 |
| 776ins3 Rev. | 5' CGGTGATCAGGAGCAGCAGGAAGACGGTGAGAGAAAGC 3' | 22 |
| V287L Forw. | 5' CCAAGATTCTGCCTCCCACCTCCCTCGACGTACCGCTGG 3' | 23 |
| V287L Rev. | 5' GGGAGGCAGAATCTTGGAGATGAGCAGCAGGAACACCG 3' | 24 |
| V287M Forw. | 5' CCAAGATTATGCCTCCCACCTCCCTCGACGTACCGCTGG 3' | 25 |
| V287M Rev. | 5' GGGAGGCATAATCTTGGAGATGAGCAGCAGGAACACCG 3' | 26 |

Example 4

γ-Aminobutyric Acid Transporter (mGAT1) Constructs Comprising eCFP and eYFP Fluorescent Labels Nineteen new fluorescent mGAT1 constructs to study trafficking and oligomerization of the GAT1 transporter were generated. The goal was to generate fluorescent mGAT1 proteins that (a) assembled and trafficked as wild-type, and (b) gave robust Förster resonance energy transfer (FRET) efficiencies when the transporter oligomerized. Wild-type mGAT1 and mGAT1$_0$GFP constructs have been described previously (Chiu et al., 2002). The new fluorescent mGAT1 constructs described in this study were designed to rectify trafficking deficits of mGAT1$_0$GFP; and in addition, Applicants exchanged the GFP fluorophore for ECFP or EYFP containing the "monomeric" A206K mutation to avoid distortions caused by dimerization motifs within the ECFP and EYFP proteins (Zacharias et al., 2002) and to facilitate the study of protein-protein interactions by FRET.

To generate the fluorescent mutants mGAT1$_0$XFP and mGAT1XFP* through mGAT1XFP45, the wild-type mGAT1 open reading frame (ORF) was subcloned without its original stop codon into the Hind III and EcoR I sites of the pcDNA3.1 (+) expression vector multiple cloning site (MCS). XFP ORFs were then subcloned downstream from and in frame with the mGAT1 ORF at the Not I and Xba I sites of the pcDNA3.1(+) MCS. This resulted in a 12 amino acid spacer between the end of the mGAT1 sequence and the beginning of the fluorophore. Applicants modified a method for the integration of PCR fragments without the use of restriction enzymes (Geiser et al., 2001) to add the final 3, 8, 20, 28 or 45 codons of the hGAT1 ORF. These were amplified from a source plasmid using the proof-reading PfuTurbo C$_x$ Hotstart polymerase with 5' and 3' extensions corresponding to the 20-22 nt regions that flanked the intended site of insertion such that the PCR product integrated in frame immediately after the fluorophore sequence when the primers were used in a subsequent QuikChange II XL mutagenesis PCR reaction. For mGAT1XFP*, Applicants simply added a GTC codon for Val after the fluorophore ORF.

Figure 2:
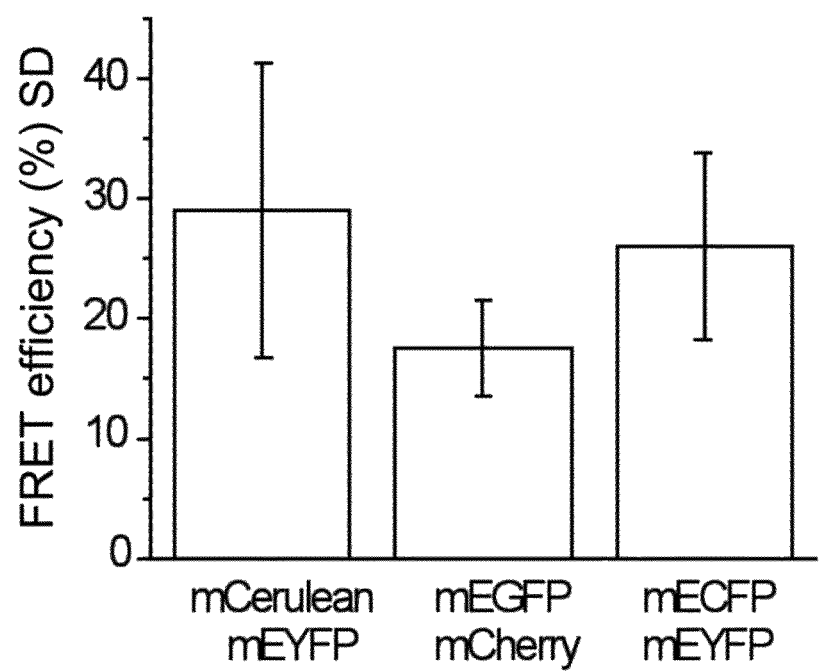
FIG. 2 shows: Comparison of FRET measurements with donors (mCerulean, mECFP, or mEGFP) in the β2 subunit and acceptors (mEYFP, mEYFP, or mCherry) in the α4 subunit. The experiments utilize acceptor photobleach FRET. Note that the mEGFP-mCherry fluorophores give the lowest coefficient of variation among cells.

FIG. 1B displays the protein sequences of the modified regions of mGAT1 for each fluorescent construct. mGAT1$_0$CFP and mGAT1$_0$YFP repeated the fusion design of mGAT1$_0$GFP but with the fluorophore exchanged as annotated. The three C-terminal residues of the mGAT$_0$XFP fusions are -YKI-CO$_2^-$ which comprises a broadly defined consensus PDZ class II interacting motif (X-φ-X-φ, where φ designates a hydrophobic residue and X any residue (Sheng and Sala, 2001; Hung and Sheng, 2002)). Applicants searched the Ensembl databases using Biomart (see web page ebi-.ac.uk/biomart (Spudich et al., 2007)) and applied the GO:0005886 "plasma membrane" cellular component filter. The search identified no known membrane proteins possessing the —YKI-CO$_2^-$ C-terminal sequence. In the mGAT1XFP* constructs Applicants defined the terminal residue P(0) more narrowly, changing the terminal isoleucine residue present in mGAT1$_0$XFP to a valine in mGAT1XFP* (FIG. 1B). The resulting C-terminal sequence, —YKV-CO$_2^-$ reconstituted a functional PDZ class II interacting motif present in Ephrin B receptors, a class that rely on interactions with PDZ domain containing proteins for clustering (Torres et al., 1998; Bruckner et al., 1999; Lin et al., 1999; Madsen et al., 2005). Other constructs in the C-terminal XFP fusion series, mGAT1XFP3, mGAT1XFP8, mGAT1XFP20, mGAT1XFP28 and mGAT1XFP45, had the most C-terminal 3, 8, 20, 28 or 45 residues of human GAT1 (hGAT1) appended after the mGAT1XFP fusion (FIG. 2). The differences in nucleotide sequence between the hGAT1 and mGAT1 C-termini were a useful source of positive identification when Applicants analyzed the clones during construction.

PCR integration was applied to amplify and insert EYFP or ECFP directly between residues R565 and L566, I570 and Q571, or V577 and R578 of mGAT1 to generate the mGAT1$^{5xx}$XFP$^{5xx}$CT constructs (FIG. 1B). The site of XFP insertion in GAT1 is highlighted in the nomenclatures for these constructs by superscript residue numbers flanking the fluorophore, and the "CT" denotes that the insertion occurs within the C-terminus.

Example 5

Image Detection by Confocal Imaging

Live cells were grown on 14 mm glass bottomed Mattek 35 mm culture dishes pre-coated with poly-d-lysine are washed twice with 37° C., pH 7.4 extracellular buffer (150 mM NaCl, 4 mM KCl, 10 mM HEPES, 2 mM MgCl$_2$, 2 mM CaCl$_2$, 10 mM glucose) and observed in the same solution. Live cells were imaged at room temperature on an Eclipse C1si laser scanning confocal microscope equipped with a 63×, 1.4 numerical aperture VC Plan Apo oil objective and a 32-anode photomultiplier tube (PMT) (Nikon Instruments Inc., Melville, N.Y.).

When required, images were linearly unmixed using the EZ-C1 software (Nikon) for the emission spectra of the fluorophores of interest using reference spectra individually compiled for each fluorophore expressed in the same cell type and imaged under identical experimental conditions.

Example 6

Image Acquisition by Acceptor Photobleach FRET

N2a cells were visualized at room temperature in extracellular buffer, 48 h after transfection. A series of lambda stack X-Y images were collected with the Eclipse C1si laser scanning confocal microscope according to procedures exemplified in Example 5. Dequenching of CFP fluorescence during incremental photobleaching of YFP was performed and analyzed as previously described (Nashmi et al., 2003; Drenan et al., 2008). FRET efficiency (E) was calculated according to (Equation 1).

$$E = 1 - \left(\frac{I_{DA}}{I_D}\right) \quad \text{(Equation 1)}$$

$I_{DA}$ represents the normalized fluorescence intensity of the donor (100%) in the presence of non-bleached acceptor. $I_D$ represents the normalized fluorescence intensity of the donor following 100% photobleach of the acceptor. The $I_D$ value was extrapolated from a scatter plot of the percentage increase of donor intensity versus the percentage decrease of acceptor intensity for each cell (Nashmi et al., 2003).

Example 7

Imaging Acquisition Using Pixel-by-Pixel FRET from Sensitized Acceptor Emission

Live cells were imaged using the Eclipse C1si laser scanning confocal microscope according to procedures exemplified in Example 5. Full emission spectra images are acquired in 5 nm bins between 450 nm and 610 nm, linearly unmixed using reference spectra from samples expressing solely the donor- or acceptor-tagged fusion constructs to unambiguously separate the donor and acceptor signal from each pixel of the spectral images.

Live cells are imaged using the Eclipse C1si laser scanning confocal microscope. Full emission spectra images are acquired in 5 nm bins between 450 nm and 610 nm, linearly unmixed using reference spectra from samples expressing solely the donor- or acceptor-tagged fusion constructs to unambiguously separate the donor and acceptor signal from each pixel of the spectral images. Transfections of cells expressing only the donor- or acceptor-tagged fusion protein are performed for every imaging session to control for pixel saturation and spectral bleedthrough (SBT). Where appropriate, non-fluorescent subunit cDNAs are included in the transfection to ensure the faithful expression and subcellular localization of the single fluorescent species. Control samples expressing only the donor-fused constructs are imaged with the appropriate laser line and unmixed with acceptor and donor emission spectra. The unmixed acceptor images are termed the $FRET_d$ channel, and the fluorescence intensity of each pixel is termed ($I_{FRETd}$). The donor fluorophore images are the "Donor" channel and pixel intensities are described by $I_{donor}$. A montage of all the $FRET_d$ channel images and a second montage of all the Donor channel images are assembled and compiled into an image stack called the "Donor SBT stack" in the order $FRET_d$ channel, Donor channel.

Two spectral images of each cell expressing only the acceptor-fused constructs are acquired, the first excited by the donor specific laser line and the second with the acceptor specific laser line. The acceptor fluorophore signal is unmixed from each image. A montage of the unmixed donor specific laser line excited acceptor images termed the $FRET_a$ channel (pixel intensities=$I_{FRETa}$) is assembled and compiled with a montage of the acceptor specific laser line excited images termed the Acceptor channel (pixel intensities=$I_{acceptor}$) and called the Acceptor SBT image stack. The Pix-FRET ImageJ plug-in is used determine the donor and acceptor bleed-through values and to calculate the net FRET (nF) and NFRET in each pixel (Feige et al., 2005). With the background and bleed-through corrections set, the nF for each pixel as described by Eq. 2 is calculated and the data output as 32-bit images.

$$nF = I_{FRET} - I_{donor} \times BT_{donor} - I_{acceptor} \times BT_{acceptor} \quad \text{(Equation 2)}$$

nF is normalized for donor and acceptor expression levels according to Eq. 3 to calculate NFRET and to generate a 32-bit NFRET image (Xia and Liu, 2001).

$$NFRET = \frac{I_{FRET} - I_{donor} \times BT_{donor} - I_{acceptor} \times BT_{acceptor}}{\sqrt{I_{donor} \times I_{acceptor}}} \quad \text{(Equation 3)}$$

Normalizing nF to the square root of the product of the donor and acceptor fluorescence intensities controlled for large variations in the expression levels of each fluorophore between different cells and provided a measure of FRET that is readily comparable between different samples (Xia and Liu, 2001). Gordon et al. (1998) explained that NFRET is a relative measure of the dissociation constant ($K_d$) for the binding interaction between proteins that increases monotonically (but not linearly) at smaller values of $K_d$. All-pixel NFRET amplitude distributions for a given collection of cells, or of subregions, are summarized as histograms with a bin size of 0.02 NFRET units. Fitting of NFRET distributions with Gaussian components concluded when $R^2 \geq 0.99$.

To calculate FRET efficiency from sensitized emission experiments, Eq. 1 was modified because it was not possible to directly measure $I_D$ from such samples. Because the sensitized emission of the acceptor is due to the quenching of the donor in the presence of the acceptor, $I_D$ can be substituted in Eq. 1 by adding the nF signal amplitude to the amplitude of the donor fluorescence in the presence of acceptor $I_{DA}$ (Elangovan et al., 2003). Thus, we calculated FRET efficiency E as $$E = 1 - \left(\frac{I_{DA}}{I_{DA} - nF}\right), \quad \text{(Equation 4)}$$

Example 9

Predetermination of FRET Amplitudes Associated with α4β2 nAChR Subunit Stoichiometries The FRET efficiency associated to each stoichiometry of α4β2 nAChR was predetermined by the analysis illustrated below.

The analysis was performed using several simplifying geometric assumptions. (1) In a functional α4β2 receptor, there are at least two agonist binding sites at the α-β subunit interfaces (these are polarized, requiring particular faces of each subunit; see assumption 2 below). Therefore, in the $(α4)_2(β2)_3$ stoichiometry, the two α4 subunits are non-adjacent; and in the $(α4)_3(β2)_2$ stoichiometry, the two β2 subunits are non-adjacent. (2) In the diagrams of FIG. 3A and FIG. 3B the receptor is viewed from the extracellular faces, so that the β subunit is adjacent, in the clockwise direction, to the α subunit. (3) Although the intracellular domain of the α4 subunit has roughly twice as many amino acids as that of the β2 subunit, the fluorophores are positioned in an equilateral pentagonal structure. (4) All α4 subunits are radially equivalent; and all β2 subunits are radially equivalent. (5) Because the CFP donor and YFP acceptor differ by only 9 amino acids, YFP-fused and CFP-fused subunits are synthesized with equal efficiency and assemble randomly within receptor pentamers. The expected results are rather insensitive to departures from this assumption by even two-fold. (6), Again because YFP and CFP differ only subtly, the structure of an α4CFP subunit is the same as α4YFP; also a β2CFP subunit has the same structure as a β2YFP subunit. (7) In a rigorous analysis, the dipole orientation factor $κ^2$ differs between adjacent and non-adjacent subunit pairs. Analysis shows that, in general, the ratio $κ^2$ (non-adjacent subunits)/$κ^2$ (adjacent subunits) lies between 1 and 2; a full prediction requires knowledge of the dipole orientation, which we do not know (Corry et al., 2006). For the purpose of this determination the assumption was that this ratio always equals 1.

In such a pentameric receptor, there are two possible distances between fluorophores: a, the side length between adjacent subunits; and b, the diagonal between non-adjacent subunits (FIG. 3A). These are given by:

$$b/a = (1+\sqrt{5}/2) = 1.618 \quad \text{(Equation 5)}$$

Thus the efficiencies of energy transfer within an isolated pentameric receptor can be calculated analytically depending on the position of the donor and the acceptor. Most measurements in this study use the simple case in which the fluorophores are present in all α4 subunits, but none of the β2 subunits, or vice-versa. To simplify the terminology, the case for fluorescent α4 subunits was explicitly analyzed; the results was of course considered to apply, to the fluorescent β2 case as well.

For the $(α4)_2(β2)_3$ stoichiometry, the fluorophore separation is the non-adjacent value, b. Therefore the FRET efficiency is $$E_b = \left( \frac{(R_0/B)^6}{1+(R_0/b)^6} \right); \quad \text{(Equation 6)}$$

and the statistical factors are rather simple: 50% of the molecules have heterogeneous fluorophores and therefore display FRET (our methods do not determine homo-FRET) (FIG. 3B).

The situation is more complex for the $(α4)_3(β2)_2$ pentamer (FIG. 3B). For instance, the FRET efficiency for one donor, non-adjacent to two acceptors, is $$E_1 = \left( \frac{2(R_0/b)^6}{1+2(R_0/b)^6} \right); \quad \text{(Equation 7)}$$

for one donor, adjacent and non-adjacent to two acceptors, E is $$E_2 = \left( \frac{R_0^6 \left( \frac{1}{a^6} + \frac{1}{b^6} \right)}{1 + R_0^6 \left( \frac{1}{a^6} + \frac{1}{b^6} \right)} \right); \quad \text{(Equation 8)}$$

for two donors, both non-adjacent to a single acceptor, E is simply $$E_3 = E_b. \quad \text{(Equation 9)}$$

For two donors, one adjacent and the other non-adjacent to a single acceptor, $$E_4 = \frac{1}{2} \left( \frac{\left(\frac{R_0}{a}\right)^6}{1+\left(\frac{R_0}{a}\right)^6} + \frac{\left(\frac{R_0}{b}\right)^6}{1+\left(\frac{R_0}{b}\right)^6} \right). \quad \text{(Equation 10)}$$

The total FRET efficiency is now the weighted sum of E for a particular configuration, times the probability that the configuration occurs. These statistical factors are given in FIG. 3B (Corry et al., 2005).

These calculations led to an expected series of FRET efficiencies as a function of the distance a between adjacent fluorophores (FIG. 3C). Note that the FRET efficiency does not approach 1 as a approaches 0, because in some pentamers, all tagged subunits carry either donors or acceptors, in which case our measurement cannot detect FRET. Because 25% of the assembled receptors are composed of three tagged subunits and 50% of the receptors carrying two tagged subunits lack FRET partners, the FRET efficiency curves in FIG. 3C intersect the y-axis between 75% and 50%.

The final step in the theoretical analysis (FIG. 3D) was to assume a reasonable value for the distance a between adjacent fluorophores. In the absence of structural data for the intracellular loop of any Cys-loop receptor, this must be a guess. We assume a value of a=52 Å, which is also consistent with structural studies of the neuromuscular receptor (Unwin, 2005). However any distance within ~40 Å and ~60 Å would generate the same conclusion: FRET efficiencies are quite measurable (10%-40%) if all the pentamers have the $(α4)_3(β2)_2$ stoichiometry. The solid line In FIG. 3D shows that, as the percentage of $(α4)_3(β2)_2$ decreases to zero (with a complementary increase of $(α4)_2(β2)_3$), the theoretical FRET efficiency drops by ~10 fold.

For any chosen value of a, the theoretical FRET efficiency depends linearly on the percentage of $(α4)_3(β2)_2$ stoichiometry. For a=45 Å, the maximum and minimum FRET values are 29.3% and 4.8%, respectively; for a=60 Å, these extremes are 10.6% and 0.9%, respectively.

Example 10

Confirmation by Fluorescence Intensity Ratio of Predetermined FRET Values for Stoichiometries of α4β2 Nicotinic Receptor The predetermined values identified using the analysis reported in Example 9 were confirmed by fluorescence intensity ratio determination.

Fluorescence intensity ratio (FIR) analysis provides information to define the subunit stoichiometry of most heteromeric channel types. The method is based on fluorescently tagged subunits and was first reported (Zheng and Zagotta, 2004) to determine the subunit stoichiometry of olfactory cyclic nucleotide-gated channels. The studies illustrated herein used the same YFP- and CFP-tagged α4 and β2 subunits used in the FRET studies. However, whereas the FRET studies employed 1:1 ratios of α4CFP:α4YFP (or the β2 equivalents), the FIR studies used two sets of cDNAs: (1) mixtures of α4CFP and β2YFP cDNAs, or (2) α4YFP and β2CFP cDNAs. Since the channel subunit and the fluorescent protein are covalently linked, the molar ratio between CFP and YFP molecules is the same as the molar ratio between the subunits in which they are inserted. To correct for different excitation laser intensities and different extinction coefficients and quantum yields of the fluorophores, a similar measurement was carried with set 1 and set 2. By comparing the two fluorescence ratios, the correction factor to account for the different intensities of the individual fluorophores was calculated and thereby also the ratio of subunits.

There are potential concerns with the FIR method. (a) FRET may occur between channel subunits. FIR assumes that fluorescence emission of CFP and YFP are independent. Considering the close proximity of channel subunits, this assumption is not true in most cases due to FRET between these fluorophores. (b) There may unassembled subunits present. (c) There may be degraded subunits, producing soluble CFP and YFP. Points (b) and (c) Would contribute to the fluorescence intensities measured, thus obscuring the subunit ratios calculated for the assembled channels. To overcome these complications, an analysis was used that the Applicants named "FRET-defined FIR" to calculate the nAChR subunit stoichiometry. FRET-defined FIR assumes that FRET occurs only in fully assembled receptors, and that partially assembled receptors, free subunits, or free fluorophores do not contribute appreciable FRET.

For simplicity, in the present example Applicants define α=α4 and β=β2. When CFP-tagged α subunits and YFP-tagged β subunits are co-expressed, the intensities of CFP and YFP can be calculated as $F_{CFP}=C_1[\alpha]$ and $F_{YFP}=C_2[\beta]$, where $F_{CFP}$ and $F_{YFP}$ are CFP and YFP intensities calculated by acceptor photobleaching. Thus, $F_{CFP}$ corresponds to the dequenched CFP intensity when 100% of the acceptor molecules are bleached; this represents CFP carrying subunits participating in assembled pentamers with YFP containing subunits. Similarly $F_{YFP}$ detected by exciting CFP at 439 nm and detecting the YFP emission due to FRET, arises from YFP containing subunits participating in assembled pentamers with CFP containing subunits.

Both intensities were detected by spectral imaging and unmixed to eliminate background fluorescence and the overlap of emission spectra. The [α] and [β] are the number of αCFP and βYFP subunits.

The constants $C_1$ and $C_2$ include the laser intensities, the system transfer function, the properties of the fluorophores, and other factors. But $C_1$ and $C_2$ are independent of the subunit (α vs β) hosting the fluorophore. The FIR $$k_1 = \frac{F_{CFP}}{F_{YFP}} = C\frac{[\alpha]}{[\beta]}, \quad \text{(Equation 11)}$$

where $C=C_1/C_2$. Similarly, coexpressing αYFP and βCFP subunits yields an FIR $$k_2 = \frac{F_{CFP}}{F_{YFP}} = C\frac{[\beta]}{[\alpha]}. \quad \text{(Equation 12)}$$

Therefore, both the subunit ratio and the parameter C were determined using the following equations:

$$\frac{[\alpha]}{[\beta]} = \sqrt{k_1/k_2}; \quad \text{(Equation 13)}$$

$$C = \sqrt{k_1 k_2} \quad \text{(Equation 14)}$$

Once C was experimentally determined for our optical system, $k_1$ and $k_2$ were calculated for any given subunit ratio. Comparison of the experimental data with these calculated values revealed the subunit stoichiometry under the experimental conditions.

Example 11

Determination of α4β2 nAchR Stoichiometry from Images Acquired by Acceptor Photobleach FRET The predetermined FRET amplitudes determined using procedures exemplified in Example 9 and confirmed with the FIR analysis of Example 10 were used to determine stoichiometry in images acquired using FRET acceptor photobleaching using procedures exemplified in Example 6.

Figure 3:
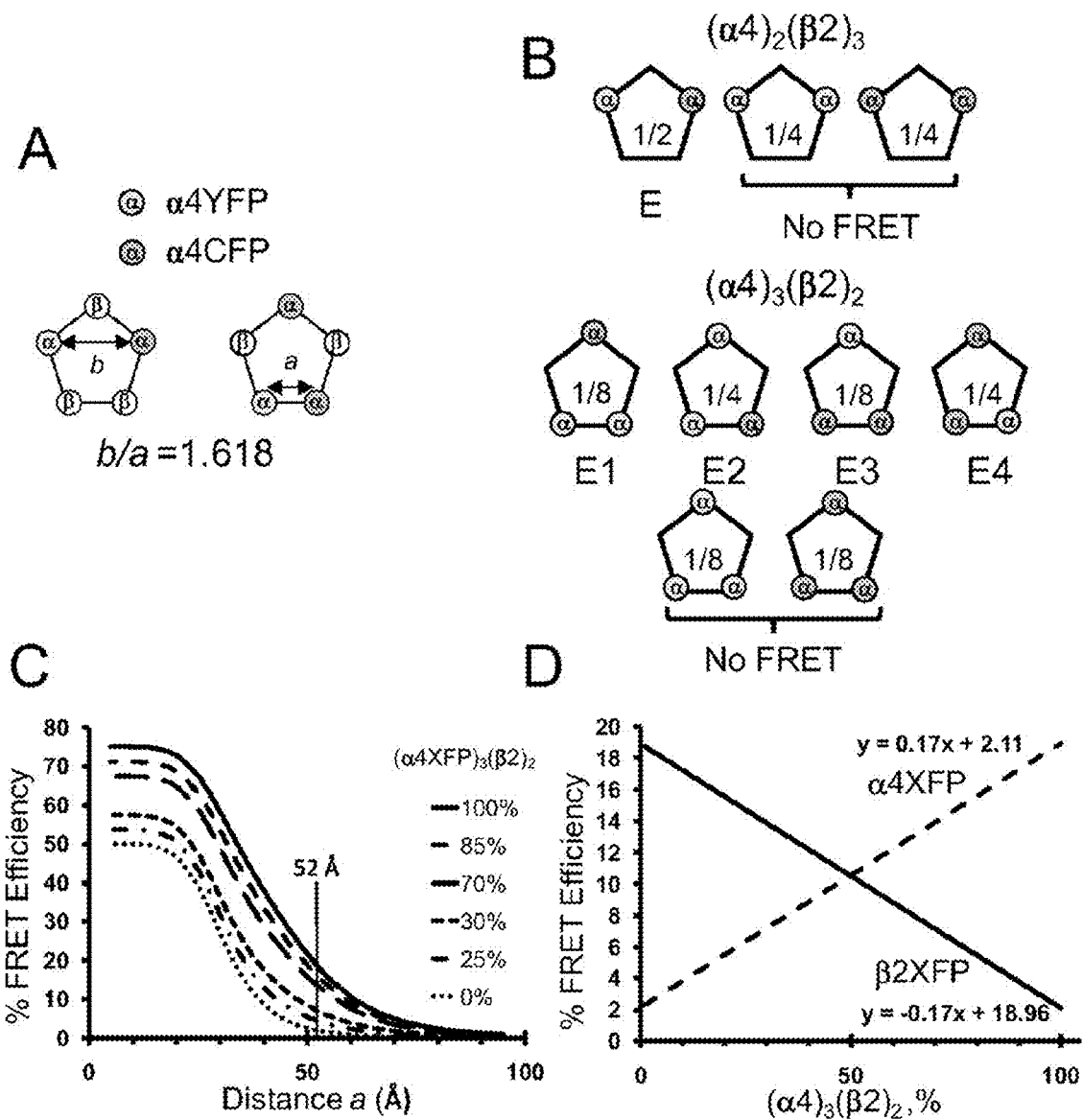
FIG. 3 shows: Assumptions and calculations underlying the FRET analyses. A, in a pentamer, there are two possible distances between fluorophores: "a," the side length of the pentagon, and "b," the diagonal between nonadjacent subunits. See Eq. 5. B, fractional prevalence of various arrangements when two or three tagged subunits are present in pentameric nAChRs. FRET efficiencies E, E1, E2, E3, and E4 are given in Eqs. 6 to 10 (Corry et al., 2005). C, theoretical FRET efficiency versus distance a between adjacent fluorophores in α4 subunits, for α4β2 receptor populations containing several overall stoichiometric ratios of α4 to β2. Calculations use Eqs. 8 to 10 plus the known statistical factors (Corry et al., 2005). For the CFP-YFP pair, the Förster distance, $R_0$=50 Å. Note that x-axis is defined by the length of a side rather than the definition given by FIGS. 10 and 12 of Corry et al. (2005). D, dashed line, calculated FRET efficiency for fluorescent α4 subunits, versus percentage of receptors with $(α4)_3(β2)_2$ stoichiometry (the balance of pentamers would be $(α4)_2(β2)_3$). The solid line provides the complementary calculation for receptors with fluorescent β2 subunits. The calculations assume that the separation between adjacent fluorophores, a=52 Å (vertical line in C).

The calculations and analyses presented above, and summarized by FIG. 3 show that when (a) only the α4 subunits are fluorescently tagged with a 1:1 molar ratio of CFP and YFP, and (b) the $(\alpha 4)_3(\beta 2)_2$ receptor stoichiometry predominates, a robust FRET is expected. Upon a shift towards the $(\alpha 4)_2(\beta 2)_3$ stoichiometry, a lower FRET efficiency is expected. These expected differences in FRET arise because, in a pentamer containing three α4 subunits, two are adjacent. Because the FRET efficiency approaches a $1/R^6$ dependence as fluorophores are separated, our assumptions lead to a much higher FRET efficiency in this case. Similarly, (a) when only the β2 subunits are fluorescently tagged with a 1:1 molar ratio of CFP and YFP, and (b) when the $(\alpha 4)_2(\beta 2)_3$ receptor stoichiometry predominates, one expects a higher FRET efficiency.

Cells often produce a mixture of these $(\alpha 4)_2(\beta 2)_3$ and $(\alpha 4)_3(\beta 2)_2$ receptors (Buisson and Bertrand, 2001; Nashmi et al., 2003; Nelson et al., 2003), although they can be manipulated to express a nearly pure population of one or the other (Nelson et al., 2003; Briggs et al., 2006). An N2a cell expression system was optimized to produce controlled, nonsaturated expression of membrane proteins, suitable for fluorescence studies (Drenan et al., 2008; Imoukhuede et al., 2009; Moss et al., 2009). N2a cells were transfected with various ratios of subunit cDNA, to force the receptor population towards a mostly $(\alpha 4)_3(\beta 2)_2$ or $(\alpha 4)_2(\beta 2)_3$ stoichiometry (Nelson et al., 2003). As typically found for nAChRs, there was little or no membrane-localized fluorescence at the cell periphery in any of the images of this study; therefore most of the fluorescence arises from intracellular receptors.

Figure 4:
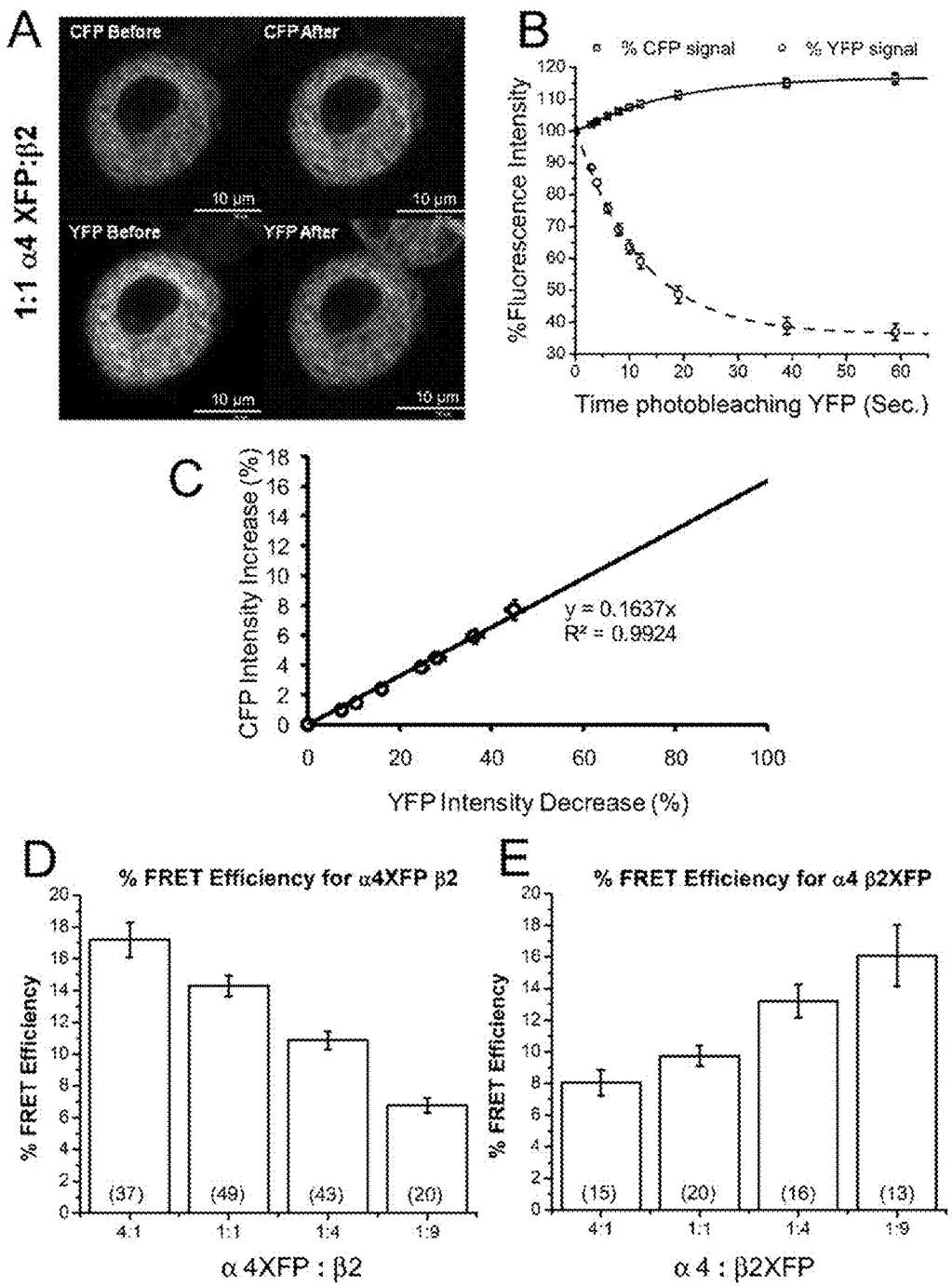
FIG. 4 shows: Spectral images acquired before and after YFP bleaching were unmixed to calculate percent increase and decrease in CFP and YFP fluorescence intensities, respectively. A, representative unmixed images of a single N2a cell expressing 1:1 transfection ratio of α4XFP:β2 cDNAs before and after photobleaching of the YFP fluorophore. B, time course of changes in CFP and YFP fluorescence intensity. C, scatter plot of CFP intensity increase versus YFP intensity decrease. This is extrapolated to 100% on the x-axis for the calculation of FRET efficiency (eq. 1). D and E, FRET efficiencies measured for transfections with forced stoichiometries. D, increased β2 cDNA concentration during transfection with the α4XFP results in a decrease in percentage FRET efficiency. E, increased β2XFP cDNA concentration during transfection with α4 results in an increase in percentage FRET efficiency.

FRET by acceptor photobleach was studied while monitoring fluorescence from both the YFP and CFP fluorophores. Changes in fluorescence intensity versus time data were plotted (FIG. 4A and B), and FRET efficiency was calculated as described in Example 6 (FIG. 4C).

Measured FRET efficiencies ranged from 5 to 18 percent for various transfections with forced stoichiometries. As expected, a monotonic increase in FRET was observed when the fluorophores were attached to the α4 subunit and the mole fraction of α4 cDNA was increased, shifting the stoichiometry toward $(\alpha 4)_3(\beta 2)_2$ (FIG. 4D). Similarly, higher FRET efficiencies were observed when the fluorophores are attached to the β2 subunit and the stoichiometry was shifted toward $(\alpha 4)_2(\beta 2)_3$ population.

These measurements were correlated with the calculated values, assuming 52 Å as the shortest distance a between two fluorophores, using the linear relation summarized in FIG. 3D. Results showed that when the N2a cells are transfected with 4:1 cDNA ratio of α4:β2, ~90% of the assembled receptors have the $(\alpha 4)_3(\beta 2)_2$ stoichiometry. Increasing the mole fraction of the β2 cDNA in the transfection mixture increased the $(\alpha 4)_2(\beta 2)_3$ form, as expected. Interestingly, transfection with 1:1 cDNA ratio resulted in 60-70% $(\alpha 4)_3(\beta 2)_2$; similar results were previously reported using biochemical assays (Nelson et al., 2003).

Importantly, these results are also confirmed by an independent series of measurements that use FIR (see Example 10). The results illustrated in FIG. 5 confirmed that qualitatively and, to some extent quantitatively, higher FRET is observed when there are three rather than two fluorophore-labelled subunits of a single subtype in $(\alpha 4)_3(\beta 2)_{5-n}$ receptor.

Example 12

Figure 6:
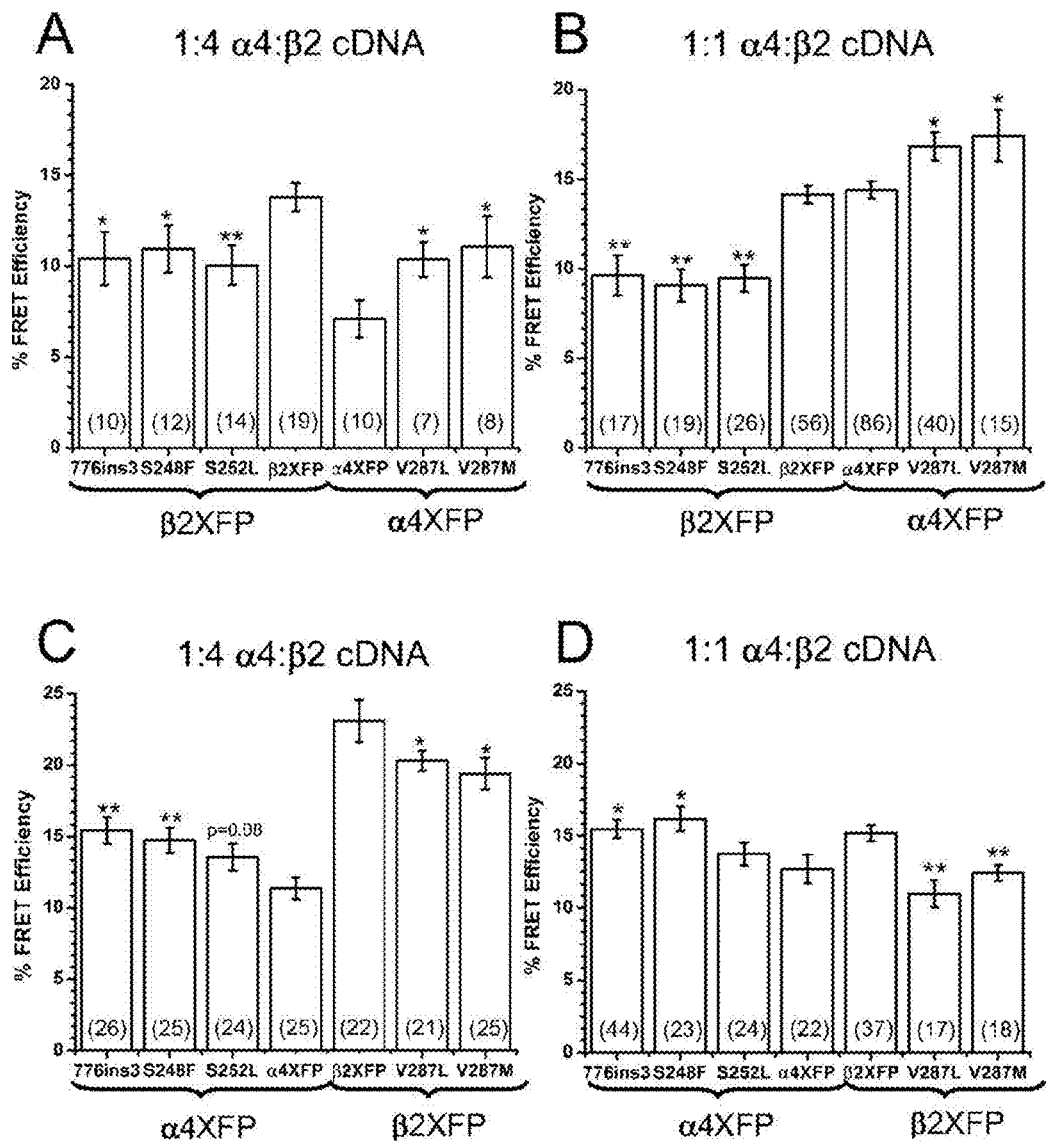
FIG. 6 shows: Autosomal dominant frontal lobe epilepsy (ADNFLE) mutations bias the α4β2 receptor population toward the $(α4)_3(β2)_2$ stoichiometry. A and B show FRET efficiency values measured by the DRAP method for five nonfluorescent ADNFLE mutant subunits transfected into N2a cells with the fluorescent WT complementary subunits (α4XFP or β2XFP, where XFP denotes a 1:1 mixture of the CFP and YFP subunits). A, 1:4 cDNA ratio of α4 to β2 subunits was transfected. B, 1:1 cDNA ratio of α4 to β2 subunits was transfected. C and D show FRET efficiency values measured by the DRAP method for five fluorescent ADNFLE mutant subunits (α4XFP or β2XFP, where XFP denotes a 1:1 mixture of the CFP and YFP ADNFLE subunits), transfected into N2a cells with the nonfluorescent WT complementary subunits. C, 1:4 cDNA ratio of α4 to β2 subunits was transfected. D, 1:1 cDNA ratio of α4 to β2 subunits was transfected. Data show mean±S.E.M. (# of cells given in each bar). Significance was tested with unpaired two-tailed t test; *, p≤0.05; **, p≤0.01.

ADNFLE Mutations Bias Stoichiometry Toward $(\alpha 4)_3(\beta 2)_2$: Acceptor Photobleach FRET Assays In one set of experiments, acceptor photobleach FRET efficiency values were analyzed from N2a cells transfected with non-fluorescent ADNFLE mutants plus fluorescently tagged complementary wild-type subunits (Son et al 2009) (FIG. 6A, B). There were two subsets of these experiments. One used α4 ADNFLE subunits plus fluorescent β2 subunits (denoted β2XFP in FIG. 6A, B); the other used β2 ADNFLE subunits plus fluorescent α4 subunits (denoted α4XFP in FIG. 6A, B). 1:4 (FIG. 6A) and 1:1 cDNA (FIG. 6B) transfection ratios for were carried out for the two nAChR subunits α4 and β2, respectively. (the 1:4 ratio was chosen because, as shown below, the ADNFLE mutations seem to favor nAChRs containing more α4 than β2 subunits; and it was important to know whether merely changing the cDNA ratios could reverse this effect).

In nearly all cases, FRET values differed significantly from the values for the corresponding fluorescently labeled wild type subunits. The α4 mutants tested (776ins3, S248F and S252L) showed significantly lower FRET efficiencies compared to the α4β2XFP control. This decrease in FRET efficiency suggested an increased $(\alpha 4)_3(\beta 2)_2$ receptor population versus the WT subunits. On the other hand the two β2 subunit ADNFLE mutants showed a significant increase in FRET efficiency compared to the α4XFPβ2 control. These results also suggest an increased $(\alpha 4)_3(\beta 2)_2$ receptor population versus the control cells. All five of the 1:4 cDNA transfection pairs (FIG. 6A), and all five of the 1:1 cDNA transfection pairs FIG. 6B, displayed a significant shift in subunit stoichiometry toward the $(\alpha 4)_3(\beta 2)_2$ configuration.

In a second set of experiments, FRET efficiency values from N2a cells transfected with subunits that contained both ADNFLE mutations and XFP labels were analyzed (FIG. 6C, D). The complementary subunits were WT. These experiments were performed with the five M2 domain ADNFLE mutations studied in the experiments described above. Again, there were two subsets of these experiments. One used α4 ADNFLE fluorescent subunits (denoted α4XFP in FIG. 6C, D) plus non-fluorescent β2 subunits; the other used β2 ADNFLE fluorescent subunits (denoted β2XFP in FIG. 6C, D) plus non-fluorescent α4 subunits. 1:4 cDNA (FIG. 6C) and 1:1 cDNA (FIG. 6D) transfection ratios were carried out for the α4 and β2 subunits, respectively. In four of five cases for both transfection ratios, the change in the FRET efficiency indicated a shift towards the $(\alpha 4)_3(\beta 2)_2$ receptor population.

This set of DRAP FRET experiments shows that, under 18 of 20 conditions, the ADNFLE mutations significantly ($p<0.05$) shift the stoichiometry of α4β2 receptor population toward the $(\alpha 4)_3(\beta 2)_2$ stoichiometry. This major result is consistent across several experimental conditions. The ADNFLE mutation is in either the α4 or the β2 subunit; the fluorescent groups are in either the mutant or non-mutant subunit; the fluorescent control groups are in either the α4 or the β2 subunits; the subunit cDNAs are transfected at roughly equal levels or with excess β2 cDNA. Thus, effects on expression or assembly caused by subunit carrying the mutation, by the type of fluorescent moiety (YFP vs CFP), or by its presence in a particular subunit can be ruled out.

Example 13

Nicotine Counteracts the Bias Toward $(\alpha 4)_3(\beta 2)_2$ of ADNFLE Receptors: Acceptor Photobleach FRET Assays Effects of chronic nicotine on nAChR subunit stoichiometry have been previously studied by several groups (Nelson et al., 2003; Moroni et al., 2006). These studies showed that exposure to nicotine preferentially upregulates a high-sensitivity receptor population. For WT receptors, this population is usually assigned to the $(\alpha 4)_2(\beta 2)_3$ stoichiometry.

The Applicants investigated the possibility that incubation with nicotine could shift ADNFLE receptors toward the $(\alpha 4)_2(\beta 2)_3$ stoichiometry, despite the bias toward the opposite stoichiometry.

A series of experiments were carried out with WT nAChR and ADFLE mutated nAChR were performed using image acquisition by FRET acceptor photobleach to detect nAChR stoichiometry before and after contact with nicotine.

Figure 7:
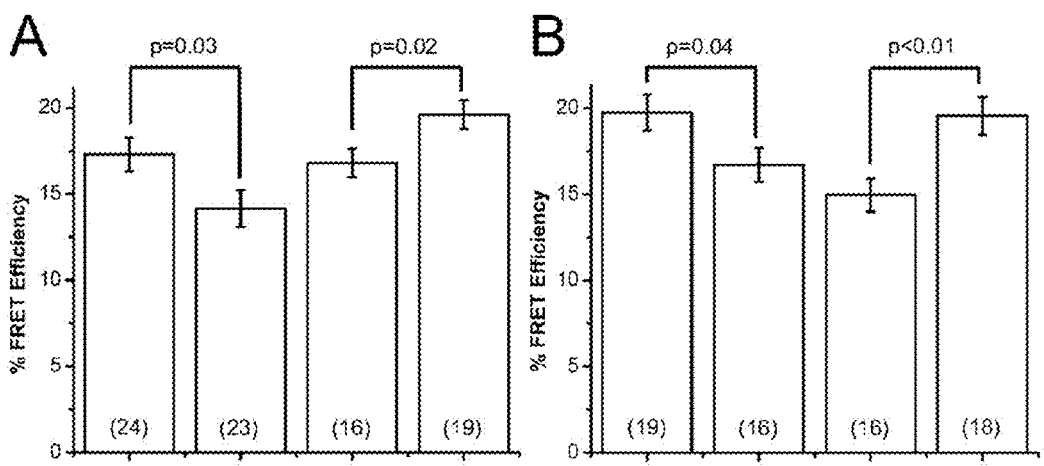
FIG. 7 shows: Incubation in nicotine shifts both the WT receptor (A) and an ADNFLE receptor (B) toward the $(\alpha 4)_2(\beta 2)_3$ stoichiometry. FRET efficiency values were measured by the DRAP method. A, FRET efficiency measured for N2a cells transfected with 1:1 cDNA ratio of $\alpha 4$XFP:$\beta 2$ or $\alpha 4\beta 2$XFP in the presence or absence of nicotine. B, FRET efficiency calculations for the N2a cells transfected with 1:1 cDNA ratio of $\alpha 4$:$\beta 2$ (V287L)XFP or $\alpha 4$XFP:$\beta 2$(V287L) in the presence or absence of nicotine. Data show mean±S.E.M. (number of cells given in each bar).

The results of the experiments performed with WT fluorescent receptors are illustrated in FIG. 7A. Incubation in nicotine produced a significant decrease or increase in FRET efficiency when the XFP probes were in the α4 or β2 subunits, respectively. This indicates that, as expected, incubation in nicotine shifts the receptor population toward the $(\alpha 4)_2(\beta 2)_3$ stoichiometry.

The results of analogous experiments performed with an ADFLE mutation, β2 V287L are illustrated in FIG. 7B. In cells transfected with α4 and β2 V287L XFP subunits, FRET efficiency was significantly higher after incubation in nicotine compared to control cells that were not exposed to nicotine. Likewise, cells transfected with α4XFP β2 V287L and treated with nicotine showed lower FRET efficiency than unexposed cells. This result suggests a shift in stoichiometry towards $(\alpha 4)_2(\beta 2)_3$ in the presence of nicotine, partially or completely counteracting the shift produced by the ADNFLE mutant alone toward the $(\alpha 4)_3(\beta 2)_2$ population.

The observed change in FRET efficiency in presence of nicotine from cells transfected with α4XFP and β2 V287L subunit was sufficient to bring the average values back to wild type levels; this indicates that cells carrying an ADNFLE mutation in the presence of nicotine had similar subunit stoichiometry to the wild type controls. The nicotine-induced shift was greater when the β2 V287L subunits were tagged with fluorescent proteins. In these cases the effect of nicotine was dominant and the average FRET efficiencies obtained from cells transfected with α4β2XFP and α4β2(V287L)XFP in the presence of nicotine did not differ significantly.

Example 14

ADNFLE Mutations Bias Toward $(\alpha 4)_3(\beta 2)_2$ and Nicotine Counteract the Bias: Sensitized Emission FRET Assays The acceptor photobleach FRET gives a report of the average FRET signal from confocal images of whole N2a cells expressing receptors assembled from fluorescently tagged subunits. Although acceptor photobleaching is suitable for FRET measurement at subcellular resolution in live cells, acceptor photobleaching is not optimal for such measurement. In Attempting acceptor photobleach FRET in subcellularly differentiated ROIs would likely introduce error in the temporal resolution because imaging would be far slower than the dynamics of transporter trafficking.

The ADNFLE mutations β2 V287L and α4 S248F, and the effects of long-term nicotine exposure, were therefore analyzed using pixel-resolved sensitized emission FRET measurements. Sensitized emission measurements have the advantages of 1) speed, requiring only a few seconds, 2) greater resolution, allowing pixel-by-pixel measurements, and 3) nondestructive readout, allowing for repeated measurement on a given cell. However, sensitized emission measurements require greater attention to corrections for spectral unmixing and bleedthrough.

Figure 8:
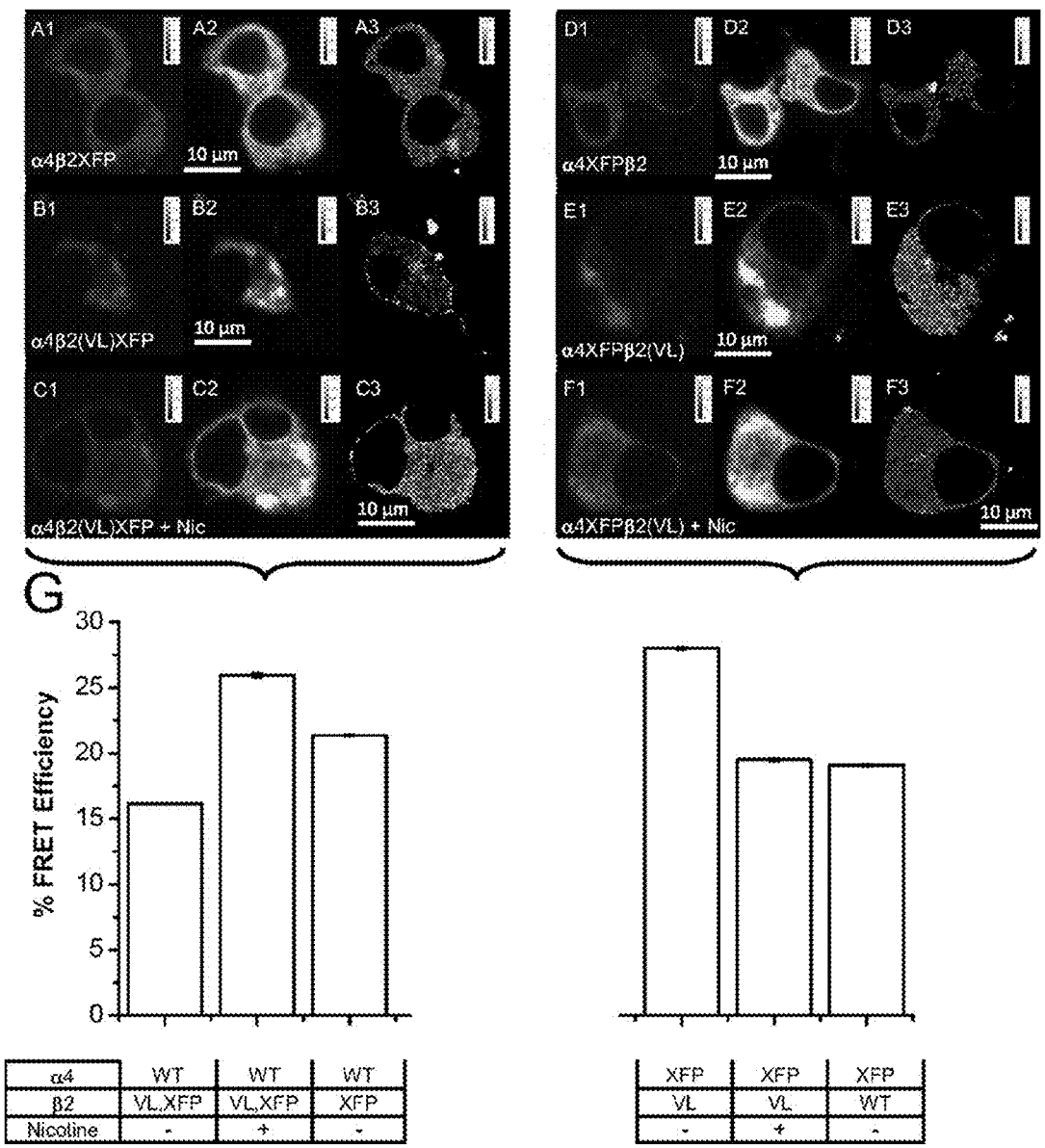
FIG. 8 shows: Representative pixel-resolved sensitized emission FRET images for various conditions. Column 1 displays unmixed cell images in the CFP channel after 439 nm excitation; column 2 displays unmixed cell images in the YFP channel after 514-nm excitation; column 3 displays the percentage FRET efficiency images. Nicotine was present at 1 μM for 48 h where indicated. Row A, WT $\alpha 4$ subunit plus $\beta 2$XFP. Rows B and C, WT $\alpha 4$ subunit plus $\beta 2$(V287L)XFP. B, control incubation. C, incubation in nicotine. Row D, $\alpha 4$XFP plus WT $\beta 2$. Rows E and F, $\alpha 4$XFP subunit plus $\beta 2$V287L. E, control incubation. F, incubation in nicotine. G, average FRET efficiencies. Each column gives average overall pixels for 20 to 25 cells in each case. The S.E.M. is smaller than the width of the line in all cases. Data show mean±S.E.M. (number of cells given in each bar). The S.E.M. (approximately the size of the lines delimiting the boxes) are smaller than in acceptor photobleach experiments, because S.E.M. is calculated on the basis of pixel numbers.
Figure 9:
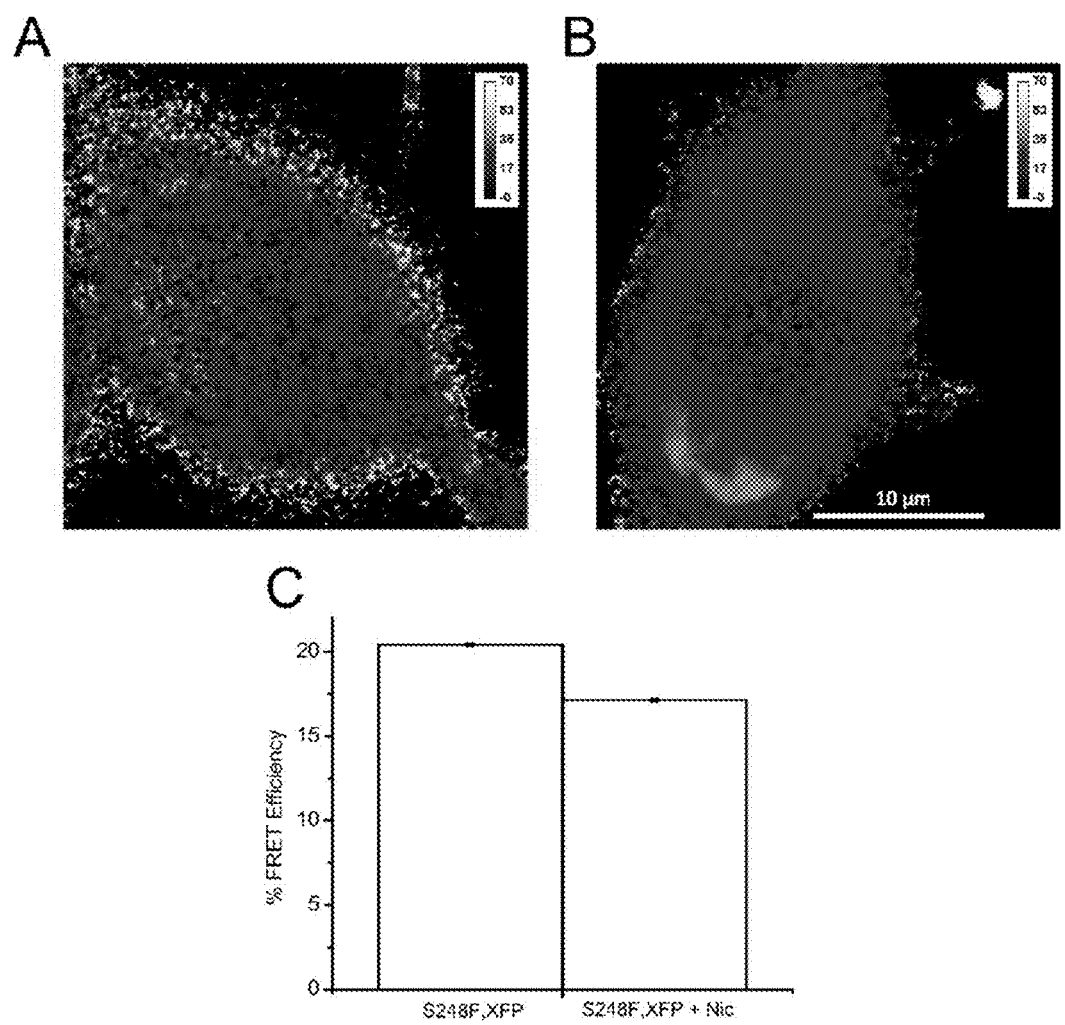
FIG. 9 shows: Nicotine shifts the population of $\alpha 4$ S248F ADNFLE receptors toward the $(\alpha 4)_2(\beta 2)_3$ stoichiometry. Representative pixel-resolved sensitized emission percentage FRET images. A, saline for 48 h. B, nicotine, 1 μM, 48 h. C, the graph shows data for a total of ~$5\times10^6$ pixels from 37 and 40 cells, respectively. Data show mean±S.E.M. The S.E.M. is approximately the size of the lines delimiting the boxes.

Results obtained with the sensitized emission method illustrated in FIG. 8 and FIG. 9 confirmed the acceptor photobleach results under the same conditions.

In particular, cells transfected with fluorescently tagged β2 V287L ADNFLE mutant subunits showed a significant 1.3-fold decrease in the mean FRET efficiency versus fluorescent non-ADNFLE subunits (FIG. 8, A, B, and G). On the other hand, a significant 1.4-fold higher mean FRET efficiency was detected from cells transfected with α4XFP and β2V287L compared with the control cells transfected with WT subunits (FIG. 8, D, E, and G). Both of these results imply a shift toward the $(\alpha 4)_3(\beta 2)_2$ stoichiometry.

Upon incubation of these cells with 1 μM nicotine for 48 h, the mean β2 intersubunit FRET efficiency increased to a level even higher than the control cells transfected with nonmutant fluorescent subunits (FIG. 8, C and G). Exposure to 1 μM nicotine for 48 h resulted in a decrease in the observed α4 intersubunit FRET efficiency, in this case completely back to WT levels (FIG. 8, F and G). Both of these results showed that incubation in nicotine produces at least a reverse in the shifted stoichiometry that results from the ADNFLE mutation.

The ability of nicotine to shift the stoichiometry toward $(\alpha 4)_2(\beta 2)_3$ for the α4 S248F mutation was also investigated. Experiments were performed with α4 subunits carrying both the S248F mutation and XFP moieties. The results illustrated in FIG. 9 show that incubation in nicotine (1 μM, 48 h) shifted the population toward the $(\alpha 4)_2(\beta 2)_3$ stoichiometry. Thus for the two ADNFLE mutations tested (one in the α4 subunit, one in the β2 subunit), nicotine seems to partially or completely counteract the mutation-induced bias toward the $(\alpha 4)_3(\beta 2)_2$ stoichiometry.

Example 15

Confirmation by FIR Analysis of FRET Determination for ADNFLE Mutations Bias Toward $(\alpha 4)_3(\beta 2)$ and Ability of Nicotine to Counteract the Bias The stoichiometry determination performed using the FRET acceptor photobleaching image acquisition and the FRET sensitized emission in ADNFLE mutations of nAChR was confirmed through fluorescence intensity ratio (FIR) analysis.

In particular, a fluorescence intensity ratio (FIR) analysis (Zheng and Zagotta, 2004; Staruschenko et al., 2005) was performed to determine the stoichiometry of α4β2 nAChRs using the same transfection conditions studied in the previous sections (see in particular Examples 10 and 11 and FIG. 5). Summarizing the FIR procedure, two parallel experiments were carried out under identical conditions: α4CFP-β2YFP and α4YFP-β2CFP. The related fluorescence data allow to eliminate the differences in the efficiency of the optical systems for the two fluorophores used in these experiments. Thus, measurements of the actual ratio between α4 and β2 subunits were acquired.

Figure 5:
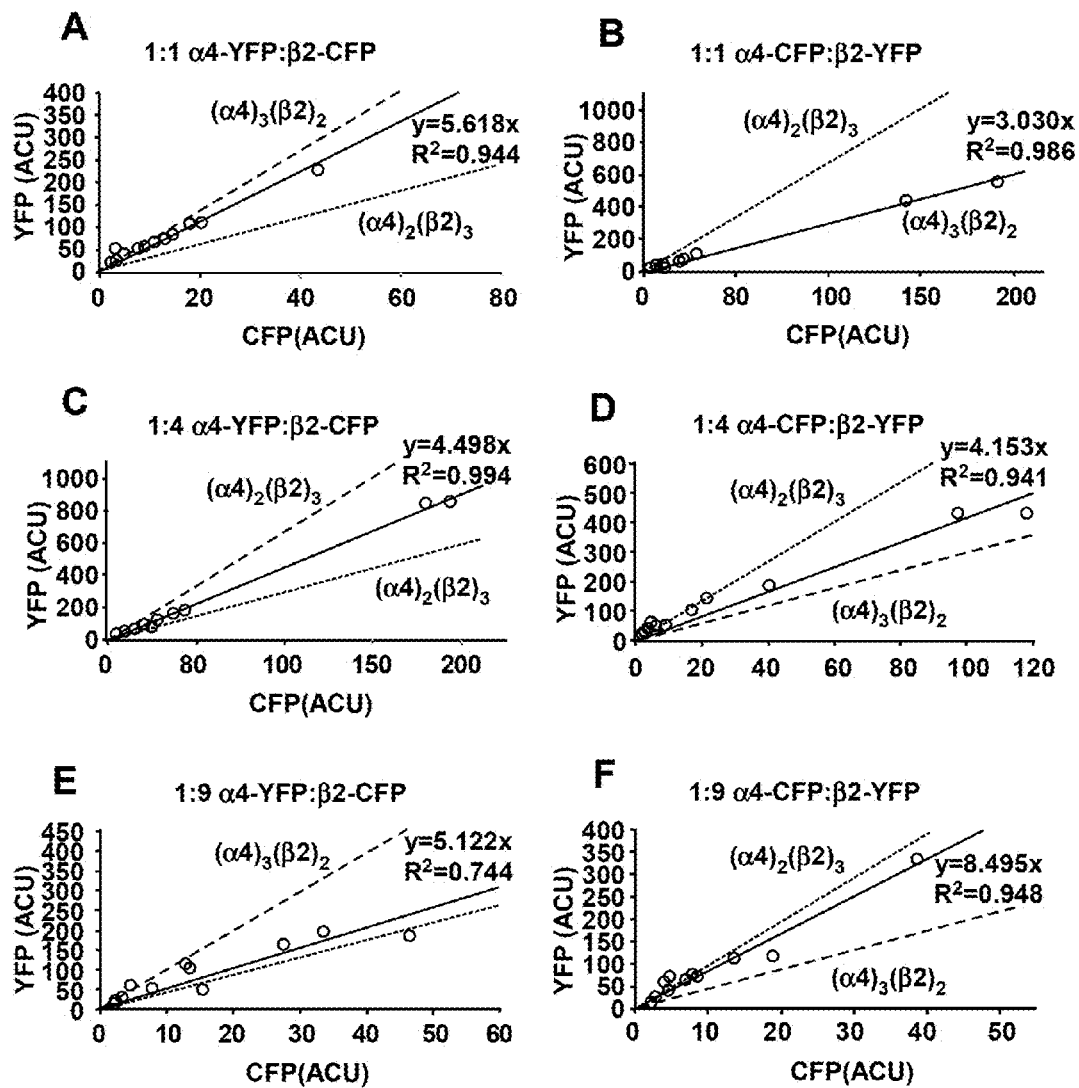
FIG. 5 shows: Fluorescence intensity ratio (FIR) measurements of the subunit ratio for α4β2 nAChRs. Scatter plot of the CFP intensity versus the YFP intensity (arbitrary calibrated units, (ACU)), measured from channels formed by α4YFP and β2CFP subunits (A, C and E), or α4CFP β2YFP (B, D and F). Each point is from an individual N2a cell. The dotted lines represent predicted fluorescence intensity ratio for 100% $(α4)_2(β2)_3$ stoichiometry and the dashed lines represent 100% $(α4)_3(β2)_2$ stoichiometry; the black lines are linear fits to each data set.
A, B, 1:1 ratio of α4:β2 cDNA.
C, D, 1:4 ratio of α4:β2 cDNA.
E, F, 1:9 ratio of α4:β2 cDNA.

The results of the determination of subunit stoichiometry performed with fluorescence intensity ratios is summarized in Table 2 below (see also FIG. 5).

TABLE 2

Percent of $(\alpha 4)_3(\beta 2)_2$ for WT nAChRs observed under various conditions in this study and a previous study.

| cDNAs | α4:β2 | | | | | |
|---|---|---|---|---|---|---|
| Ratios | 4:1 | 1:1 | 1:4 | 1:9 | 1:1 | |
| Other | | | | | Nicotine | 30° C. |
| FIR | 100 | 83 | 45 | 13 | 73 | N.D. |
| FRET | 94 ± 7 | 75 ± 3.5 | 52 ± 3 | 28 ± 3 | 61 ± 6 | 55 ± 6 |
| Reported* | N.R. | 82 | 43 ± 4 | N.R. | 68 ± 5 | 67 ± 6 |

In the illustration of Table 2, FIR and FRET efficiency measurements were used to determine the subunit stoichiometry from cells transfected with various ratios of subunit cDNA and exposed to nicotine or low incubation temperatures. FRET measurements for WT subunits are derived from the experiment of FIG. 4C, D; FIR measurements from the experiment of FIG. 5. Data for incubation at 30° C. are not shown. Results are compared to reported values. N.R.=not reported, N.D.=not determined in the present experiments. *(Nelson et al., 2003).

The data confirmed that changing the ratio of α4 to β2 cDNA governs the ratio of expressed subunits in assembled receptors; and the measured subunit ratios agreed acceptably with the measurements from FRET. In other assays, an expected increase in the fraction of $(\alpha 4)_2(\beta 2)_3$ receptors produced by nicotine was also detected (see Table 2).

Example 16

Overall Summary of Stoichiometric Differences Produced by ADNFLE Mutations and by Nicotine The data on comparative stoichiometry from acceptor photobleach FRET, pixel-based FRET, and FIR measurements obtained from the experiments exemplified in the above examples and in the related figures can be summarized. In particular data gathered for the various subunit transfection ratios, various mutants, and various labeling strategies were analyzed by the relation in FIG. 3D or by Equations 13 and 14, as appropriate.

In each experiment, ADNFLE and WT receptors were compared. The percentage of $(\alpha 4)_3(\beta 2)_2$ receptors is 1.2 times as great for ADNFLE receptors as for WT receptors (at least 12 experiments); the ratio was >1 in all experiments.

The effects of nicotine can also be summarized; in each case, the experiment compared incubation vs. saline. The percentage of $(\alpha 4)_3(\beta 2)_2$ ADNFLE receptors is 0.8 as great after nicotine incubation as after saline incubation (at least five experiments; the ratio was <1 in all cases).

Example 17

Pixel-Based Sensitized FRET Measurements of Regions of Interest

In possible approaches according to the present disclosure, sensitized emission FRET methods calculate the FRET in a sample on a pixel-by-pixel basis, but the amplitude of the FRET signal is reported as the mean from all the pixels included in the region if interest (ROI) (Feige et al., 2005; Hachet-Haas et al., 2006).

According to a different approach of the present disclosure a spectrally resolved refinement of the pixel-by-pixel analysis methods can also be performed that includes the NFRET amplitude of each pixel as a datum in the analysis rather than averaging the signal amplitudes of all the pixels in an ROI.

To develop the technique, a mouse GAT1 (mGAT1) GABA transporter was studied which had been fluorescently tagged and functionally characterized to be identical to the wild type non-fluorescent mGAT1 (Imoukhuede et al., 2009; Moss et al., 2009) as illustrated in the exemplary procedure of Example 4. The basic oligomeric unit of mGAT1 is a dimer, and an atomic-scale structure is available for dimers of a homologous transporter (Yamashita et al., 2005). Features of this dimer render it unlikely that a trimer would form, so that the simplest likely high-order oligomer is a dimer of dimers.

In experiments expressing fluorescently tagged mGAT1 transporters, this technique revealed that (a) FRET varies among subcellular compartments as defined by each ROI; and (b) within every ROI, the total NFRET distribution can consists of multiple subcomponents, each with its own distinct mean NFRET amplitude. For each fluorescent mGAT1 construct design studied, we analyzed the number of NFRET components, their amplitudes, and the proportion of the total NFRET distribution represented by each component.

Example 20 presents assumptions and calculations analyzing the FRET properties of dimers and tetramers. The experimental results are consistent with the idea that the first and second Gaussian components of the all-pixel mGAT1 NFRET amplitude distributions described in the subsequent section represent the dimer and a high order oligomerization state (probably a square or rhomboid tetramer) respectively.

The results indicate that the third highest-amplitude NFRET component present only in the mGAT1 NFRET distributions of mGAT1 constructs with functioning PDZ-interacting domains highlights mGAT1 oligomers interacting with PDZ-domain containing protein complexes.

Example 18

FRET Determination of ROI Including Non-Interacting Membrane Proteins

The methods of the present disclosure were also performed with non interacting membrane proteins, mGAT1 and the $\alpha 4\beta 2$ nAChR.

In particular, two fluorescently tagged plasma membrane proteins, mGAT1 and the $\alpha 4\beta 2$ nAChR, that do not interact in N2a cells were expressed (Drenan et al., 2008). The mGAT1CFP8 construct was cotransfected with plasmids that assemble $\alpha 4$YFP/$\beta 2$ nAChRs (Nashmi et al., 2003; Khakh et al., 2005; Drenan et al., 2008; Son et al., 2009). Control transfections of mGAT1CFP8/$\alpha 4$/$\beta 2$ and mGAT1/$\alpha 4$YFP/$\beta 2$ plasmids (250 ng each plasmid) were also performed (a) to generate reference spectra and (b) to determine spectral bleedthrough as described previously.

Figure 10:
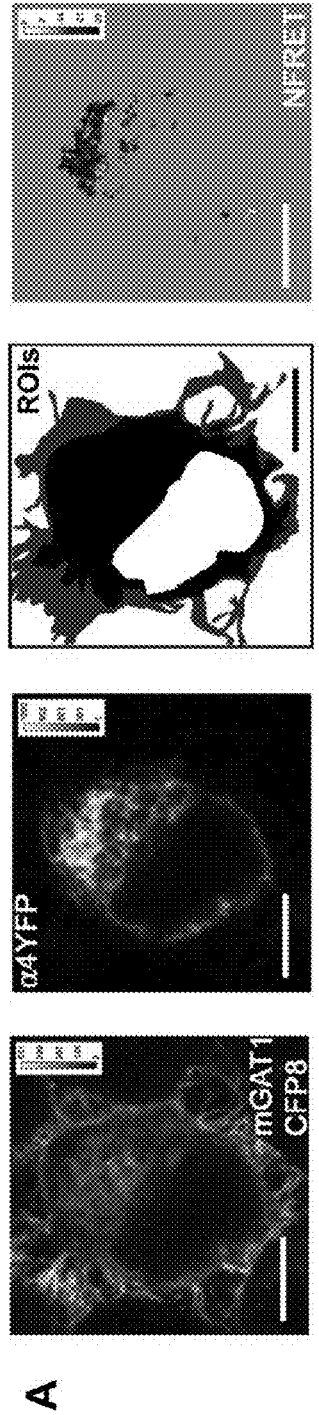
FIG. 10 shows Pixel-by-pixel quantification of sensitized emission FRET between mGAT1CFP8 and $\alpha 4$YFP$\beta 2$ nAChRs. A negative control experiment. (A; from left to right) mGAT1CFP8 fluorescence and $\alpha 4$YFP nAChR subunit fluorescence unmixed from an N2a cell coexpressing mGAT1CFP8, $\alpha 4$YFP nAChR subunit, and wild-type non-fluorescent $\beta 2$ nAChR subunit (calibration bars in arbitrary calibration units [ACUs]). ROIs were used to determine FRET. The dark gray-shaded area described the "peripheral" ROI, and the combined red and black areas correspond to the whole cell ROI. The fourth panel displays the NFRET image (calibration bar, NFRET×100). Pixels with signal amplitude below threshold are shaded gray. Bars, 10 μm. (B) Box plots displaying the range of NFRET detected from these negative control data. The box highlights the IQR (Q1-Q3), the center line in the box indicates the median, and the closed square symbol represents the mean. The whiskers' ends represent the boundaries of the lower and upper inner fences (1.5×IQR). The x marks the first and 99th percentiles. The half-shaded diamond symbols indicate the absolute maximum and minimum data point in each set. The plots from the whole cell and peripheral ROIs are colored black and dark gray, respectively, corresponding to the ROI color codes in A. The mean and median NFRET amplitudes for all pixels in each ROI are displayed in Table I. (C) Histograms displaying the distribution of pixel NFRET amplitudes for each condition (bin width, 0.02). Distributions for each ROI were fit to two Gaussian components. The individual components are shown as dashed lines, and the sum of the fit is shown as a solid line. The tables in each panel report the means of each component and the percentage of the pixels comprising each component.
Figure 10:
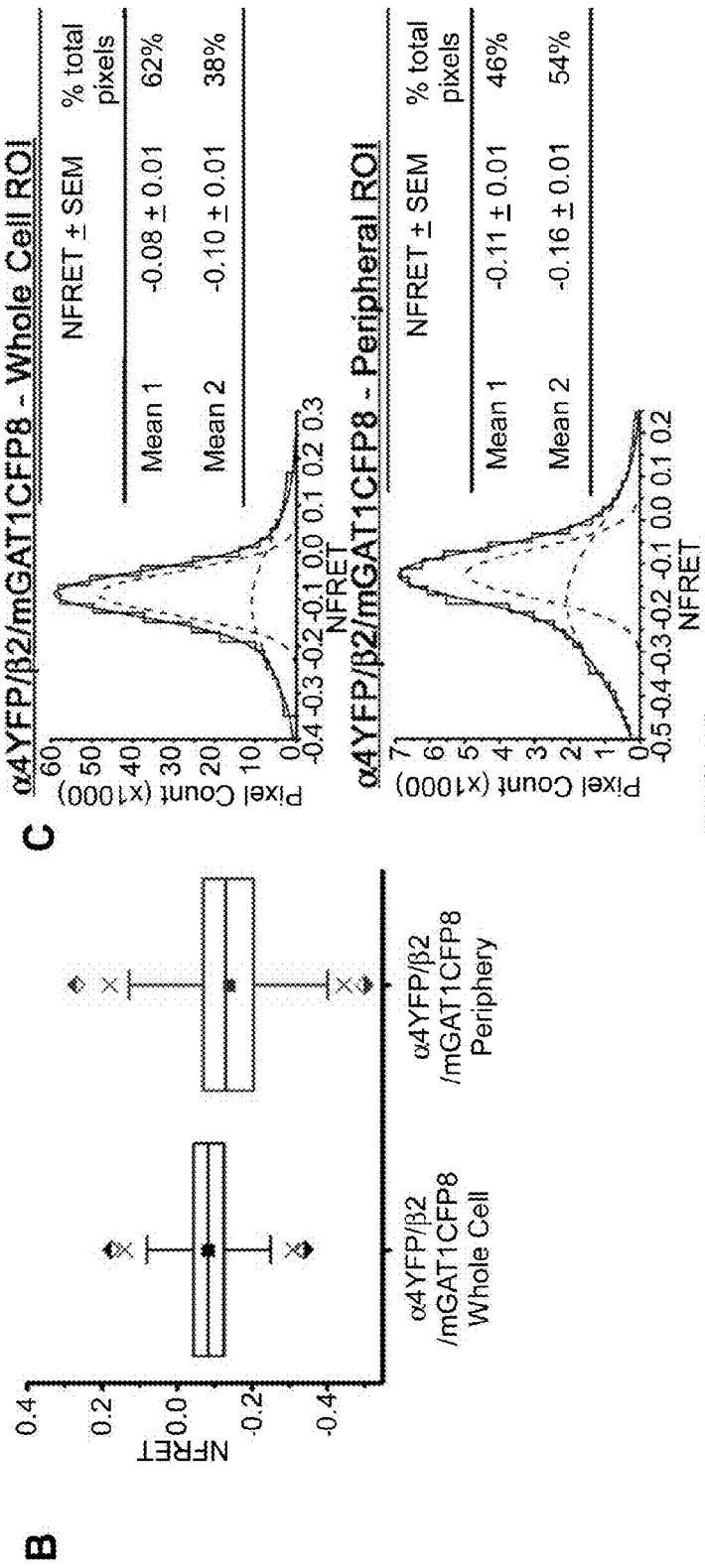
Figure 11:
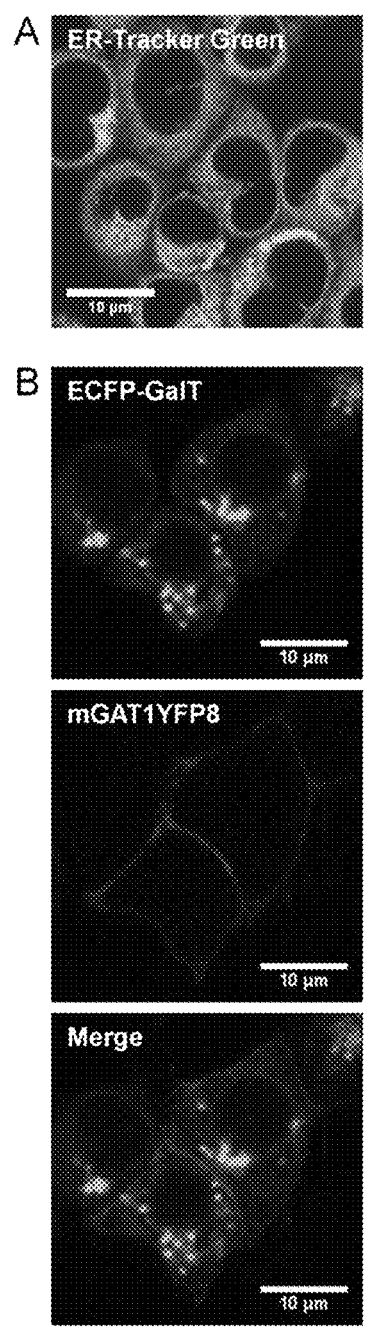
FIG. 11 shows: A) Endoplasmic reticulum labeled in live N2a cells with ER-Tracker Green (Invitrogen, Carlsbad, Calif.) according to the manufacturer's instructions. B) The trans-Golgi was labeled by ECFP-GalT in live N2a cells (top) and fluorescence is strongly localized in the perinuclear region of the cell. The same cells were co-transfected with mGAT1 YFP8 (middle) which primarily localized in the cell periphery. The merged image is shown in the bottom panel. Scale bars in all panels=10 μm.

The results are illustrated in FIG. 10. Both fluorescently tagged proteins maintained their normal expression pattern when coexpressed in N2a cells (FIG. 10A): the fluorescence pattern for fluorescent $\alpha 4$YFP$\beta 2$ nAChRs was uniform with little enhancement at the plasma membrane (FIG. 10A), as previously described in N2a cells (Drenan et al., 2008; Son et al., 2009), and the fluorescence pattern for mGAT1CFP8 was concentrated in the cell periphery with some fluorescence in the intracellular membranes near the nucleus.

A whole-cell ROI was defined that encompassed all the fluorescent pixels in the cell minus the nonfluorescent cell nucleus. The mean NFRET for all pixels within this ROI for cells coexpressing mGAT1CFP8 and $\alpha 4$YFP/$\beta 2$ nAChR was negative, indicating that no FRET occurred and that there was some overcorrection for donor and acceptor bleedthrough when there was no FRET (FIG. 10B).

Because the mGAT1CFP8 construct localized strongly in the cell periphery, this fluorescence was used to define a second ROI that contributed "peripheral NFRET". The peripheral ROI encompassed both the plasma membrane and a narrow annulus (~700 nm) of immediately adjacent cytoplasm. This description was used because constructs other fluorescent constructs such as mGAT1$_0$XFP which have known functional deficits exhibit concentrated fluorescence in the cell periphery due to pooling of transporter containing vesicles within ~500 nm of the outer lipid bilayer of the cell, rather than because of efficient insertion into the plasma membrane (Chiu et al., 2002; Imoukhuede et al., 2009; Moss et al., 2009). The calculated peripheral NFRET for coexpressed mGAT1CFP8 and $\alpha 4$YFP/$\beta 2$ nAChR was also negative (FIG. 10B).

FIG. 10C introduces frequency distributions of NFRET amplitudes from each pixel of several dozen cells. These data are binned to form all-pixel NFRET amplitude distributions: NFRET amplitude on the X-axis, number of pixels on the Y-axis. Although the NFRET distributions for both ROIs for these negative control transfections were best fit with two Gaussians, both components had negative mean NFRET amplitudes (FIG. 10C). These data confirm that the method detects no interaction between the $\alpha 4\beta 2$ nAChR and GAT1 in intracellular regions or in the cell periphery.

Example 19

Region-Specific FRET Quantification Reveals Different FRET Efficiency in Different ROI of Cells Expressing Fluorescent GAT1 Constructs To investigate FRET between fluorescent mGAT1 fusions, four ROIs were defined for each cell imaged. These were named the "whole-cell ROI", the "intracellular ROI", the "perinuclear ROI" and the "peripheral ROI".

The results illustrated in FIGS. 11 to 14, show that region-specific FRET quantification reveals high FRET efficiency in the periphery of cells expressing fluorescent GAT1 constructs that exhibit wild-type function. The whole-cell and peripheral ROIs were defined in the control experiments. Intracellular ROI is the space within the concentrated fluorescence at the cell periphery but subtracting the dark space occupied by the cell nucleus, and is densely filled by ER (FIG. 11A). The perinuclear ROI describes a concentrated region of fluorescence in cells expressing the fluorescent mGAT1 constructs adjacent to the cell nucleus; according to organelle markers, this ROI comprises mainly ER and Golgi (FIG. 11B). Fluorescence images of cells coexpressing the CFP and YFP variants of fluorescent GAT1 fusions were acquired and processed as described above.

Sensitized NFRET from cells expressing the wild-type like C-terminal fusion construct mGAT1XFP8 showed that 43.3% of the whole cell ROI NFRET signal came from the peripheral ROI (FIG. 12A). The mean NFRET amplitudes for all pixels in an ROI for N2a cells expressing mGAT1XFP8 were greatest in the peripheral ROI compared to the intracellular or the perinuclear ROIs (FIG. 12B). Specifically, the ratio of NFRET in the peripheral ROI was 1.7 fold greater than in the perinuclear ROIs. Also, the reported NFRET from pixels in the peripheral ROI of mGATXFP8 expressing cells had a much broader interquartile range than those from the perinuclear ROI (FIG. 12B). mGAT1 oligomerization was therefore detected in all ROIs, but an additional molecular event, specifically localized to periphery of cells expressing mGAT1XFP8 resulted in elevated FRET in this region. Analysis of the NFRET distributions from each ROI determined that the NFRET from the intracellular and perinuclear ROIs mGAT1XFP8 expressing cells was best fit with two Gaussians, both reporting positive mean NFRET. However, the whole cell ROIs and the peripheral ROIs were best fit with three Gaussians (FIG. 12D). The highest-amplitude NFRET component (1.8 fold greater mean NFRET than from the intermediate-amplitude component) represented 27% of the pixels in the peripheral ROI (FIG. 12C and FIG. 12D). Among the three subcellular ROIs, this highest-amplitude component appeared only in the peripheral ROI and was accompanied by a ~30% reduction in the peripheral ROI NFRET signal contributed by the lowest-amplitude component when compared to the intracellular or perinuclear ROIs (FIG. 12C and FIG. 12D). Thus for the wild-type like functioning mGAT1XFP* and mGAT1 XFP8, it can be inferred that two different oligomerization events were described by the low- and intermediate-amplitude components that were common to the NFRET distributions of all examined ROIs (see Appendix). In addition, elevated mean NFRET in the peripheral ROI versus intracellular regions corresponded to the third, high-amplitude component in the peripheral ROI NFRET distribution. In view of these results, it can be concluded that a specific mGAT1 oligomerization or interaction event—the molecular correlate for the third high-amplitude NFRET component—is highly localized to the cell periphery.

Sensitized NFRET from mGAT1XFP45, a construct which reports little function and no FRET by acceptor photobleach analysis (FIG. 13A), was analyzed with the pixel-by-pixel method (FIG. 13B). The pixel-by-pixel method did detect some mGAT1XFP45 oligomerization in small regions. These pixels were too few to influence the whole-cell averaging algorithms that calculated FRET by acceptor photobleaching. The perinuclear ROI contained most of these small regions highlighted by the sensitized NFRET approach in mGAT1XFP45 expressing specimens. The mean NFRET amplitude for all pixels in the perinuclear ROI resembled that recorded for mGAT1XFP8 (FIG. 13C). For mGAT1XFP45, the FRETing pixels in the peripheral ROI contributed only 6.4% of the whole cell ROI NFRET signal, nonetheless indicating that some oligomerized mGAT1XFP45 were exported from the perinuclear region and could eventually contribute to the small but significant [$^3$H]GABA uptake for this construct in the functional assays (Moss et al., 2009).

Figure 13E:
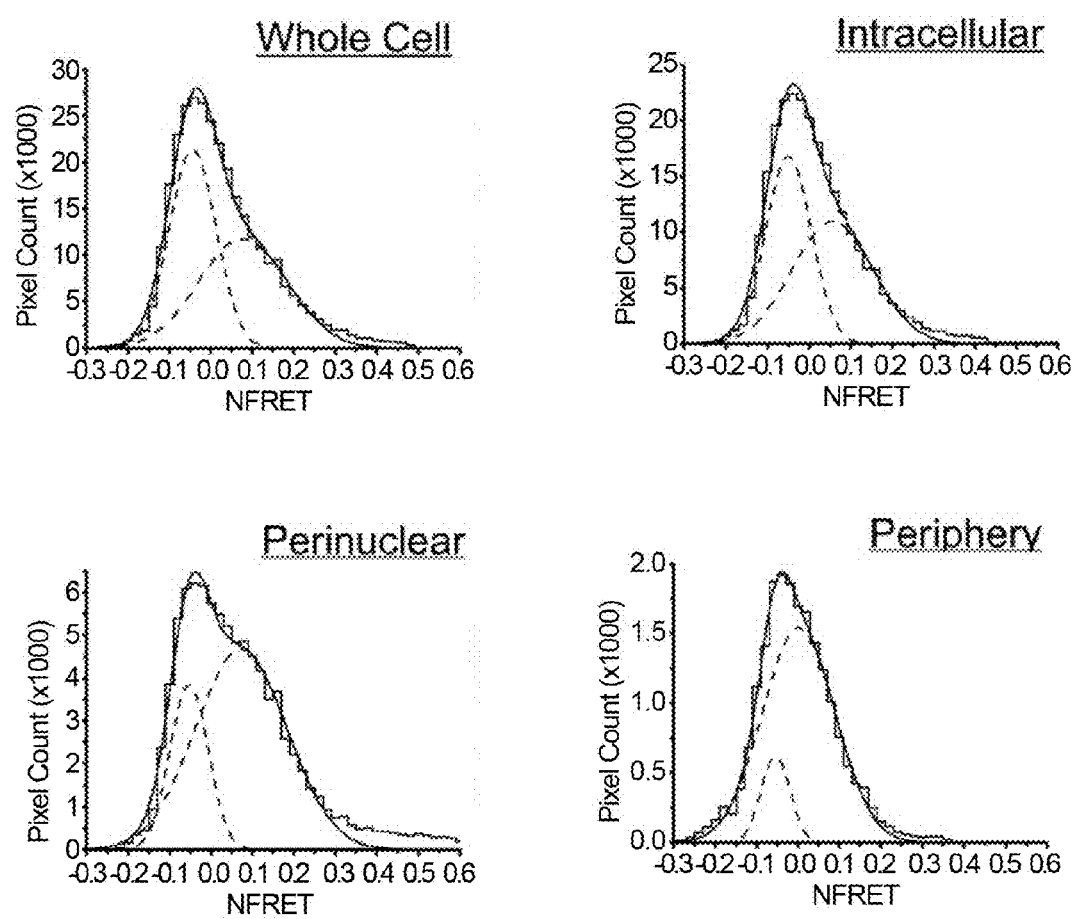
FIG. 13 shows: (A) Plot of acceptor photobleach and donor photorecovery for mGAT1CFP45/mGAT1YFP45 (n=12). (B) Pixel-by-pixel quantification of sensitized emission FRET between mGAT1XFP45: (from left to right) mGAT1CFP45 fluorescence and mGAT1YFP45 fluorescence (calibration bars, ACUs), ROIs used to determine NFRET (color coding as in FIG. 12), and the NFRET image (color calibration bar, NFRET×100) of the same cell. Pixels with amplitude below threshold are shaded gray. Bars, 10 μm. (C) Box plots displaying NFRET for all pixels in each ROI of cells expressing mGAT1XFP45. The box, whiskers, and other data points are represented as in FIG. 10B. Box plots for each ROI are colored according to the code in A (ROI), and the intracellular data are colored blue. (D) Table of results for mGAT1XFP45 transfections displaying the mean of each Gaussian component of the summed fit of the distributions in FIG. 13E and the percentage of the pixels that comprise each component. (E) Distributions of NFRET signal amplitude per pixel for each ROI (bin width, 0.02) from mGAT1XFP45-expressing cells. The individual components and their sum are shown as dashed and solid lines, respectively.

The NFRET distributions for all ROIs of mGATXFP45 expressing cells were best fit with two Gaussians, the first of which reported a negative mean NFRET (FIG. 13D and FIG. 13E). The positive population made up >75% of the NFRET signal in the peripheral and perinuclear ROIs. We observed that the mean NFRET of the positive Gaussian component was 1.4 fold larger in the peripheral ROI compared with the same component of the mGAT1XFP45 perinuclear ROI NFRET. Even though very few mGAT1XFP45 oligomers inserted into the plasma membrane, it appeared that those that did insert were subject to the same molecular event that caused increased FRET in the periphery of cells expressing wild-type functioning fluorescent mGAT1 constructs.

Figure 14D:
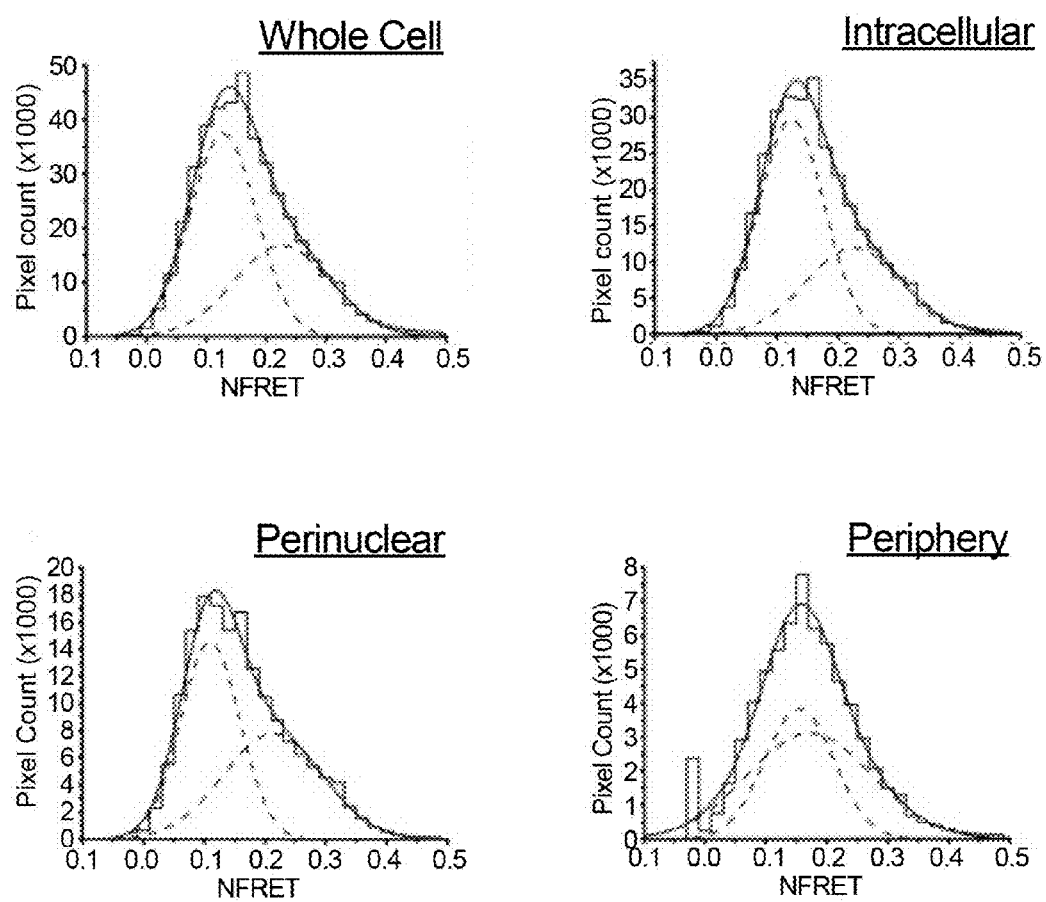
FIG. 14 shows Pixel-by-pixel quantification of sensitized emission FRET between mGAT1$^{565}$XFP$^{566}$CT and mGAT1$^{570}$XFP$^{571}$CT. (A; from left to right) mGAT1$^{565}$CFP$^{566}$CT fluorescence and mGAT1$^{565}$YFP$^{566}$CT fluorescence (calibration bars, ACUs), ROIs used to determine NFRET (color coding as in FIG. 12), and the NFRET image (color calibration bar, NFRET×100) of the same cell. Pixels with signal amplitude below threshold are shaded gray. Bars, 10 μm. (B) Box plots displaying NFRET for all pixels in each ROI of cells expressing mGAT1$^{565}$XFP$^{566}$CT. The box, whiskers, and other data points are represented as in FIG. 10 B. (C) Table of results for mGAT1$^{565}$XFP$^{566}$CT transfections displaying the mean of each Gaussian component of the summed fit of the distributions in D and the percentage of the pixels comprising each component. (D) Distributions of NFRET signal amplitude per pixel for each ROI (bin width, 0.02) from mGAT1$^{565}$XFP$^{566}$CT-expressing cells. The individual components and the sum of the fit are shown as dashed and solid lines, respectively. (E) Representative fluorescence images of mGAT1$^{570}$XFP$^{571}$CT-expressing N2a cells, the regions of interest, and corresponding NFRET image. Calibration and color coding are as for FIG. 12 A. (F) Box plots displaying NFRET for all pixels in each ROI of cells expressing mGAT1$^{570}$XFP$^{571}$CT. (G) Table of results for mGAT1$^{570}$XFP$^{571}$CT transfections displaying the mean of each Gaussian component of the summed fit of the distributions in H and the percentage of the pixels that comprise each component. (H) Distributions of NFRET signal amplitude per pixel for each ROI (bin width, 0.02) from mGAT1$^{570}$XFP$^{571}$CT-expressing cells. The individual components and their sum are shown as dashed and solid lines, respectively.

The mGAT1$^{565}$XFP$^{566}$CT construct, has poor function and the completely internal distribution of fluorescence in 27% of cells in which it is expressed (Moss et al., 2009). mGAT1$^{565}$XFP$^{566}$CT reported a robust mean NFRET amplitude for all pixels (≥0.17) in all ROIs examined (FIG. 14A and FIG. B) indicating that significant transporter oligomerization was occurring. However, the NFRET signal was mainly due to assembled intracellular mGAT1$^{565}$XFP$^{566}$CT rather than plasma membrane inserted transporters, even in the peripheral ROI. mGAT1$^{565}$XFP$^{566}$CT NFRET distributions were best fit with two Gaussians in all ROIs examined (FIG. 14C and FIG. 14D). In the peripheral and perinuclear ROIs, the two subpopulations contributed approximately equally to the total NFRET signal. In the intracellular ROI, the lower mean NFRET signal predominated.

The mean NFRET amplitude from mGAT1$^{570}$XFP$^{571}$CT expressing cells (FIG. 14E and FIG. 14F), was less than from those expressing mGAT1$^{565}$XFP$^{566}$CT. This probably arose in part from the increased fluorophore separation in this construct. The XFP moiety is fused five residues more distal from the end of the TM12 helix in the mGAT1$^{570}$XFP$^{571}$CT constructs. Exact intermolecular distances cannot be calculated from FRET efficiencies of proteins fused to GFP derivatives (Rizzo et al., 2006). However, side-by-side FRET efficiency calculations (using Eq. 4) suggested that in the perinuclear ROIs the apparent fluorophore separation in mGAT1$^{570}$XFP$^{571}$CT oligomers (E=7.9±1.9%) is on average 1.25 fold greater than in mGAT1$^{565}$XFP$^{566}$CT oligomers (E=25±3.5%). As for mGAT1$^{565}$XFP$^{566}$CT, the mean NFRET amplitude from all pixels in cells expressing mGAT1$^{570}$XFP$^{571}$CT was similar between the peripheral and perinuclear ROIs (ratio 1.0).

Analysis of the NFRET distributions for each ROI determined that all were best fit with two Gaussians (FIG. 14G and FIG. 14H). However, in the periphery the two components did not appear to describe the same populations reported by the components of the other ROIs. The mean amplitude of the major peripheral NFRET component (98% of the signal) lay~half-way between the amplitudes of the two NFRET components of the perinuclear, intracellular or whole cell ROIs. A possible conclusion is that two Gaussian components merged into one with an intermediate NFRET amplitude in the periphery because the populations mix at a level too fine to resolve in a 69 nm$^2$ pixel (see "FRET for tetramers and dimers—calculations and considerations", below). The second component of the mGAT1$^{570}$XFP$^{571}$CT peripheral NFRET signal had a mean amplitude (0.29±0.09) twice that observed for the second Gaussian component of the perinuclear ROI NFRET (FIG. 14G and FIG. 14H).

Figure 12:
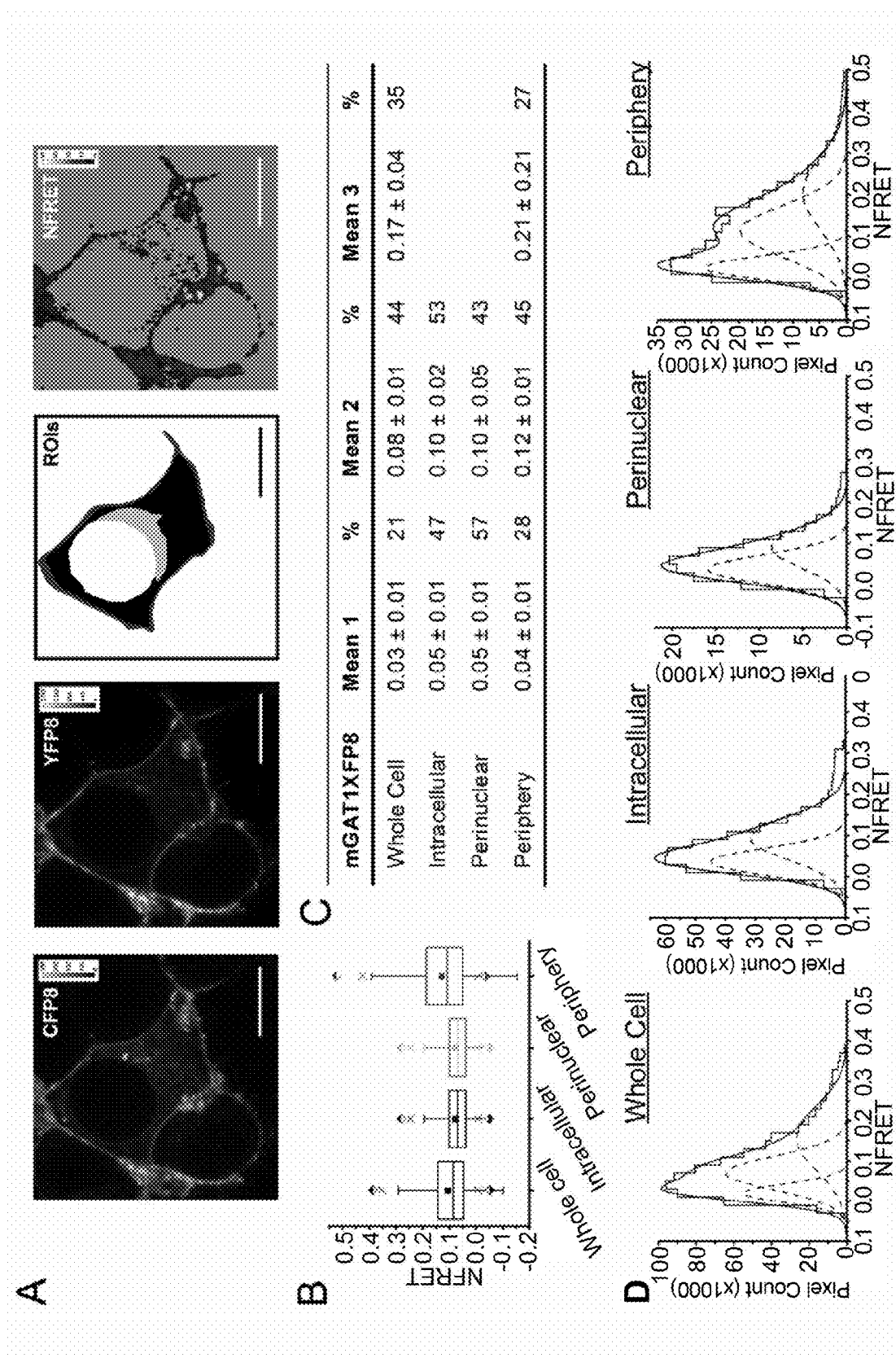
FIG. 12 shows: Pixel-by-pixel quantification of sensitized emission FRET for mGAT1XFP8. (A; left two panels) mGAT1CFP8 fluorescence and mGAT1YFP8 fluorescence (calibration bars, ACUs). In the third panel, ROIs were used to determine NFRET. The dark gray-shaded area described the "peripheral" ROI, the light gray-shaded area corresponds to the "perinuclear" ROI, the black and green region with the red area describes the "intracellular ROI," and the combined dark gray, light gray, and black areas correspond to the whole cell ROI. The fourth panel displays the NFRET image of the same cell (color calibration bar, NFRET×100). The color code in the NFRET image includes negative and positive signal amplitudes. Pixels with signal amplitude below threshold are shaded gray. Bars, 10 μm. (B) Box plots displaying NFRET for all pixels in each ROI of cells expressing mGAT1XFP8. The box, whiskers, and other data points are represented as in FIG. 10B. (C) Table of results for mGAT1XFP8 transfections displaying the mean of each Gaussian component of the summed fit of the distributions in D and the percentage of the pixels comprising each component. (D) Distributions of NFRET signal amplitude per pixel for each ROI (bin width, 0.02) from mGAT1XFP8-expressing cells. The individual components are shown as dashed lines, and the sum of the fit is shown as a solid line.

Although contributing only a small fraction (2.3%) of the total signal for the peripheral ROI, the ratio of mean NFRET amplitude of this component vs. the second component of the perinuclear or intracellular ROIs (2.1 and 1.7 respectively) resembled that of the highest amplitude component of mGAT1XFP8 NFRET (FIG. 12). The small but measurable high amplitude NFRET component in the mGAT1$^{570}$XFP$^{571}$CT peripheral NFRET signal presumably reflects its impaired plasma membrane insertion, as determined by GABA uptake assays, and is also consistent with the observation that mGAT1$^{570}$XFP$^{571}$CT functions better than mGAT1$^{565}$XFP$^{566}$CT (Moss et al., 2009).

Example 20

FRET Measurement for Tetramers and Dimmers: Calculations and Considerations

An assumption for the FRET based determination of GAT stoichiometry is that the fluorescent mGAT1 constructs with the most wild-type function most accurately report the normal oligomerization properties of mGAT1 via FRET. The lowest-order oligomer is a dimer.

Figure 18:
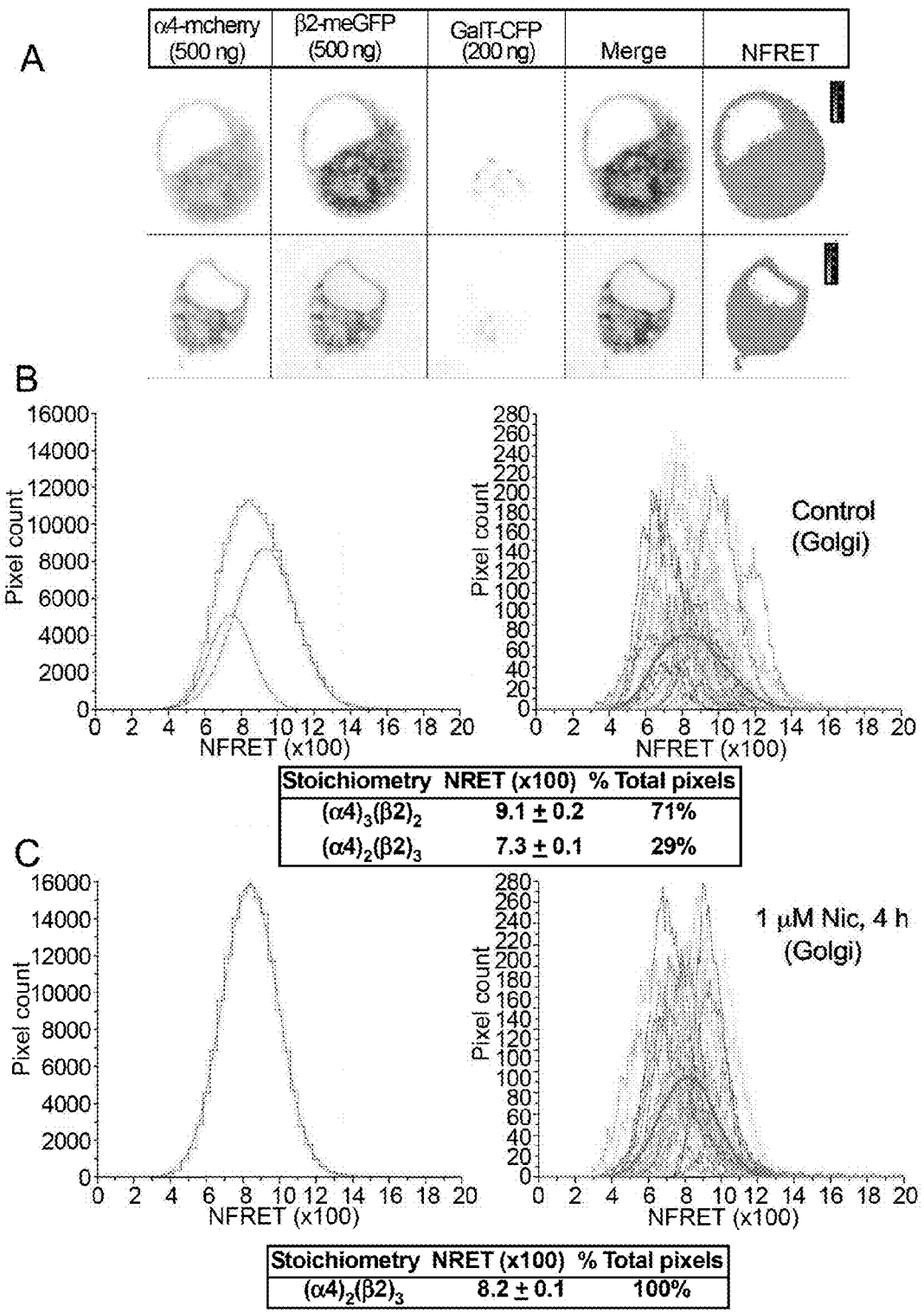
FIG. 18 shows: (A) Representative images of N2a cells transfected with α4-mCherry, β2-mEGFP and GalT-ECFP (Golgi reporter) are shown. NFRET images used for pixel-by-pixel FRET analysis for each cell are also depicted (far right panel). Scale bars, 10 μm. (B) Gaussian fits to the NFRET distribution from the Golgi bodies ROI (left) (n=52000 pixels from 40 cells; alternate stoichiometries correspond to the subcomponents of the summed fit) prior to incubation with nicotine and the individual NFRET distributions from the ROIs from each cells (right) are shown. (B) Gaussian fits of the NFRET distribution from Golgi bodies (n=61000 pixels from 40 cells) from the same dish following incubation with 1 μM nicotine for 4 h (left) and individual NFRET distributions from the Golgi ROI in each cell (right). An averaged distribution generated from the individual distributions for both data sets is superimposed (bold line).

Based on the assumption that CFP and YFP tagged fluorescent mGAT1 protomers are synthesized and fold equally efficiently, in a cell transfected by equimolar amounts of the donor and acceptor cDNAs, a binomial distribution of donor-donor, donor-acceptor, and acceptor-acceptor tagged dimers will exist (FIG. 18A).

Only 50% of the total oligomer population, the donor-acceptor dimers, will contribute to the NFRET amplitude. This means that the experimentally measured NFRET amplitude for a specific pixel is not the true "pair-wise" FRET data of a single CFP-YFP pair, but is the "apparent" FRET of a specific concentration of the FRET yielding dimers, mixed with non-FRET productive dimers, and in some organelles donor or acceptor monomers (Raicu, 2007). In oligomers larger than dimers, there is more than one pathway for non-radiative energy transfer (FIGS. 18B and C). The apparent FRET in each pixel is influenced by: (a) the number of donor-acceptor pair radii in the oligomers (e.g. two possible FRET radii exist in a square tetramer; r and r$\sqrt{2}$; (b) the stoichiometry of the donor and acceptor fluorophores within each oligomer; (c) The relative concentration of each oligomer stoichiometry type; and (d) The proportions of dimers versus higher order oligomers that exist in the pixel.

Figure 15A:
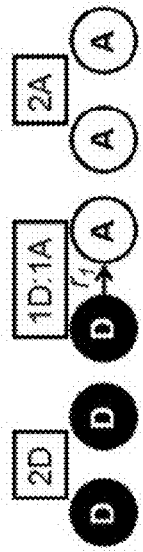
FIG. 15 shows a schematic illustration of theory of FRET from three oligomer types with several fluorophore stoichiometries. XFP tagged mGAT1 protomers can assemble in three possible fluorophore stoichiometries. Square tetramers can have six possible fluorophore configurations. There are nine possible configurations of a rhomboid tetramer. Nomenclature for panels A-C: D=Donor, A=acceptor, $E_{xD:yA}$=FRET efficiency for each configuration where x and y represent the number of donor or acceptor fluorophores respectively, $R_0$=the Förster distance for a CFP-YFP pair, $r_1$=the pairwise FRET radius in the basic mGAT1 dimer. $r_2$-$r_4$=the three other pairwise FRET radii present in either square tetramers or rhomboid tetramers. Plot of the apparent FRET ($E_{App}$) modeled for mGAT1 dimers, square tetramers or rhomboid tetramers with changing $r_1$, the pairwise FRET radius in the basic mGAT1 dimer.
Figure 15B:
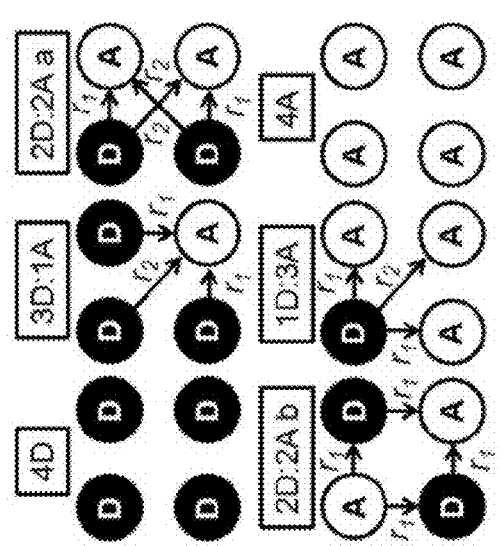
Figure 15D:
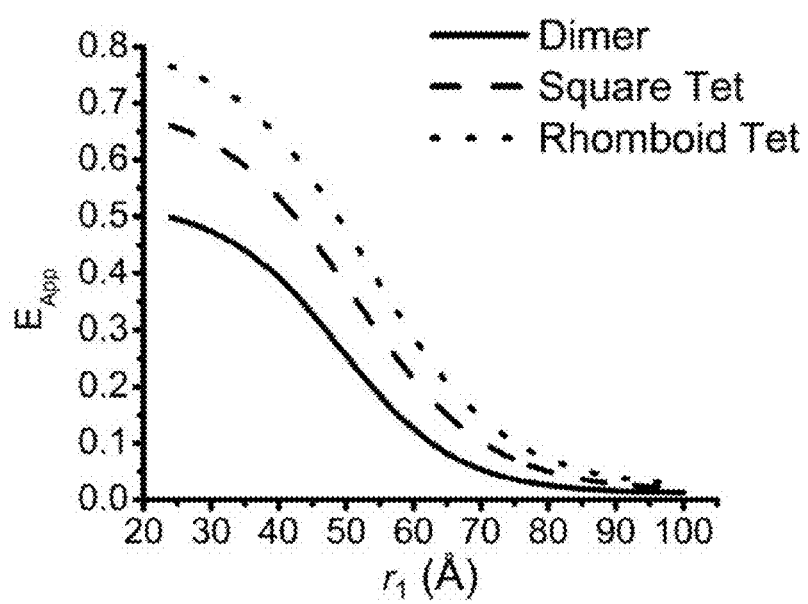

Two possible forms of such an mGAT1 tetramer were considered. The square tetramer would resemble the arrangement of subunits in voltage-gated potassium channels (Kerschensteiner et al., 2005; Miranda et al., 2008) (FIG. 15B). A rhomboid organization (FIG. 15C) was also considered because mGAT1 molecules function as monomers; therefore an mGAT1 oligomer might not display the approximate four-fold radial symmetry that constrains voltage-gated channels (Scholze et al., 2002; Yamashita et al., 2005; Zhang and Rudnick, 2006). FIG. 15D shows a model of the apparent FRET efficiencies that would arise from populations of mGAT1 dimers, square tetramers or rhomboid tetramers for various distances between fluorophores. To set the initial value for the closest distance between protomers r$_1$, we used the LeuT$_{Aa}$ structure (PDB entry 2A65A, (Yamashita et al., 2005)). We assumed that the fluorophores in the mGAT1 C-terminus hang directly below the substrate molecule in the protomer core. The proportional values for r$_{2-4}$ were determined when r$_1$ was varied (FIGS. 15A-C). The dimensions of the XFP barrel limit the smallest measurable distance for side-by side chromophores in an oligomerized membrane protein to r$_1$=24 Å (Ormo et al., 1996), and we assumed a largest value of r$_1$=100 Å. The FRET efficiency for each tetramer configuration for each r$_1$ was determined and multiplied by the probability of its occurrence to determine the apparent FRET, E$_{app}$ (Corry et al., 2005). A further assumption was that energy transfer always occurs in all possible FRET yielding configurations (i.e. fluorophore bleaching or blinking was not factored into the calculations), exactly equal representation of donor and acceptor tagged protomers in all compartments, and equally efficient assembly of dimers and high order oligomers.

The corresponding calculations show that, relative to E$_{app}$ from a dimer, a square tetramer and a rhomboid tetramer have 1.33-1.96 fold and 1.54-2.87 higher FRET, respectively, as r$_1$ varies. For the majority of the constructs examined in this disclosure, the mean NFRET amplitude of the second Gaussian fit component was between 1.6 and 2.6 fold greater than for the lowest amplitude first component.

The width of each component to the Gaussian fits to the mGAT1 NFRET distributions was further analyzed. Consider the simple example of a single pixel in which the only oligomer type possible is a dimer. The NFRET amplitude from that pixel is determined by the number of dimers which possess both a donor and acceptor-tagged protomer, but the signal from these oligomers is normalized to the square root of the product of the pixel's donor and acceptor fluorophore intensities. Donor-donor dimers, acceptor-acceptor dimers, and non-oligomerized monomers can also exist in the pixel. Furthermore immature, bleached, or misfolded XFP moieties may exist, all reducing the measured NFRET from donor-acceptor dimers (FIG. 15A). If all pixels in a ROI contain only dimers, then the fit to the NFRET amplitude distribution has a width determined by the variation in the number of FRET-yielding dimers relative to the total fluorophore concentration per pixel in the ROI. Some of these statistical considerations generate a binomial distribution; but given the additional effects, and the transformation from nF to NFRET, a Gaussian distribution is assumed.

Figure 14:
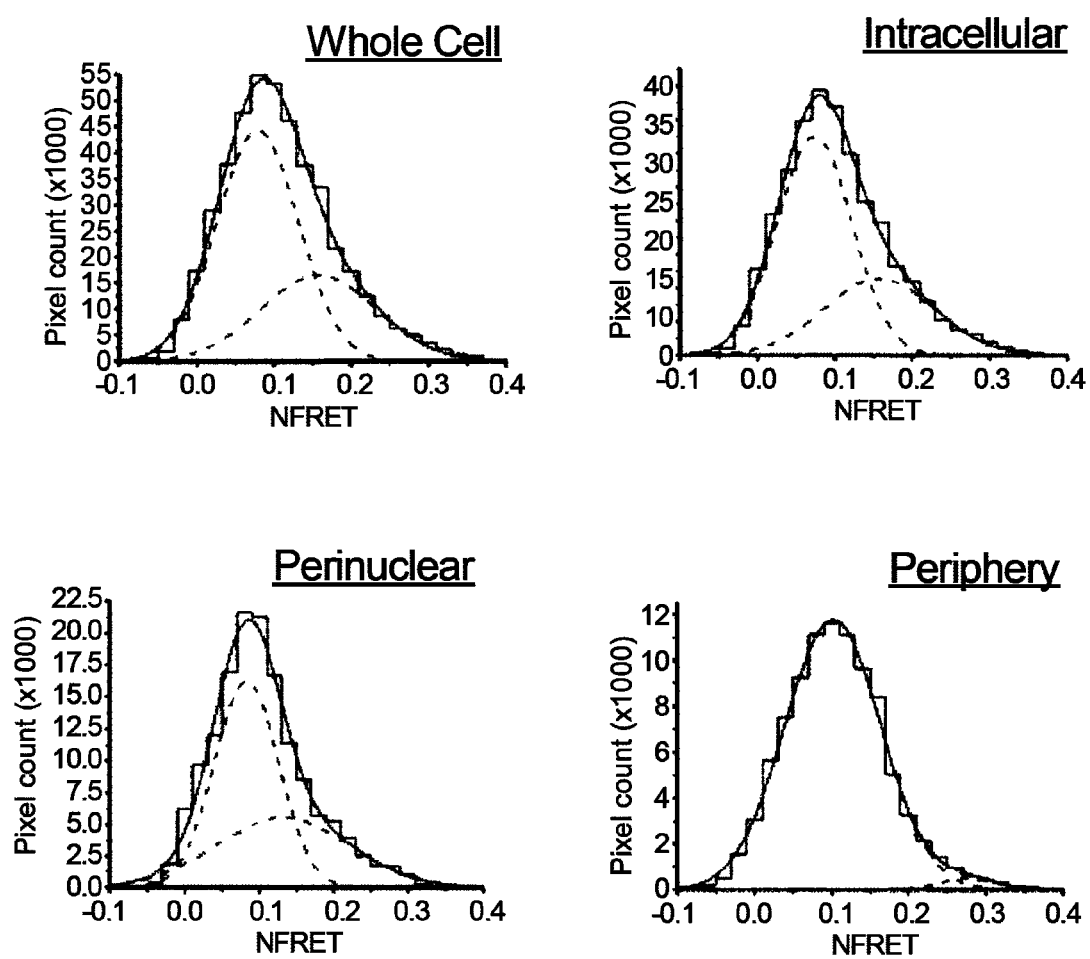

Now consider a pixel containing only mGAT1 tetramers. There are two major sources of variation in the NFRET amplitude: a) the proportion of the total fluorophore concentration in the pixel that assembles into FRET-yielding tetramers and b) the relative contributions of each FRET-yielding donor and acceptor fluorophore stoichiometry in the pixel (FIGS. 15B and C). Tetramers have more sources of variation than dimers. Therefore, for an ROI whose pixels contain only tetramers, and at levels of donor and acceptor fluorophores equal to that of a pure dimer population, the NFRET distribution is fit by a single Gaussian of average amplitude greater than that for the dimer case; however the full width at half-maximum (FWHM) exceeds that from the ROI containing only dimers. Throughout this work it was observed that the FWHM of the first low-amplitude NFRET component was less than for the second medium-amplitude component (FIGS. 12-14). Given the presence of negative NFRET amplitudes, a possible course of action is to not converting the FWHM values to coefficients of variation.

Pixels are 69 nm$^2$, but a pixel's optical signal also contains X, Y, and Z contributions from nearby regions, as appropriate to the microscope's point spread function, therefore increasing the possible variability from a single pixel's signal. The signal from some or most pixels also arises from a mixed population of oligomerization states. Therefore the NFRET amplitude is also determined by the numbers of the FRET-yielding dimers and tetramers and the fluorophore stoichiometries in the tetramers. For all the pixels from an ROI containing both dimers and tetramers, the NFRET distribution is fit with two overlapping Gaussian components, one for each oligomer population. The mean amplitudes of these two components represent pixels primarily but not purely containing one oligomerization state and as a result are shifted closer together than if the NFRET signal from the ROI came from pixels that contained either pure dimers or pure tetramers. Subcomponent overlap occurs because in pixels containing a heterogeneous population of dimers and tetramers there are numerous possibilities where different mixtures of oligomer types and fluorophore stoichiometries result in the same pixel NFRET amplitude.

Example 21

Nicotinic Receptors Also Display a Two-Component NFRET Distribution

Data presented in the examples above indicate that mGAT1, a membrane protein, displays only a two-component NFRET distribution if its oligomers are not inserted into the plasma membrane at normal wild-type levels. The applicability of this proposition for the heteropentameric mouse α4β2 nAChR (Nashmi et al., 2003; Drenan et al., 2008; Son et al., 2009) was assessed.

Previous data indicate that α4β2 receptors are retained to a large extent in intracellular compartments (Nashmi et al., 2003; Kuryatov et al., 2005; Sallette et al., 2005; Drenan et al., 2008; Son et al., 2009). As with previous studies of this channel expressed in N2a cells (Drenan et al., 2008; Son et al., 2009), HEK293 cells (Nashmi et al., 2003), transfected neurons (Nashmi et al., 2003; Khakh et al., 2005), and α4YFP knock-in mice (Nashmi et al., 2007), the fluorescence of both α4YFP and β2CFP nAChR subunits appeared evenly throughout the endoplasmic reticulum of N2a cells (FIG. 13A), with a high degree of colocalization (Pearson product-moment correlation coefficient r=0.9±0.02, n=11 cells, data not shown). As described above (FIG. 10), the even fluorescence distribution throughout the cell provided only a single ROI per cell for this transfection: the ROI encompassed the entire cell without the nucleus. This was determined by the pixels exhibiting YFP fluorescence.

Figure 16:
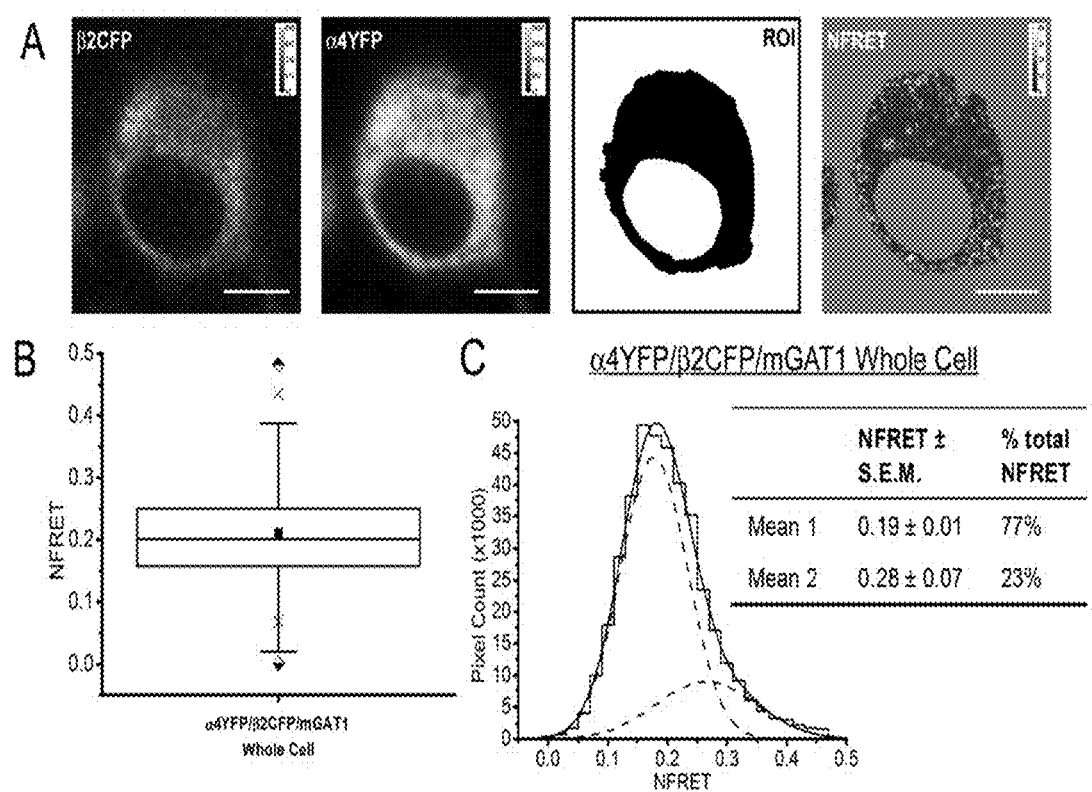
FIG. 16 shows: Pixel-by-pixel quantification of sensitized emission Förster resonance energy transfer within α4YFPβ2CFP nAChRs. A) From left to right, panels display an N2a cell coexpressing β2CFP and α4YFP nAChR subunits with non-fluorescent wild-type mGAT1 (calibration bars=A.C.U.). The whole cell ROI in which FRET was quantified is displayed in black in the third panel. The fourth panel displays the NFRET image (calibration bar=NFRET×100). Pixels with signal amplitude below threshold are shaded gray. Scale bars=10 μM. B) Box plot displaying the range of NFRET detected from α4YFPβ2CFP coexpressing N2a cells. The box, whiskers and other data points are represented as in FIG. 10B. D) Distribution of NFRET signal amplitudes per pixel (bin width 0.02). The histogram was fit to two Gaussian distributions. The individual components are shown as dashed lines and the sum of the fit as a solid line. The inset table reports the mean NFRET amplitude of each component and the percentage of the total pixels that comprise each component.

Robust FRET was observed throughout cells coexpressing α4YFPβ2CFP nAChR subunits; the mean NFRET for all pixels was 0.20 (FIG. 16A, 16B). The distribution of NFRET amplitudes for all analyzed pixels was best fit by two Gaussian components, with mean NFRET of 0.19 (representing 75% of all FRETing pixels) and 0.28 (FIG. 16C). Thus we demonstrate that when expressed in N2a cells in the absence of any nicotinic agonist or antagonists α4β2 nAChRs predominantly reside in intracellular compartments and have NFRET distributions comprising two Gaussian components (FIG. 16). These two components represent the two possible functional stoichiometries of α4 and β2 nAChR subunits, $(\alpha 4)_3(\beta 2)_2$ and $(\alpha 4)_2(\beta 2)_3$ (Son et al., 2009).

Figure 17:
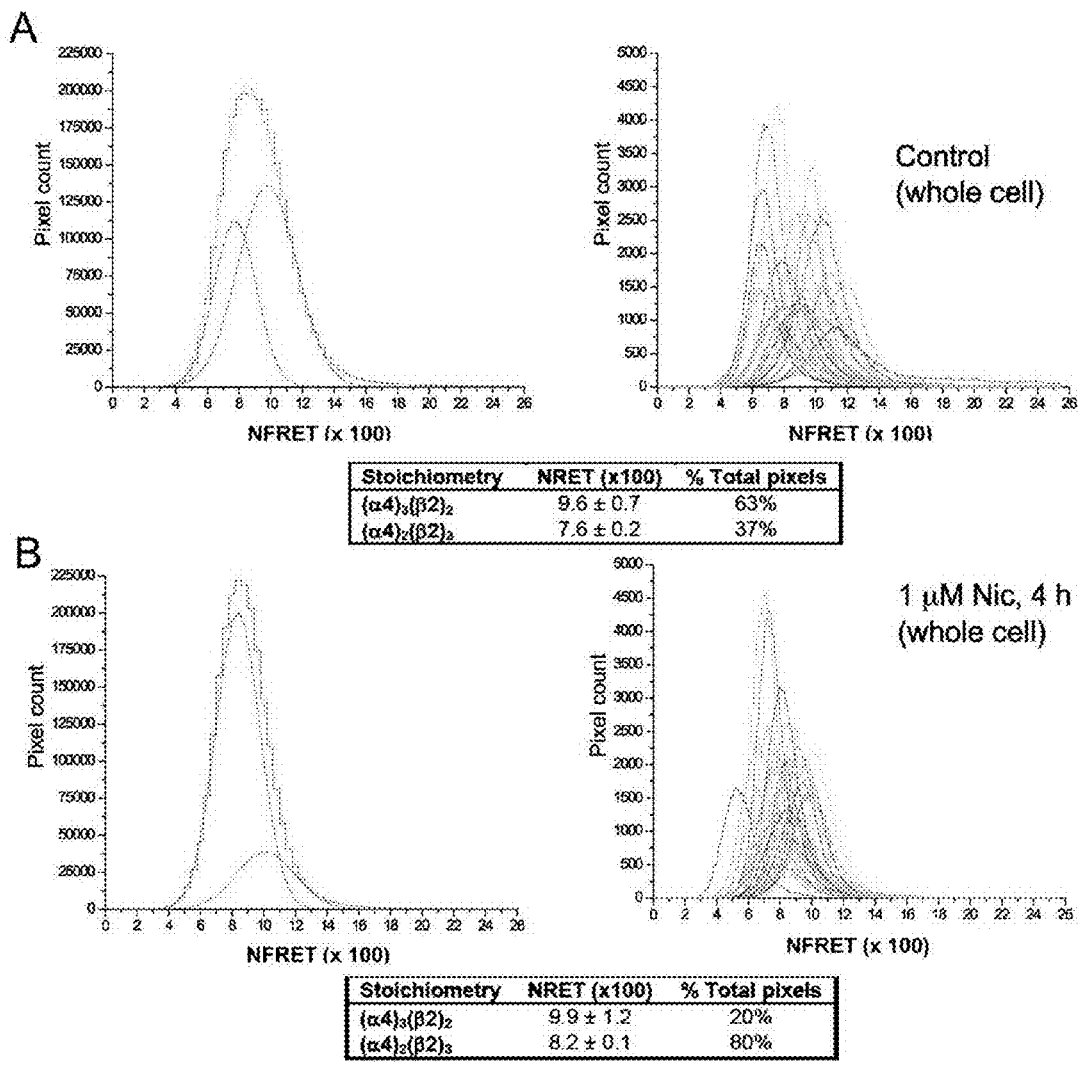
FIG. 17 shows: (A) Gaussian fits to the whole cell NFRET distribution (n=40 cells, 1×10$^6$ pixels; alternate stoichiometries correspond to the subcomponents of the summed fit (left) and the NFRET distributions for the individual cells in the analysis (right) for N2a cells expressing a 1:1 transfection of α4-mCherry and β2-meGFP nAChR subunits. (B) Gaussian fits to the whole cell NFRET distribution following 1 μM nicotine exposure (left) and raw NFRET histograms for the individual cells in the analysis (right). Mean distributions to the individual fits are superimposed (bold lines). Note the dramatic upregulation to the high-sensitivity (α4)$_2$(β4)$_3$ stoichiometry after a 4 h incubation in a saturating dose of nicotine.

In earlier described experiments we were able to quantify receptor upregulation via changes in stoichiometry resulting from nicotine exposure as increases in the mean whole cell FRET efficiency as determined by either acceptor photobleach or sensitized emission. With the methods and systems disclosed herein it is possible to quantify the proportions of the total nAChR population comprised by the $(\alpha 4)_3(\beta 2)_2$ and $(\alpha 4)_2(\beta 2)_3$ stoichiometries in each cell or a particular ROI following exposure to drugs like nicotine. Using α4-mCherry and α2-meGFP fused subunits optimized for pixel based FRET analysis; it was demonstrated that nicotine exposure causes a partial switch in receptor stoichiometry. Whole cell NFRET distribution analysis shows that in the absence of agonist, ~60% of the nAChRs expressed in N2a cells are the $(\alpha 4)_3(\beta 2)_2$ stoichiometry and ~40% the $(\alpha 4)_2(\beta 2)_3$ stoichiometry (FIG. 17A). A 4 h exposure to a saturating dose of nicotine upregulates the receptor population to express 80% of the high-sensitivity $(\alpha 4)_2(\beta 2)_3$ stoichiometry (FIG. 17B). This phenomenon continues for at least 24 h post nicotine exposure. Including a specific organelle marker for the trans-Golgi apparatus in the transfections (GalT-CFP) allowed the FRET from the specific pixels occupied by the trans-Golgi to be quantified (FIG. 18A). 1 µM nicotine resulted in a shift from a mixed population of $(\alpha 4)_2(\beta 2)_3$ and $(\alpha 4)_3(\beta 2)_2$ receptor in the Golgi (FIG. 18C) to a pure $(\alpha 4)_2(\beta 2)_3$ receptor population in the Golgi at 4 h post-exposure (FIG. 18D).

Example 22

Cell- and Receptor Autonomous Upregulation

The shifting in the nAChRs stoichiometry following nicotine administration demonstrated in the previous examples, also supports the conclusion of upregulation if the nAChRs by nicotine.

Upregulation by nicotine occurs when receptors are heterologously expressed in mammalian cell lines, as well as in almost pure cultures of GABAergic ventral midbrain neurons (Nashmi and Lester, 2007; Nashmi et al., 2007). Because in these experiments, nAChRs are upregulated in the very cells that are exposed to nicotine, upregulation is "cell autonomous". Since most upregulation studies including the fluorescence-based assays described in the present disclosure rely on heterologous receptor expression in cell lines, the concept of cell autonomy allows translation of findings from in vitro studies to in vivo systems. In addition to cell autonomy, receptor upregulation is observed to occur in clonal cell lines expressing only α4β2 receptors (Nashmi et al., 2003; Nashmi and Lester, 2007). Furthermore, functional effects similar to upregulation occur at chronic nicotine concentrations that activate only α4 subunit-containing (α4*) receptors (Tapper et al., 2004). These findings, collectively termed "receptor autonomy", show that the activation of other subtypes of nicotinic receptors is not necessary for upregulation.

It is possible to assume that receptor autonomy is important for the normal expression, function and upregulation of exogenously introduced α4β2 nAChRs in immortalized mammalian cells, allowing the study of upregulation using in vitro cellular assays.

Example 22

Screening of Candidate Upregulators Through FRET Measurements of a Cell Line Stably Co-Expressing α4 and β2 nAChRs-Prophetic In this series of experiments, a mouse neuroblastoma (N2a) cell line stably co-expressing fluorescently tagged mouse α4 and β2 nAChR subunits will be generated. A fluorescence-based assay to identify nAChR upregulators will then be developed and validated by screening a small panel of compounds to identify nAChR upregulators.

Engineering of Fluorescently Tagged α4 and β2 Mouse nAChR Plasmid Constructs.

The fluorescently tagged α4 and β2 constructs have been previously constructed and characterized (Nashmi and Lester, 2007; Nashmi et al., 2007; Drenan et al., 2008). These constructs will be re-engineered to express improved XFP moieties with better signal to noise ratios. In addition, the newer XFP variants will possess monomeric structures to prevent receptor assembly artifacts, greater photostability and increased levels of brightness. The cyan fluorescent protein will be replaced with a monomeric variant called Cerulean (Cer) and yellow fluorescent protein (YFP) will be replaced with a monomeric YFP (mYFP) that contains a A206K mutation (Shaner et al., 2005). Preliminary studies comparing β2 CFP nAChR and β2 Cer nAChR have shown that β2 Cer nAChR is brighter and possesses superior signal to noise ratios in functional imaging assays.

Transfection of nAChR Subunits and Selection of Stable Cell Lines.

N2a cells will be transfected with the α and β XFP-containing constructs and selected with neomycin. For transfection, cells will be maintained in DMEM supplemented with 10% fetal bovine serum, 2 mM L-glutamine, 100 U/ml penicillin, and 100 μg/ml streptomycin. Transfections will be carried out with 500 ng of DNA for each construct for a total of 1 μg/well. Cells will then be incubated for 24 hours after transfection and before selection following which transfected cells will be expanded from one 35 mm dish to five 100 mm culture dishes. Transfected cells will then be selected with 10 μg/ml neomycin for 14 days. Neomycin resistant colonies will then be picked by the "grab and stab" method and seeded into 96 well dishes. Colonies will then be allowed to grow to confluence before splitting into duplicate 96 well dishes and freezing one set according to standard procedures.

Screening of Transfected Cell Line Clones for Correct Receptor Assembly.

Glass bottom 96-well culture dishes with selected cell line clones will first be used to assess the presence and intensity of fluorescence. Clones displaying moderate levels of fluorescence intensity for both subunits will then be used to examine the functional assembly of receptors using Förster resonance energy transfer (FRET) analysis. For FRET analysis, the fluorescence intensities of CFP and YFP (for instance) during photobleaching are measured and normalized to time 0 (100%). FRET is recorded by examining the dequenching of CFP during photobleaching of YFP by the 514 nm argon laser as excitation of the CFP occurs at 458 nm. A series of lambda stack X-Y images is collected from the Nikon CIs confocal microscope, at wavelengths between 462.9 and 602 nm (10 nm intervals) during excitation of CFP at 458 nm. FRET efficiency (E) is defined $E=1-(I_{DA}/I_D)$, where $I_{DA}$ represents the normalized fluorescence intensity of CFP (100%) in the presence of both donor and acceptor, and $I_D$ represents the normalized fluorescence intensity of CFP in the presence of donor only. The $I_D$ value is extrapolated from a scatter plot of the percentage increase of CFP versus the percentage decrease of YFP for each cell. Clones with an optimal combination of modest fluorescence intensity, the best fluorescence intensity ratios, clearly discernible FRET and robust cellular division rates will be expanded for further analysis.

Assessment of nAChR Activity in Selected Cell Lines.

Mouse nAChR activity will be assessed in cell lines that display the best combinations of fluorescence intensity and FRET. The cell lines will be tested for nAChR activity by whole cell electrophysiology. The purpose of these tests is to correlate fluorescence intensity and FRET results with receptor activity and to select cell lines displaying good signal to noise ratios and the best correlation between the two studies. In addition to testing receptor activity, whole cell electrophysiology will be used to obtain $EC_{50}$ values to acetylcholine and nicotine, maximal response properties and desensitization profiles for selected α4mYFP-β2Cer cell lines. Selective α4β2 receptor antagonists will be used to determine the z-values of cell lines. The cell line displaying $EC_{50}$ values that are in agreement with published values and favorable z values will be selected for all upregulation studies.

Characterization of Nicotine-Induced Upregulation in Candidate Cell Lines.

For the purposes of developing a drug screening assay, the ability of nicotine to upregulate receptor numbers is of paramount importance. Following the selection of cell line clones using tests for receptor assembly and activity, the cell line displaying the optimum receptor fluorescence and activation profiles will be subjected to upregulation assays. For upregulation assays, nicotine will be applied for 24 h. To test α4mYFP-β2Cer upregulation, the concentration of nicotine exposure will be 1 μM, a concentration equal to that in a smoker's brain. A cell line showing >50% upregulation in patch-clamp experiments and in absolute fluorescence levels of α4 and β2 will be considered as optimal for further use in assay validation. In cases of upregulation, patch clamp recordings should demonstrate a shift toward lower nicotine $EC_{50}$ and a robust increment (>5%) in FRET efficiency (Nashmi et al., 2003). For experiments outlined in this section, the same cell line exposed to vehicle/saline will be used as a negative control.

Screening a Small Chemical Library to Identify α4 and β2-Specific Upregulators.

A stable cell line clone displaying optimal parameters based on the criteria described in previous sections will be selected. The cell line will be incubated with a panel of known compounds. The panel of drugs to be used is outlined in Table 3 along with their known actions and their subunit specificity. The concentration of drugs used will be based on the concentrations at which these drugs are known to exert their pharmacological effects. Upregulation assays will be performed in a manner similar to that described in section 1.5. The cell line incubated with vehicle/saline will be used as a negative control and the same cell line incubated with 1 μM nicotine will be the positive control. Drugs that upregulate α4 and β2 nAChRs will be defined based on robust increments of FRET efficiency (>5%) and >50% upregulation in absolute fluorescence levels that are comparable with the nicotine incubated cell line. In case of receptor agonists, patch clamp experiments will also be used to determine $EC_{50}$ values, which should be lowered in case of upregulators.

TABLE 3

| Drug name | Major subtype | Acute action |
| --- | --- | --- |
| Nicotine | Various | Agonist |
| Cytisine | Various | partial agonist |
| GTS-21 | α7 | partial agonist |
| Varenicline | α4 β2, α3 β4, α7 | partial agonist |
| Cotinine | α7 | partial agonist |
| DHβE | α4β2 | Antagonist |
| aCTX-MII | α6β3* | Antagonist |
| Bupropion | α3β4 | Antagonist |
| Galanthamine | α4β2 | allosteric modulator |
| Hexamethonium | Various | channel blocker |
| Carbachol | All | Agonist |
| QX-314 | Various | channel blocker |
| Choline | α7 | Agonist |
| Chlorisondamine | Various | channel blocker |
| Atropine | Muscarinic | Blocker |

Example 23

Monitoring and Analyzing Upregulation of nAChRs-Prophetic

The functional upregulation of α4β2 neuronal nicotinic acetylcholine receptors (nAChRs) contributes to important aspects of nicotine addiction such as sensitization and tolerance. Several hypotheses exist to explain upregulation. These include nicotine acting as a selective chaperone or maturational enhancer of α4β2 receptors, alterations in receptor turnover and/or trafficking and the initiation of upregulation by receptor desensitization. This series of experiments employs fluorescently tagged nAChRs and high-resolution fluorescence microscopy to clarify the mechanism of receptor upregulation. Potential modulatory roles for α5 and β2 nAChR subunits on receptor localization and trafficking in mouse neuroblastoma (N2a) cells as well as cultured primary neurons will also be explored. Förster resonance energy transfer (FRET) and total internal reflection fluorescence microscopy (TIRFM) will be used in conjunction with electrophysiology to test the effects of nicotine, acetylcholine and dihydro-beta-erythroidine on the intracellular stoichiometry, cell surface expression and trafficking of α4β2* (* denotes that other subunits are present in the receptor) receptors. Results from these studies will provide critical insight into key subcellular events and molecules required for upregulation, thus paving the way for developing novel and more effective smoking cessation therapies.

Example 24

Characterization of Drug-Induced Changes in α4β2 Receptor Stoichiometry-Prophetic A stable N2a cell line expressing monomeric Cherry tagged to mouse α4 nAChR subunits (α4-mCherry) and monomeric enhanced green fluorescent protein tagged to mouse β2 nAChR subunits (β2-meGFP) will be generated. Cell with optimum levels of receptor expression, assembly and function will be chosen and systematically exposed to different concentrations of nicotine, the endogenous nAChR agonist acetylcholine (ACh) and the antagonist dihydro-beta-erythroidine (DHβE). Agonist/antagonist-induced changes in α4β2 nAChR stoichiometry will be assessed in subcellular compartments by FRET measurements, while the density and trafficking of receptors at the plasma membrane following incubation with each drug will be quantified by TIRFM. These experiments will provide more precise information on intracellular changes in nAChR stoichiometry associated with exposure to nicotine, acetylcholine and the nAChR antagonist DHβE. Moreover, TIRFM will enable the direct correlation of intracellular stoichiometry with receptor trafficking to the plasma membrane.

In this series of experiments, N2a cell lines stably co-expressing mouse α4-mCherry and β2-meGFP will be generated. Cell lines will be subject to a battery of imaging tests: confocal microscopy to quantify whole cell fluorescence emission, pixel-by-pixel FRET to assess receptor assembly, TIRM to study ER localization and receptor insertion into the plasma membrane and whole cell electrophysiology to directly measure receptor function.

Clones of stably transfected cells with non-saturated levels of receptor expression, adequate receptor assembly, function and growth rates will be selected and used for further experiments. The cell line with the best expression profile will be transfected with the Golgi marker plasmid, GalT-eCFP, and exposed to nicotine, ACh and DHβE. All drugs will be used at 0.01, 0.1, 1 and 10 μM. These concentrations have been chosen because the 0.1-1 μM range encompasses nicotine concentrations found in the smoker's brain. The ten-fold difference in proposed drug concentrations are expected to result in a spectrum of cellular nAChR upregulation states, which provides a good internal control for proposed experiments.

Changes in receptor stoichiometry induced by incubation with each drug at each concentration used will be separately documented for the whole cell, the Golgi compartment and the periphery. Drug-exposed cells will also be assessed for receptor upregulation at the plasma membrane by TIRFM. It is estimated that 40 cells/drug/concentration will provide a statistically appropriate sample size for FRET, while 20 cells/drug/concentration is sufficient for TIRFM analysis.

Since preliminary results show that nicotine induces a change in stoichiometry at 4 h post-exposure which is sustained for at least 24 h post-exposure, a 4 h time point will be used for FRET. Recent data also show that 4 h of 1 μM nicotine exposure is sufficient to cause upregulation at the plasma membrane and that this can be readily visualized as an increase in punctuate features by TIRFM. Moreover, 4 h incubation allows characterization of early events leading to upregulation. All results from microscopy analysis will be correlated to receptor function using whole cell electrophysiology. EC50 values will be obtained in basal and in upregulated states following the application of increasing acetylcholine (ACh) concentrations. Since high and low sensitivity α4β2 nAChRs possess low and high EC50 values respectively, electrophysiological dose-response relationships will be used to determine the proportion of the two stoichiometries expressed at the membrane in the non-upregulated versus upregulated state.

Figure 19:
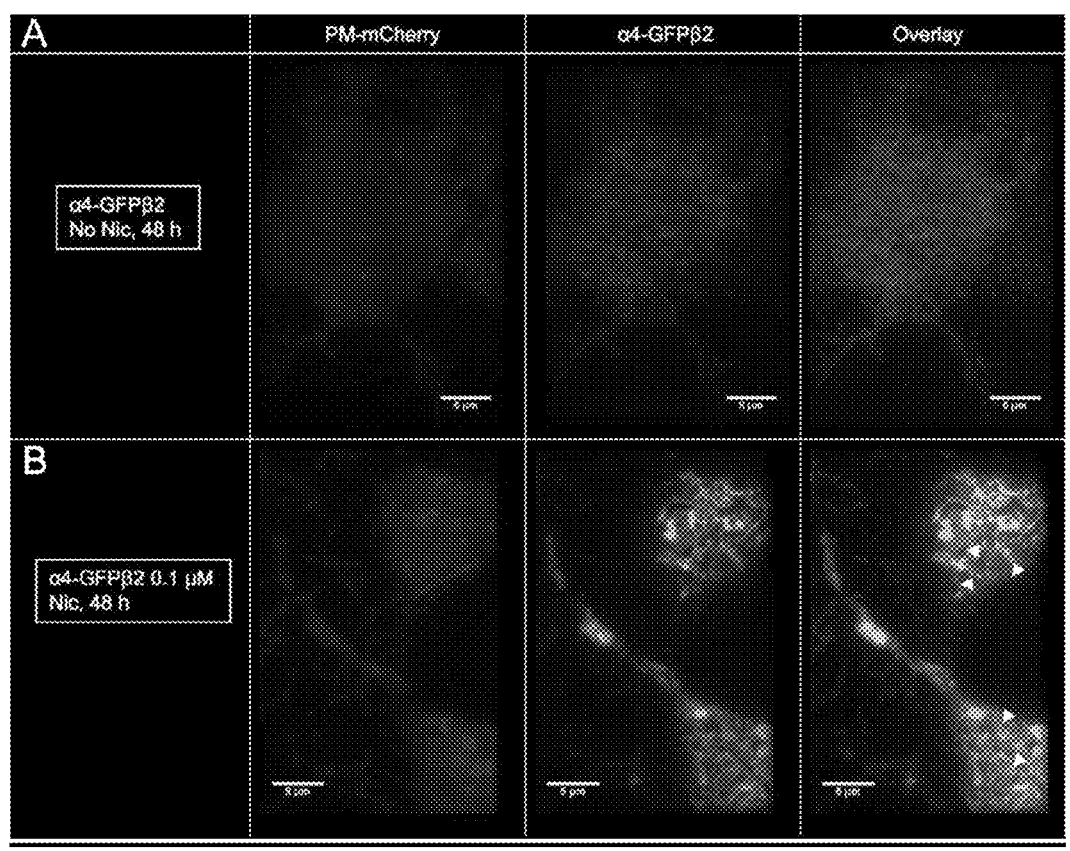
FIG. 19 shows TIRF images reveal reorganization and upregulation of α4β2 receptors after incubation for 48 h in nicotine. Cells were transfected with membrane-targeted mCherry, α4GFP, and unlabeled β2. Left panels, mCherry; middle panels, α4GFP; right panels, overlay. Both control and nicotine-incubated cells show a network of receptors (A, B), but the fluorescence is much brighter after nicotine (B) and diffraction-limited punctuate features representing membrane localized receptors are seen in nicotine incubated cells (white arrows). Note that incubation in nicotine produces patches of α4β2 receptors which may be ER exit sites. Scale bars, 5 μm.

Experiments outlined in this example are expected to provide precise information regarding the intracellular (FIG. 19) changes in nAChR stoichiometry associated with exposure to different nAChR agonists and antagonists, while TIRFM will enable the direct correlation of intracellular stoichiometry with receptor trafficking to the plasma membrane. If for instance, a cell permeable compound like nicotine results in upregulation and a change in stoichiometry to HS, will a largely cell permeable, will largely cell impermeable compound like ACh does not cause upregulation at similar concentrations, this will support to the hypothesis of nicotine-induced selective chaperoning as a mechanism for upregulation. Alternatively, results of the investigation will be able to support conclusion that ACh can increase receptors at the plasma membrane without changing intracellular stoichiometry, a result that would give credence to the existence of nAChR activation-dependent mechanism of upregulation. These results will provide an opportunity to study the effects of stoichiometry on receptor trafficking to the plasma membrane as well as delve into mechanisms by which upregulation occurs. In the distinction of surface versus submembranous receptors visualized by TIRFM electrophysiology is expected to be critical for correlating the receptor number at the plasma membrane obtained by TIRFM with receptor function and EC50 values before and after upregulation.

Example 25

Characterization of the Modulatory Effect of β2 Subunits on α4β2 nAChR Trafficking R×R motifs cause retention of NMDA and HERG channels within the ER (Scott et al., 2001; Scott et al.; Phartiyal et al., 2008). ER retention may likely represent a conserved mechanism to regulate receptor trafficking in living cells and is therefore highly relevant to α4β2 receptor upregulation and trafficking with translational relevance in the area of nicotine addiction and Parkinson's disease. In a series of experiments, the potential regulatory role of β2 subunits in the assembly and trafficking α4β2 receptors was explored. Preliminary studies showed that large numbers of α4β2 receptors are retained in the endoplasmic reticulum (ER) of N2a cells, while α4β4 receptors efficiently traffic to the cell surface. Alignment of the protein sequences of β2 and β4 subunits showed a clear divergence in the protein sequences of these subunits in the M3-M4 domains. In the M3-M4 domains, the β2 subunit possesses an RRQR motif towards the middle of the domain, which was mutated to AAQA (denoted as β2AAQA). N2a cells were transfected with the following sets of cDNA: α4-meGFP+wildtype β2, α4-meGFP+wildtype β4 and α4-meGFP+β2AAQA. Total internal reflection fluorescence microscopy (TIRFM) was used to determine the density of receptors at the plasma membrane. These studies clearly showed that α4β2AAQA receptors exit the ER and insert into the plasma membrane more efficiently than wildtype α4β2 nAChRs and in a manner comparable to α4β4 receptors. NFRET experiments will next be performed to examine the stoichiometry of the mutant α4β2AAQA receptors.

In follow-up experiments, α4 subunit masking of a putative ER retention motif (R×R) in the M3-M4 domain of β4 during receptor assembly, allowing efficient ER exit and surface trafficking of α4β4 will be investigated. Also, β2 R×R motifs remaining unmasked during assembly, thereby preventing α4β2 receptor exit from the ER will also be investigated.

To test the effects of R×R motifs on receptor trafficking, the M3-M4 domains of β2 and β4 nAChR subunits will be interchanged to create chimeric subunits. In parallel, β2 subunit mutants with a disruption of M3-M4 domain R×R motifs will be generated. R×R disruption will be performed as in previous studies showing that a mutation of the last arginine (R) to alanine (A) in R×R sequences is sufficient to prevent ER retention by the R×R motif (Phartiyal et al., 2008). Chimeras will be generated by PCR integration of fragments into parent plasmids, while point mutations will be performed using standard mutagenesis techniques for R×R mutants.

TIRFM measurements will be correlated with functional EC50 measurements obtained by recording electrophysiological responses to increasing concentrations of ACh. Wildtype α4β2 and α4β4 receptors transfected into N2a cells will be used to determine the basal EC50 values and these will be compared to responses obtained following transfections with the different mutant and chimeric receptors.

The experiments outlined in this example have identified key residues in the β2 nAChR subunit that modulate the subcellular localization and trafficking of α4β2 receptors. Since receptor exit from the ER and trafficking to the plasma membrane are integral features of upregulation, the identification of mechanisms by which β2 subunits modulate receptor populations in subcellular compartments will be an important contribution to the field of nicotine addiction. A specific test that the R×R regulatory elements play a key role will be a valuable outcome. Disproof of the hypothesis will allow us to focus on alternative mechanisms for increased ER exit in the presence of nicotine. Research will also focus on the effect of receptor phosphorylation by protein kinases A and C that have been previously shown to induce a rapid translocation of receptors to the cell surface (Nashmi et al., 2003). Perhaps phosphorylation results in conformation changes in assembled receptor of the ER such that the R×R motifs in α4β2 receptors become masked, allowing an exit of these receptors from the ER to the Golgi and finally to the plasma membrane. Constitutively phosphorylated or non-phosphorylated β2 mutants can be generated and the study can be performed in a similar manner as described in this example. The TIRFM methodology in N2a cells has been optimized such that it is possible to easily visualize rapid receptor trafficking events of mutant receptors with high precision in the millisecond timescale.

Example 26

Characterization of the Effects of α5 nAChR Subunits on the Upregulation of α4β2 Receptors-Prophetic A further series of experiments focuses on understanding the modulatory effect of α5 subunits on α4β2 stoichiometry, upregulation and trafficking. Several combinations of XFP tagged (where XFP=mCherry/meGFP [m=monomeric]) and untagged α4, β2 and α5 subunits will be transiently transfected into N2a cells and the number of α5 nAChR subunits that are incorporated during assembly of α4α5β2 receptors in untreated cells will be determined by FRET analysis. A nAChR-XFP subunit combination with robust FRET will be selected from the above experiments to create a stable cell line. This cell line will then be exposed to different concentrations of nicotine, ACh and DHβE and changes of subcellular receptor stoichiometry in the whole cell, at the cell periphery and the Golgi will be determined by FRET analysis. Differences in plasma membrane expression of XFP-tagged α4α5β2 receptors following exposure of cells to nicotine, ACh and DHβE will also be assessed by TIRFM.

The experiments outlines in Examples 24 and 25 focus on studying the mechanisms of upregulation of α4β2 receptors as well as the potential modulatory role of β2 subunits on receptor trafficking. In experiments outlined in this example, the study of modulation of α4β2 receptor assembly and trafficking will be extended to the effects of α5 subunits. α5 nAChR subunits are of interest because: (i) Genome-wide linkage studies show that the chromosomal locus harboring the α5, β4, and α3 subunits is strongly linked to smoking behavior and that polymorphisms associated with nicotine addiction occur nearest to the α5 subunit (Saccone et al., 2007; Amos et al., 2008; Berrettini et al., 2008; Hung et al., 2008; Thorgeirsson et al., 2008), (ii) A proportion of α4β2*, α6β2* receptors, and α3β4* receptors also contain the α5 subunit in regions that are relevant to nicotine addiction as well as withdrawal such as the brain, spinal cord, and autonomic ganglia (Wang et al., 2002; Gahring et al., 2005; Vincler and Eisenach, 2005; Azam et al., 2007; Mao et al., 2007), (iii) The presence of α5 clearly changes receptor upregulation (Mao et al., 2007; Kuryatov et al., 2008), (iv) α5 knockout mice show two diminished measures of nicotine withdrawal: hyperalgesia and somatic signs (Jackson et al., 2008).

The α5 subunit will be engineered to contain either mCherry or meGFP in the M3-M4 domain. Non-crucial regions of the M3-M4 loop, will be selected, that allow the introduction of XFPs such that receptors tagged with XFPs assemble, traffic and function similar to their wildtype counterparts (Nashmi et al., 2003; Drenan et al., 2008). Three such constructs will be tested with electrophysiology in N2a cells and one that expresses well when co-assembled with α4 and β2 will be chosen. In case of ambiguities, a α5 construct will be functionally tagged with the L9'A mutation (Lester et al., 2003) to verify receptor functionality, but will use native M2 regions for the subsequent experiments. A series of transfections in N2a cells using combinations of tagged and untagged α4, α5 and β2 subunits will be examined by FRET to determine the basal stoichiometry of assembled α4α5β2 receptors, exactly as done by Drenan (2008). Table 4 below shows the combinations that will be used and the expected outcome in case of a $(\alpha 4)_2(\alpha 5)_1(\beta 2)_2$ stoichiometry of receptor assembly.

TABLE 4

NFRET outcomes for various transfected nAChR-XFP combinations

| nAChR-XFP combination | Expected outcome for $(\alpha 4)_2(\alpha 5)_1(\beta 2)_2$ stoichiometry |
| --- | --- |
| α5-meGFP + α5-mCherry + β2 | No FRET |
| α5-mCherry + α5-meGFP + α4 + β2 | No FRET |
| α5-mCherry + α4 + β2-meGFP | FRET+ |
| α5-mCherry + α4-meGFP + β2 | FRET+ |
| α5 + α4-meGFP + β2-mCherry | FRET+ |
| α5 + α4-meGFP + α4-mCherry + β2 | FRET+ |
| α5 + α4 + β2-meGFP + β2-mCherry | FRET+, but low | nAChR-XFP combinations that demonstrate robust FRET will be selected to create a stable cell line co-expressing the α4, α5 and β2 subunits. FRET studies, TIRFM and whole cell electrophysiology will be used to confirm receptor assembly and functionality in the cell line. Cells will then be systematically exposed to the different concentrations of nicotine, ACh and DHβE and changes in subcellular stoichiometry at the periphery, ER and Golgi will be determined using pixel-by-pixel FRET. Differences in plasma membrane expression of meGFP-tagged α4α5β2 receptors following exposure of cells to the drugs will also be assessed using TIRFM. As in previous aims, all upregulation experiments will be correlated with whole cell electrophysiology to determine receptor EC50 values following ACh application.

Results from experiments outlined in this example are expected to help determine the basal stoichiometry of α4α5β2 receptors. Although the receptors are expected to be $(\alpha 4)_2(\alpha 5)_1(\beta 2)_2$ this study is expected to directly quantify α5* receptor stoichiometry using FRET analysis. With reference to determination of the best XFP combination to create a stable cell line the α5+α4-meGFP+α4-mCherry+β2 and the α5+α4+β2-meGFP+β2-mCherry combinations is expected to provide the best NFRET values since in these cases the chances of having mCherry and meGFP on adjacent subunits are greatly enhanced. With reference to association between upregulation and a change in intracellular stoichiometry for α4α5β2 receptors, an absence in stoichiometry change is expected in itself to be a valuable piece of information and to point to a unique regulatory role for α5 subunits during upregulation. In this case, TIRFM will be used as a mainstay to determine plasma membrane upregulation following exposure to drugs. In addition to the considerations detailed above, the TIRFM experiments with α4α5β2 receptors are expected to reveal a uniquely different subcellular organization and trafficking pattern for each of the drugs tested when compared with α4β2 receptors. The experiments outlined in this example will thus reveal critical information regarding several aspects of α5 biology that remain to be answered.

Example 27

Study of α4β2 Receptor Upregulation in Primary Cultured Neurons-Prophetic

The experiments outlined in Examples 24, 25 and 26 are directed to develop and define high-resolution TIRF and FRET methods to study the effects of nicotine on α4β2 upregulation and the potential modulation of receptor trafficking by the α5 and β2 subunits. In this example, the results obtained from previous examples are extended to primary neurons in culture. Experiments described in this example will involve transient transfections of cultured primary mouse midbrain neurons with α4-meGFP, β2-mCherry and α5-meGFP nAChRs as either single subunits or as transiently co-expressed combinations of XFP-tagged and untagged subunits. Single subunit transfections will serve as XFP-tagged reporter subunits to enable the study of receptor assembly and trafficking of the natively expressed complementary neuronal subunit.

Transfected neurons will be either untreated or exposed to various concentrations of nicotine and assessed for receptor assembly and trafficking by FRET and TIRFM. Overall, the experiments outlined in this example are expected to help translate findings from studies in N2a cells to a native neuronal system that is highly relevant to understanding the role of α4β2 receptor upregulation in the context of nicotine addiction.

Experiments outlined in Examples 24 to 26 use stably transfected mouse neuroblastoma (N2a) cells to study mechanisms of α4β2 nAChR upregulation and modulation. Since nAChR upregulation in the context of nicotine dependence occurs in midbrain neurons, this set of experiments focuses on extending findings from N2a cells to a native neuronal environment, for example by electrophysiological and optical studies on cultured embryonic mouse midbrain neurons (Nashmi et al., 2003; Nashmi et al., 2007). In culture, a pure GABAergic population of neurons that do not express native receptors during the first week can be obtained, but by the end of the $3^{rd}$ week these neurons express significant levels of α4β2 receptors (Nashmi et al., 2007). In addition, GABAergic neurons from the midbrain do not express native α5 subunits.

This neuronal expression profile will be exploited to transiently transfect week-old neurons with the best FRET combination of α4α5β2 subunits determined from the experiments of Example 26. The neurons will then be treated with 0.01, 0.1, 1 or 10 μM concentrations of nicotine and examined by FRET and TIRFM for changes in receptor trafficking and/or localization. These neurons will also be transfected with α4-meGFP and β2-mCherry and perform experiments similar to the experiments described in Example 24 to determine nicotine-induced changes in receptor stoichiometry and trafficking to the cell surface.

Also three week old neurons will be transfected with either α4-meGFP or β2-meGFP, which will coassemble with their partners, and TIRFM will be used to study the localization and trafficking of natively expressed α4 and β2 nAChRs with and without nicotine treatment. As in previous aims, all microscopy analysis will be used in conjunction with whole cell electrophysiology to measure the functional changes in α4β2 and α4α5β2 receptors that occur as a result of nicotine exposure.

The proposed experiments set forth will assess the relevance of our findings to receptor trafficking in a physiological cellular environment. The kinetics and general mechanisms of upregulation are expected to be similar in neurons and N2a cells, however the documentation of α4β2 upregulation, localization and trafficking in a native cellular environment with subcellular resolution will be useful for the field of nicotine dependence, following FRET and TFRM studies in primary neurons (Nashmi et al., 2003). If glial cells in neuronal cultures prove to be a hinderance for TIRFM, alternative methods such as the use of specialized custom-made imaging dishes with microfluidic channels to allow the growth of only axons will be considered. This strategy will allow TIRFM imaging of the axonal terminals, a site that is extremely relevant to upregulation. In addition, should transiently expressed subunits will not be able to efficiently assemble with endogenous wildtype subunits because of differences in expression levels and subcellular localization, neurons from α4 or β2 knockout mice will be transfected and tested with the complimentary subunit tagged to a reporter XFP. This strategy is expected to provide a genetically pure intracellular environment for receptor assembly and trafficking.

In summary, the present disclosure provides in several embodiments methods that allow simultaneous detection and quantification of the steady state stoichiometries present in the same region of interest within a sample and detection and quantification of the modulation of complex stoichiometry that results from changes in the surrounding environment or the introduction of genetic mutations.

The examples set forth above are provided to give those of ordinary skill in the art a complete disclosure and description of how to make and use the embodiments of the methods, and systems of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually.

Further, the hard copy of the sequence listing submitted herewith and the corresponding computer readable form are both incorporated herein by reference in their entireties.

It is to be understood that the disclosures are not limited to particular compositions materials, or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

AbdAlla, S., H. Lother, A. el Massiery, and U. Quitterer. 2001. Increased $AT_1$ receptor heterodimers in preeclampsia mediate enhanced angiotensin II responsiveness. *Nat Med.* 7:1003-1009.

Amos, C. I., X. Wu, P. Broderick, I. P. Gorlov, J. Gu, T. Eisen, Q. Dong, Q. Zhang, X. Gu, J. Vijayakrishnan, K. Sullivan, A. Matakidou, Y. Wang, G. Mills, K. Doheny, Y. Y. Tsai, W. V. Chen, S. Shete, M. R. Spitz, and R. S. Houlston. 2008. Genome-wide association scan of tag SNPs identifies a susceptibility locus for lung cancer at 15q25.1. *Nat Genet.* 40:616-622.

Azam, L., Y. Chen, and F. M. Leslie. 2007. Developmental regulation of nicotinic acetylcholine receptors within midbrain dopamine neurons. *Neuroscience.* 144:1347-1360.

Berrettini, W., X. Yuan, F. Tozzi, K. Song, C. Francks, H. Chilcoat, D. Waterworth, P. Muglia, and V. Mooser. 2008. α5/α3 nicotinic receptor subunit alleles increase risk for heavy smoking. *Mol Psychiatry.* 13:368-373.

Bethony, J., S. Brooker, M. Albonico, S. M. Geiger, A. Loukas, D. Diemert, and P. J. Hotez. 2006. Soil-transmitted helminth infections: ascariasis, trichuriasis, and hookworm. *Lancet.* 367:1521-1532.

Boudanova, E., D. M. Navaroli, Z. Stevens, and H. E. Melikian. 2008. Dopamine transporter endocytic determinants: carboxy terminal residues critical for basal and PKC-stimulated internalization. *Mol Cell Neurosci.* 39:211-217.

Briggs, C. A., E. J. Gubbins, M. J. Marks, C. B. Putman, R. Thimmapaya, M. D. Meyer, and C. S. Surowy. 2006. Untranslated region-dependent exclusive expression of high-sensitivity subforms of α4β2 and α3β2 nicotinic acetylcholine receptors. *Mol Pharmacol.* 70:227-240.

Brodtkorb, E., and F. Picard. 2006. Tobacco habits modulate autosomal dominant nocturnal frontal lobe epilepsy. *Epilepsy Behav.* 9:515-520.

Bruckner, K., J. Pablo Labrador, P. Scheiffele, A. Herb, P. H. Seeburg, and R. Klein. 1999. EphrinB ligands recruit GRIP family PDZ adaptor proteins into raft membrane microdomains. *Neuron.* 22:511-524.

Buisson, B., and D. Bertrand. 2001. Chronic exposure to nicotine upregulates the human α4β2 nicotinic acetylcholine receptor function. *J Neurosci.* 21:1819-1829.

Carriba, P., O. Ortiz, K. Patkar, Z. Justinova, S. Stroik, A. Themann, C. Muller, A. S. Woods, B. T. Hope, F. Ciruela, V. Casado, E. I. Canela, C. Lluis, S. R. Goldberg, R. Moratalla, R. Franco, and S. Ferre. 2007. Striatal adenosine $A_{2A}$ and cannabinoid $CB_1$ receptors form functional heteromeric complexes that mediate the motor effects of cannabinoids. *Neuropsychopharmacology.* 32:2249-2259.

Chiu, C. S., K. Jensen, I. Sokolova, D. Wang, M. Li, P. Deshpande, N. Davidson, I. Mody, M. W. Quick, S. R. Quake, and H. A. Lester. 2002. Number, density, and surface/cytoplasmic distribution of GABA transporters at presynaptic structures of knock-in mice carrying GABA transporter subtype 1-green fluorescent protein fusions. *J Neurosci.* 22:10251-10266.

Combi, R., L. Dalpra, M. L. Tenchini, and L. Ferini-Strambi. 2004. Autosomal dominant nocturnal frontal lobe epilepsy—a critical overview. *J Neurol.* 251:923-934.

Corry, B., D. Jayatilaka, B. Martinac, and P. Rigby. 2006. Determination of the orientational distribution and orientation factor for transfer between membrane-bound fluorophores using a confocal microscope. *Biophys J.* 91:1032-1045.

Corry, B., D. Jayatilaka, and P. Rigby. 2005. A flexible approach to the calculation of resonance energy transfer efficiency between multiple donors and acceptors in complex geometries. *Biophys J.* 89:3822-3836.

Crompton, D. W. 2001. *Ascaris* and ascariasis. *Adv Parasitol.* 48:285-375.

Drenan, R. M., R. Nashmi, P. I. Imoukhuede, H. Just, S. McKinney, and H. A. Lester. 2008. Subcellular Trafficking, Pentameric Assembly and Subunit Stoichiometry of Neuronal Nicotinic ACh Receptors Containing Fluorescently-Labeled α6 and β3 Subunits. *Mol Pharmacol.* 73:27-41.

Elangovan, M., H. Wallrabe, Y. Chen, R. N. Day, M. Barroso, and A. Periasamy. 2003. Characterization of one- and two-photon excitation fluorescence resonance energy transfer microscopy. *Methods.* 29:58-73.

Farhan, H., V. Reiterer, V. M. Korkhov, J. A. Schmid, M. Freissmuth, and H. H. Sitte. 2007. Concentrative Export from the Endoplasmic Reticulum of the γ-Aminobutyric Acid Transporter 1 Requires Binding to SEC24D. *J Biol. Chem.* 282:7679-7689.

Farhan, H., V. Reiterer, A. Kriz, H. P. Hauri, M. Pavelka, H. H. Sine, and M. Freissmuth. 2008. Signal-dependent export of GABA transporter 1 from the ER-Golgi intermediate compartment is specified by a C-terminal motif. *J Cell Sci.* 121:753-761.

Feige, J. N., D. Sage, W. Wahli, B. Desvergne, and L. Gelman. 2005. PixFRET, an ImageJ plug-in for FRET calculation that can accommodate variations in spectral bleed-throughs. *Microsc Res Tech.* 68:51-58.

Figl, A., N. Viseshakul, N. Shafaee, J. Forsayeth, and B. N. Cohen. 1998. Two mutations linked to nocturnal frontal lobe epilepsy cause use-dependent potentiation of the nicotinic ACh response. *J Physiol (Lond).* 513:655-670.

Gahring, L. C., K. Persiyanov, and S. W. Rogers. 2005. Mouse strain-specific changes in nicotinic receptor expression with age. *Neurobiol Aging.* 26:973-980.

Geiser, M., R. Cebe, D. Drewello, and R. Schmitz. 2001. Integration of PCR fragments at any specific site within cloning vectors without the use of restriction enzymes and DNA ligase. *Biotechniques.* 31:88-90, 92.

Gonzalez-Maeso, J., R. L. Ang, T. Yuen, P. Chan, N. V. Weisstaub, J. F. Lopez-Gimenez, M. Zhou, Y. Okawa, L. F. Callado, G. Milligan, J. A. Gingrich, M. Filizola, J. J. Meana, and S. C. Sealfon. 2008. Identification of a serotonin/glutamate receptor complex implicated in psychosis. *Nature.* 452:93-97.

Gordon, G. W., G. Berry, X. H. Liang, B. Levine, and B. Herman. 1998. Quantitative fluorescence resonance energy transfer measurements using fluorescence microscopy. *Biophys J.* 74:2702-2713.

Hachet-Haas, M., N. Converset, O. Marchal, H. Matthes, S. Gioria, J. L. Galzi, and S. Lecat. 2006. FRET and colocalization analyzer—a method to validate measurements of sensitized emission FRET acquired by confocal microscopy and available as an ImageJ Plug-in. *Microsc Res Tech.* 69:941-956.

Hanna, S. T. 2006. Nicotine effect on cardiovascular system and ion channels. *J Cardiovasc Pharmacol.* 47:348-358.

Holton, K. L., M. K. Loder, and H. E. Melikian. 2005. Nonclassical, distinct endocytic signals dictate constitutive and PKC-regulated neurotransmitter transporter internalization. *Nat. Neurosci.* 8:881-888.

Hung, A. Y., and M. Sheng. 2002. PDZ domains: structural modules for protein complex assembly. *J Biol. Chem.* 277: 5699-5702.

Hung, R. J., J. D. McKay, V. Gaborieau, P. Boffetta, M. Hashibe, D. Zaridze, A. Mukeria, N. Szeszenia-Dabrowska, J. Lissowska, P. Rudnai, E. Fabianova, D. Mates, V. Bencko, L. Foretova, V. Janout, C. Chen, G. Goodman, J. K. Field, T. Liloglou, G. Xinarianos, A. Cassidy, J. McLaughlin, G. Liu, S. Narod, H. E. Krokan, F. Skorpen, M. B. Elvestad, K. Hveem, L. Vatten, J. Linseisen, F. Clavel-Chapelon, P. Vineis, H. B. Bueno-de-Mesquita, E. Lund, C. Martinez, S. Bingham, T. Rasmuson, P. Hainaut, E. Riboli, W. Ahrens, S. Benhamou, P. Lagiou, D. Trichopoulos, I. Holcatova, F. Merletti, K. Kjaerheim, A. Agudo, G. Macfarlane, R. Talamini, L. Simonato, R. Lowry, D. I. Conway, A. Znaor, C. Healy, D. Zelenika, A. Boland, M. Delepine, M. Foglio, D. Lechner, F. Matsuda, H. Blanche, I. Gut, S. Heath, M. Lathrop, and P. Brennan. 2008. A susceptibility locus for lung cancer maps to nicotinic acetylcholine receptor subunit genes on 15q25. *Nature.* 452:633-637.

Imoukhuede, P. I., F. J. Moss, D. J. Michael, R. H. Chow, and H. A. Lester. 2009. Ezrin mediates tethering of the γ-aminobutyric acid transporter GAT1 to actin filaments via a C-terminal PDZ-interacting domain. *Biophys J.* 96:2949-2960.

Innocent, N., P. D. Livingstone, A. Hone, A. Kimura, T. Young, P. Whiteaker, J. M. McIntosh, and S. Wonnacott. 2008. αConotoxin Arenatus IB[V111, V16D] is a potent and selective antagonist at rat and human native α7 nicotinic acetylcholine receptors. *J Pharmacol Exp Ther.* 327: 529-537.

Jackson, K. J., B. R. Martin, J. P. Changeux, and M. I. Damaj. 2008. Differential role of nicotinic acetylcholine receptor subunits in physical and affective nicotine withdrawal signs. *J Pharmacol Exp Ther.* 325:302-312.

Jares-Erijman, E. A., and T. M. Jovin. 2006. Imaging molecular interactions in living cells by FRET microscopy. *Curr Opin Chem. Biol.* 10:409-416.

Kerschensteiner, D., F. Soto, and M. Stocker. 2005. Fluorescence measurements reveal stoichiometry of $K^+$ channels formed by modulatory and delayed rectifier α-subunits. *Proc Natl Acad Sci USA.* 102:6160-6165.

Khakh, B. S., J. A. Fisher, R. Nashmi, D. N. Bowser, and H. A. Lester. 2005. An angstrom scale interaction between plasma membrane ATP-gated $P_2X_2$ and α4β2 nicotinic channels measured with fluorescence resonance energy transfer and total internal reflection fluorescence microscopy. *J. Neurosci.* 25:6911-6920.

Kuryatov, A., J. Luo, J. Cooper, and J. Lindstrom. 2005. Nicotine acts as a pharmacological chaperone to up-regulate human α4β2 acetylcholine receptors. *Mol. Pharmacol.* 68:1839-1851.

Kuryatov, A., J. Onksen, and J. Lindstrom. 2008. Roles of accessory subunits in α4β2α5 nicotinic receptors. *Mol Pharmacol.* 74:132-143.

Lakowicz, J. R. 2006. Energy Transfer. In Principles of fluorescence spectroscopy. J. R. Lakowicz, editor. Springer Science, New York. 443-476.

Lester, H., C. Fonck, A. Tapper, S. McKinney, M. Damaj, S. Balogh, J. Owens, J. Wehner, A. Collins, and C. Labarca. 2003. Hypersensitive knock-in mouse strains identify receptors and pathways for nicotine action. *Current Opinion in Drug Development.* 6:633-639.

Lester, H. A., C. Xiao, R. Srinivasan, C. D. Son, J. Miwa, R. Pantoja, M. R. Banghart, D. A. Dougherty, A. M. Goate, and J. C. Wang. 2009. Nicotine is a selective pharmacological chaperone of acetylcholine receptor number and stoichiometry. Implications for drug discovery. *Aaps J.* 11:167-177.

Lin, D., G. D. Gish, Z. Songyang, and T. Pawson. 1999. The carboxyl terminus of B class ephrins constitutes a PDZ domain binding motif. *J Biol. Chem.* 274:3726-3733.

Madsen, K. L., T. Beuming, M. Y. Niv, C. W. Chang, K. K. Dev, H. Weinstein, and U. Gether. 2005. Molecular determinants for the complex binding specificity of the PDZ domain in PICK1. *J Biol. Chem.* 280:20539-20548.

Mao, D., D. C. Perry, R. P. Yasuda, B. B. Wolfe, and K. J. Kellar. 2007. The α4β2α5 nicotinic cholinergic receptor in rat brain is resistant to up-regulation by nicotine in vivo. *J Neurochem.*

Marks, M. J., J. B. Burch, and A. C. Collins. 1983. Effects of chronic nicotine infusion on tolerance development and nicotinic receptors. *J Pharmacol Exp Ther.* 226:817-825.

Miranda, P., D. G. Manso, F. Barros, L. Carretero, T. E. Hughes, C. Alonso-Ron, P. Dominguez, and P. de la Pena. 2008. FRET with multiply labeled HERG K+ channels as a reporter of the in vivo coarse architecture of the cytoplasmic domains. *Biochim Biophys Acta.* 1783:1681-1699.

Moroni, M., R. Zwart, E. Sher, B. K. Cassels, and I. Bermudez. 2006. α4β2 nicotinic receptors with high and low acetylcholine sensitivity: pharmacology, stoichiometry, and sensitivity to long-term exposure to nicotine. *Mol Pharmacol.* 70:755-768.

Moss, F. J., P. I. Imoukhuede, K. Scott, J. Hu, J. L. Jankowsky, M. W. Quick, and H. A. Lester. 2009. GABA transporter function, oligomerization state, and anchoring: correlates with subcellularly resolved FRET. *J Gen Physiol.* 134:489-521.

Nashmi, R., M. E. Dickinson, S. McKinney, M. Jareb, C. Labarca, S. E. Fraser, and H. A. Lester. 2003. Assembly of α4β2 nicotinic acetylcholine receptors assessed with functional fluorescently labeled subunits: effects of localization, trafficking, and nicotine-induced upregulation in clonal mammalian cells and in cultured midbrain neurons. *J Neurosci.* 23:11554-11567.

Nashmi, R., and H. Lester. 2007. Cell autonomy, receptor autonomy, and thermodynamics in nicotine receptor up-regulation. *Biochem Pharmacol.* 74:1145-1154.

Nashmi, R., C. Xiao, P. Deshpande, S. McKinney, S. R. Grady, P. Whiteaker, Q. Huang, T. McClure-Begley, J. M. Lindstrom, C. Labarca, A. C. Collins, M. J. Marks, and H. A. Lester. 2007. Chronic nicotine cell specifically upregulates functional α4* nicotinic receptors: basis for both tolerance in midbrain and enhanced long-term potentiation in perforant path. *J. Neurosci.* 27:8202-8218.

Nelson, M. E., A. Kuryatov, C. H. Choi, Y. Zhou, and J. Lindstrom. 2003. Alternate stoichiometries of α4β2 nicotinic acetylcholine receptors. *Mol Pharmacol.* 63:332-341.

Nguyen, H. N., B. A. Rasmussen, and D. C. Perry. 2003. Subtype-selective up-regulation by chronic nicotine of high-affinity nicotinic receptors in rat brain demonstrated by receptor autoradiography. *J Pharmacol Exp Ther.* 307:1090-1097.

Oldani, A., M. Zucconi, R. Asselta, M. Modugno, M. T. Bonati, L. Dalpra, M. Malcovati, M. L. Tenchini, S. Smirne, and L. Ferini-Strambi. 1998. Autosomal dominant nocturnal frontal lobe epilepsy. A video-polysomnographic and genetic appraisal of 40 patients and delineation of the epileptic syndrome. *Brain.* 121:205-223.

Ormo, M., A. B. Cubitt, K. Kallio, L. A. Gross, R. Y. Tsien, and S. J. Remington. 1996. Crystal structure of the *Aequorea victoria* green fluorescent protein. *Science.* 273:1392-1395.

Phartiyal, P., H. Sale, E. M. Jones, and G. A. Robertson. 2008. Endoplasmic reticulum retention and rescue by heteromeric assembly regulate human ERG 1a/1b surface channel composition. *J Biol. Chem.* 283:3702-3707.

Raicu, V. 2007. Efficiency of Resonance Energy Transfer in Homo-Oligomeric Complexes of Proteins. *J Biol Phys.* 33:109-127.

Rizzo, M. A., G. Springer, K. Segawa, W. R. Zipfel, and D. W. Piston. 2006. Optimization of pairings and detection conditions for measurement of FRET between cyan and yellow fluorescent proteins. *Microsc Microanal.* 12:238-254.

Rodrigues-Pinguet, N., L. Jia, M. Li, A. Figl, A. Klaassen, A. Truong, H. A. Lester, and B. N. Cohen. 2003. Five ADNFLE mutations reduce the $Ca^{2+}$ dependence of the α4β2 acetylcholine response. *J Physiol.* 550:11-26.

Rodrigues-Pinguet, N. O., T. J. Pinguet, A. Figl, H. A. Lester, and B. N. Cohen. 2005. Mutations linked to autosomal dominant nocturnal frontal lobe epilepsy affect allosteric $Ca^{2+}$ activation of the α4β2 nicotinic acetylcholine receptor. *Mol Pharmacol.* 68:487-501.

Saccone, S. F., A. L. Hinrichs, N. L. Saccone, G. A. Chase, K. Konvicka, P. A. Madden, N. Breslau, E. O. Johnson, D. Hatsukami, O. Pomerleau, G. E. Swan, A. M. Goate, J. Rutter, S. Bertelsen, L. Fox, D. Fugman, N. G. Martin, G. W. Montgomery, J. C. Wang, D. G. Ballinger, J. P. Rice, and L. J. Bierut. 2007. Cholinergic nicotinic receptor genes implicated in a nicotine dependence association study targeting 348 candidate genes with 3713 SNPs. *Hum Mol Genet.* 16:36-49.

Sallette, J., S. Pons, A. Devillers-Thiery, M. Soudant, L. Prado de Carvalho, J. P. Changeux, and P. J. Corringer. 2005. Nicotine upregulates its own receptors through enhanced intracellular maturation. *Neuron.* 46:595-607.

Scheffer, I. E., K. P. Bhatia, I. Lopes-Cendes, D. R. Fish, C. D. Marsden, E. Andermann, F. Andermann, R. Desbiens, D. Keene, F. Cendes, and et al. 1995. Autosomal dominant nocturnal frontal lobe epilepsy. A distinctive clinical disorder. *Brain.* 118:61-73.

Scholze, P., M. Freissmuth, and H. H. Sitte. 2002. Mutations within an intramembrane leucine heptad repeat disrupt oligomer formation of the rat GABA transporter 1. *J Biol Chem.* 277:43682-43690.

Schwartz, R. D., and K. J. Kellar. 1983. Nicotinic cholinergic receptor binding sites in the brain: regulation in vivo. *Science.* 220:214-216.

Scott, D. B., T. A. Blanpied, and M. D. Ehlers. 2003. Coordinated PKA and PKC phosphorylation suppresses RxR-mediated ER retention and regulates the surface delivery of NMDA receptors. *Neuropharmacology.* 45:755-767.

Scott, D. B., T. A. Blanpied, G. T. Swanson, C. Zhang, and M. D. Ehlers. 2001. An NMDA receptor ER retention signal regulated by phosphorylation and alternative splicing. *J Neurosci.* 21:3063-3072.

Sekar, R. B., and A. Periasamy. 2003. Fluorescence resonance energy transfer (FRET) microscopy imaging of live cell protein localizations. *J Cell Biol.* 160:629-633.

Shaner, N. C., R. E. Campbell, P. A. Steinbach, B. N. Giepmans, A. E. Palmer, and R. Y. Tsien. 2004. Improved monomeric red, orange and yellow fluorescent proteins derived from *Discosoma* sp. red fluorescent protein. *Nat. Biotechnol.* 22:1567-1572.

Shaner, N. C., P. A. Steinbach, and R. Y. Tsien. 2005. A guide to choosing fluorescent proteins. *Nat. Methods.* 2:905-909.

Sheng, M., and C. Sala. 2001. PDZ domains and the organization of supramolecular complexes. *Annu Rev Neurosci.* 24:1-29.

Son, C. D., F. J. Moss, B. N. Cohen, and H. A. Lester. 2009. Nicotine normalizes intracellular subunit stoichiometry of nicotinic receptors carrying mutations linked to autosomal dominant nocturnal frontal lobe epilepsy. *Mol Pharmacol.* 75:1137-1148.

Spudich, G., X. M. Fernandez-Suarez, and E. Birney. 2007. Genome browsing with Ensembl: a practical overview. *Brief Funct Genomic Proteomic.* 6:202-219.

Staruschenko, A., E. Adams, R. E. Booth, and J. D. Stockand. 2005. Epithelial Na+ channel subunit stoichiometry. *Biophys J.* 88:3966-3975.

Steinlein, O. K., A. Magnusson, J. Stoodt, S. Bertrand, S. Weiland, S. F. Berkovic, K. O, Nakken, P. Propping, and D. Bertrand. 1997. An insertion mutation of the CHRNA4 gene in a family with autosomal dominant nocturnal frontal lobe epilepsy. *Hum Mol Genet.* 6:943-947.

Stewart, T. B., and O. M. Hale. 1988. Losses to internal parasites in swine production. *J Anim Sci.* 66:1548-1554.

Tapper, A., S. McKinney, R. Nashmi, J. Schwarz, P. Deshpande, C. Labarca, P. Whiteaker, A. Collins, and H. Lester. 2004. Nicotine activation of α4* receptors: sufficient for reward, tolerance and sensitization. *Science.* 306:1029-1032.

Teper, Y., D. Whyte, E. Cahir, H. A. Lester, S. R. Grady, M. J. Marks, B. N. Cohen, C. Fonck, T. McClure-Begley, J. M. McIntosh, C. Labarca, A. Lawrence, F. Chen, I. Gantois, P. J. Davies, S. Petrou, M. Murphy, J. Waddington, M. K. Horne, S. F. Berkovic, and J. Drago. 2007. Nicotine-induced dystonic arousal complex in a mouse line harboring a human autosomal dominant nocturnal frontal lobe epilepsy mutation. *J. Neurosci.* 27:10128-10142.

Thorgeirsson, T. E., F. Geller, P. Sulem, T. Rafnar, A. Wiste, K. P. Magnusson, A. Manolescu, G. Thorleifsson, H. Stefansson, A. Ingason, S. N. Stacey, J. T. Bergthorsson, S. Thorlacius, J. Gudmundsson, T. Jonsson, M. Jakobsdottir, J. Saemundsdottir, O. Olafsdottir, L. J. Gudmundsson, G. Bjornsdottir, K. Kristjansson, H. Skuladottir, H. J. Isaksson, T. Gudbjartsson, G. T. Jones, T. Mueller, A. Gottsater, A. Flex, K. K. Aben, F. de Vegt, P. F. Mulders, D. Isla, M. J. Vidal, L. Asin, B. Saez, L. Murillo, T. Blondal, H. Kolbeinsson, J. G. Stefansson, I. Hansdottir, V. Runarsdottir, R. Pola, B. Lindblad, A. M. van Rij, B. Dieplinger, M. Haltmayer, J. I. Mayordomo, L. A. Kiemeney, S. E. Matthiasson, H. Oskarsson, T. Tyrfingsson, D. F. Gudbjartsson, J. R. Gulcher, S. Jonsson, U. Thorsteinsdottir, A. Kong, and K. Stefansson. 2008. A variant associated with nicotine dependence, lung cancer and peripheral arterial disease. *Nature.* 452:638-642.

Torres, R., B. L. Firestein, H. Dong, J. Staudinger, E. N. Olson, R. L. Huganir, D. S. Bredt, N. W. Gale, and G. D. Yancopoulos. 1998. PDZ proteins bind, cluster, and synaptically colocalize with Eph receptors and their ephrin ligands. *Neuron.* 21:1453-1463.

Touroutine, D., R. M. Fox, S. E. Von Stetina, A. Burdina, D. M. Miller, 3rd, and J. E. Richmond. 2005. acr-16 encodes an essential subunit of the levamisole-resistant nicotinic receptor at the *Caenorhabditis elegans* neuromuscular junction. *J Biol. Chem.* 280:27013-27021.

Unwin, N. 2005. Refined structure of the nicotinic acetylcholine receptor at 4 Å resolution. *J Mol. Biol.* 346:967-989.

Vincler, M. A., and J. C. Eisenach. 2005. Knock down of the α5 nicotinic acetylcholine receptor in spinal nerve-ligated rats alleviates mechanical allodynia. *Pharmacol Biochem Behav.* 80:135-143.

Wallrabe, H., and A. Periasamy. 2005. Imaging protein molecules using FRET and FLIM microscopy. *Curr Opin Biotechnol.* 16:19-27.

Wang, N., A. Orr-Urtreger, J. Chapman, R. Rabinowitz, R. Nachman, and A. D. Korczyn. 2002. Autonomic function in mice lacking α5 neuronal nicotinic acetylcholine receptor subunit. *J. Physiol.* 542:347-354.

Williamson, S. M., A. P. Robertson, L. Brown, T. Williams, D. J. Woods, R. J. Martin, D. B. Sattelle, and A. J. Wolstenholme. 2009. The nicotinic acetylcholine receptors of the parasitic nematode *Ascaris suum*: formation of two distinct drug targets by varying the relative expression levels of two subunits. *PLoS Pathog.* 5:e1000517.

Williamson, S. M., T. K. Walsh, and A. J. Wolstenholme. 2007. The cys-loop ligand-gated ion channel gene family of *Brugia malayi* and *Trichinella spiralis*: a comparison with *Caenorhabditis elegans*. *Invert Neurosci.* 7:219-226.

Willoughby, J. O., K. J. Pope, and V. Eaton. 2003. Nicotine as an antiepileptic agent in ADNFLE: an N-of-one study. *Epilepsia.* 44:1238-1240.

Wimmer, V. C., H. A. Lester, and S. Petrou. 2008. Ion channel mutations in familial epilepsy. In Encyclopedia of Basic Epilepsy Research. P. A. Schwartzkroin, editor. Elsevier, Oxford.

Wong, J. Y., S. A. Ross, C. McColl, J. S. Massalas, E. Powney, D. I. Finkelstein, M. Clark, M. K. Horne, S. F. Berkovic, and J. Drago. 2002. Proconvulsant-induced seizures in α4 nicotinic acetylcholine receptor subunit knockout mice. *Neuropharmacology.* 43:55-64.

Wu, W. K., and C. H. Cho. 2004. The pharmacological actions of nicotine on the gastrointestinal tract. *J Pharmacol Sci.* 94:348-358.

Xia, Z., and Y. Liu. 2001. Reliable and global measurement of fluorescence resonance energy transfer using fluorescence microscopes. *Biophys J.* 81:2395-2402.

Yamashita, A., S. K. Singh, T. Kawate, Y. Jin, and E. Gouaux. 2005. Crystal structure of a bacterial homologue of Na+/Cl−-dependent neurotransmitter transporters. *Nature.* 437:215-223.

Zacharias, D. A., J. D. Violin, A. C. Newton, and R. Y. Tsien. 2002. Partitioning of lipid-modified monomeric GFPs into membrane microdomains of live cells. *Science.* 296:913-916.

Zhang, Y. W., and G. Rudnick. 2006. The cytoplasmic substrate permeation pathway of serotonin transporter. *J Biol. Chem.* 281:36213-36220.

Zheng, J., and W. N. Zagotta. 2004. Stoichiometry and assembly of olfactory cyclic nucleotide-gated channels. *Neuron.* 42:411-421.

What is claimed is:

1. A method to detect one or more stoichiometries of a protein complex, the method comprising:
    providing theoretically calculated Förster resonance energy transfer (FRET) efficiencies for the one or more stoichiometries of the protein complex;
    performing FRET imaging on a region of interest expressing fluorescently labeled oligomer subunits of the protein complex to provide an acquired FRET image, the acquired FRET image having a plurality of pixels each pixel having a FRET signal amplitude;
    calculating mean FRET efficiencies from the FRET signals amplitudes; and
    correlating the calculated mean FRET efficiencies with the theoretically calculated FRET efficiencies to detect the one or more stoichiometries of the protein complex.

2. The method of claim 1, wherein the calculating is performed by compiling a FRET distribution of the identified FRET amplitudes and the correlating is performed by identifying in the FRET distribution, FRET distribution components based on the theoretically calculated FRET efficiencies.

3. The method of claim 1, wherein the region of interest comprises a plurality of regions.

4. A method to identify a compound capable of regulating a plasma membrane protein complex, the method comprising:
    detecting alternative stoichiometries of the protein complex in a region of interest with the method of claim 1;
    quantifying a ratio of the detected alternative stoichiometries of the protein complex in the region of interest;
    contacting the protein complex in the region of interest with a candidate compound; and
    quantitatively detecting changes in the quantified ratio of detected alternative stoichiometries of the protein complex in the region of interest following contact of the candidate compound; and
    identifying the candidate compound as a compound capable of regulating a plasma membrane protein complex based on the changes in the quantified ratio of detected alternative stoichiometries of the protein complex in the region of interest following contact of the candidate compound.

5. The method of claim 4, wherein the region of interest is formed by a plurality of regions and corresponding changes in various regions of interest are associated with a regulated status of the protein complex.

6. A method to identify a compound capable of functionally regulating a plasma membrane protein complex, the method comprising:
providing one or more stoichiometries of the plasma membrane protein complex;
incubating a cell expressing the plasma membrane protein complex with a candidate compound;
quantitatively detecting the one or more stoichiometries of the plasma membrane protein complex following the incubating, the quantification performed with the method of claim 1;
comparing the one or more quantitatively detected plasma membrane protein complex stoichiometries with predetermined quantified stoichiometries associated with a regulation state of the plasma membrane protein complex; and
identifying the candidate compound capable of regulating a plasma membrane protein complex based on the association of the one or more quantitatively detected plasma membrane protein complex stoichiometries with the predetermined quantified stoichiometries associated with the regulation state of the plasma membrane protein complex.

7. The method of claim 6 wherein the quantitative detection of the one or more stoichiometries is repeated in increments of time.

8. The method of claim 6 wherein the calculating is performed by:
compiling a distribution of identified FRET amplitudes as a function of a number of pixels associated with each FRET amplitude;
and the correlating is performed by
identifying on the FRET distribution one or more components, each component associated with a predetermined stoichiometry;
detecting the one or more mean FRET amplitudes associated with the one or more stoichiometries based on the identified one or more components; and
quantifying the one or more stoichiometries as a percentage of the total population of stoichiometries by dividing the area of the one or more components associated with the one or more stoichiometry by the area of the distribution.

9. The method of claim 6 wherein said identified candidate compound is a compound identified as beneficial to the fields of human and veterinary medicine.

10. The method of claim 6 wherein said identified candidate compound is an effective smoking cessation therapies, a treatment for Parkinson's Disease or Autosomal dominant nocturnal frontal lobe epilepsy (ADNFLE) or an antihelmintic that targets specific stoichiometries of nAChRs expressed in the nerves and muscle of parasitic nematodes that infect humans or livestock.

11. A method to detect interactions of protein complexes with another protein, the method comprising:
detecting one or more stoichiometries of the protein complex with the method of claim 1, wherein
identification of mean FRET efficiencies uncorrelated with the theoretically calculated FRET efficiencies indicates interaction with of the protein complex with the another protein.

* * * * *